US008119255B2

(12) United States Patent
Xia et al.

(10) Patent No.: US 8,119,255 B2
(45) Date of Patent: Feb. 21, 2012

(54) CROSS-LINKABLE IRIDIUM COMPLEXES AND ORGANIC LIGHT-EMITTING DEVICES USING THE SAME

(75) Inventors: Chuanjun Xia, Lawrenceville, NJ (US); Raymond Kwong, Plainsboro, NJ (US); Jason Brooks, Philadelphia, PA (US)

(73) Assignee: Universal Display Corporation, Ewing, NJ (US)

( * ) Notice: Subject to any disclaimer, the term of this patent is extended or adjusted under 35 U.S.C. 154(b) by 1085 days.

(21) Appl. No.: 11/951,879

(22) Filed: Dec. 6, 2007

(65) Prior Publication Data

US 2008/0220265 A1    Sep. 11, 2008

Related U.S. Application Data

(60) Provisional application No. 60/873,581, filed on Dec. 8, 2006, provisional application No. 60/940,310, filed on May 25, 2007.

(51) Int. Cl.
*H01L 51/54* (2006.01)
(52) U.S. Cl. ........ 428/690; 428/917; 313/504; 313/506; 257/E51.044
(58) Field of Classification Search .................. None
See application file for complete search history.

(56) References Cited

U.S. PATENT DOCUMENTS

| 5,281,489 | A * | 1/1994 | Mori et al. ..................... 428/690 |
| 5,518,824 | A * | 5/1996 | Funhoff et al. ............... 428/690 |
| 5,929,194 | A | 7/1999 | Woo et al. |
| 6,905,784 | B2 * | 6/2005 | Seo ............................... 428/690 |
| 6,913,710 | B2 | 7/2005 | Farrand et al. |
| 2004/0048101 | A1 * | 3/2004 | Thompson et al. ........... 428/690 |
| 2004/0175638 | A1 | 9/2004 | Tierney et al. |
| 2005/0019605 | A1 | 1/2005 | Kwong et al. |
| 2005/0158523 | A1 | 7/2005 | Gupta et al. |
| 2006/0065890 | A1 | 3/2006 | Stossel et al. |
| 2006/0119254 | A1 | 6/2006 | Samuel et al. |

FOREIGN PATENT DOCUMENTS

| WO | WO 03/079736 A1 * | 9/2003 |
| WO | WO 2004/041962 | 5/2004 |
| WO | WO 2005/021678 | 3/2005 |
| WO | WO 2005/027583 | 3/2005 |
| WO | WO 2006/001150 | 1/2006 |
| WO | WO2006/014599 | 2/2006 |

OTHER PUBLICATIONS

PCT International Search Report From PCT/US2007/025353, mailed on Oct. 16, 2008.
Takayama et al., "Soluble Polymer Complexes Having AlQ3-Type Pendent Groups", Macromolecular Rapid Communications, 25:1171-1174, 2004.
Lafolet et al., "Iridium complexes containing p-phenylene units. The influence of the conjugation on the excited state properties". J. Of Materials Chemistry. 15(12):2820-2828, 2005.
Bacher et al., "Photo-Cross-Linked Triphenylenes as Novel Insoluble Hole Transport Materials in Organic LEDs", Macromolecules 32:4551-4557, 1999.
Bacher et al., "Synthesis and Characterization of Photo-Cross-Linkable Hole-Conducting Polymers", Macromolecules 28:1640-1647, 2005.
Bellmann et al., "New Triarylamine-Containing Polymers as Hole Transport Materials in Organic Light Emitting Diodes: Effect of Polymer Structure and Cross-Linking on Device Characteristics", Chem. Mater. 10:1668-1676, 1998.
Ding et al., "Highly Efficient Green-Emitting Phosphorescent Iridium Dendrimers Based on Carbazole Dendrons", Adv. Funct. Mater. 16:575-581, 2006.
Domercq et al., "Organic Light-Emitting Diodes with Multiple Photocrosslinkable Hole-Transport Layers", J. of Polymer Science: Part B: Polymer Physics. 41:2726-2732, 2003.
Domercq et al., "Photo-Pattemable Hole Transport Polymers for Organic Light Emitting Diodes", Chem. Mater. 15:1491-1496. 2003.
Evans et al., "Triplet Energy Back Transfer in Conjugated Polymers with Pendant Phosphorescent Iridium Complexes", J. Am. Chem. Soc. 128:6647-6656, 2006.
Jiang et al., "High Efficiency Electrophosphorescent Fluorene-alt-carbazole Copolymers N-Grafted with Cyclometalated Ir Complexes", Macromolecules 38:4072-4080, 2005.
Jiang et al., "Perfluorocyclobutane-based arylamine Hole-Transporting Materials for Organic and Polymer Light Emitting Diodes", Adv. Funct. Mater. 12(11-12): 745-751, 2002.
Li et al., "Multifunctional platinum porphyrin dendrimers as emitters in undoped phosphorescent based light emitting devices", Appl. Phys. Lett. 89:061125-1-061125-3, 2006.
Liu et al., "Red Phosphorescent Iridium Complex Containing Carbazole-Functionalized β-Diketonate for Highly Efficient Nondoped Organic Light-Emitting Diodes", Adv. Funct. Mater. 16:1441-1448, 2006.
Nuyken et al., "Crosslinkable hole- and electron-transport materials for application in organic light emitting dioes (OLEDs)", Designed Monomers and Polymers 5(2): 195-210, 2002.
Sandee et al., "Solution Processible Conjugated Electrophosphorescent Polymers", J. Am. Chem. Soc. 126:7041-7048, 2004.
Schulz et al., "Enhancement of Phosphorescence of Ir Complexes Bound to Conjugated Polymers: Increasing the Triplet Level of the Main Chain", Macromolecules 39:9157-9165, 2006.
Wang et al., "Polymer-based Tris (2-phenylpyridine)Iridium complexes", Macromolecules 39:3140-3146, 2006.

(Continued)

*Primary Examiner* — Marie R. Yamnitzky
(74) *Attorney, Agent, or Firm* — Kenyon & Kenyon LLP

(57) ABSTRACT

Organic devices comprising an organic layer, wherein the organic layer is non-electroluminescent and comprises a cross-linked metal complex. The cross-linked metal complex may be formed by cross-linking a cross-linkable iridium complex, which comprises a set of ligands coordinated to a central iridium atom. One or more of the ligands have attached thereon, one or more polymerizable groups that are able to polymerize with other molecules to form intermolecular covalent bonds. In some cases, the organic layer may also comprise a dopant. Also provided are a method of making an organic light-emitting device, an iridium complex, and an organic-light emitting device using certain iridium complexes.

31 Claims, 9 Drawing Sheets

OTHER PUBLICATIONS

Wong et al., "A multifunctional platinum based triplet emitter for OLED applications", Organometallics 24:4079-4082, 2005.

Wong et al., "Multifunctional iridium complexes based on carbazole modules as highly efficient electrophosphors", Angew. Chem. Int. Ed. 45:7800-7803, 2006.

You et al., "Blue electrophosphorescence from Iridium Complex Covalently Bonded to the Poly (9-dodecyl-3-vinylcarbazole): Suppressed Phase Segregation and Enhanced Energy Transfer", Macromolecules 39:349-356, 2006.

Zhang et al., "Highly efficient polymer light-emitting diodes using color-tunable carbazole based iridium complexes", Chem. Phys. Lett. 422:386-390, 2006.

Zhang et al., "Saturated Red-Emitting Electrophosphorescent Polymers with Iridium Coordinating to β-Diketonate Units in the Main Chain", Macromo. Rapid Commun. 27:1926-1931, 2006.

\* cited by examiner

CROSS-LINKABLE IRIDIUM COMPLEXES AND ORGANIC LIGHT-EMITTING DEVICES USING THE SAME

CROSS-REFERENCES

This application claims priority to U.S. Provisional Application Ser. No. 60/873,581 (filed 8 Dec. 2006) and Ser. No. 60/940,310 (filed 25 May 2007). Both of these provisional applications are incorporated by reference herein in their entirety.

TECHNICAL FIELD

The present invention relates to organic light-emitting devices (OLEDs), and more specifically to organic light-emitting devices using certain metal complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

SUMMARY

In one aspect, the present invention provides an organic light-emitting device, comprising: a first electrode; a second electrode; a first organic layer disposed between the first electrode and the second electrode, wherein the first organic layer is non-electroluminescent, and wherein the first organic layer comprises a cross-linked metal complex; and a second organic layer disposed between the first electrode and the second electrode, wherein the second organic layer is emissive, and wherein the second organic layer comprises an electroluminescent organic material. In some cases, the first organic layer further comprises a dopant.

In certain instances, the cross-linked metal complex is formed by cross-linking a cross-linkable iridium complex having the formula:

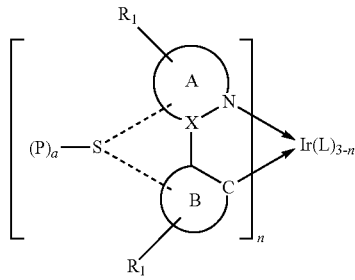

wherein L is a ligand coordinated to the iridium;
wherein A and B are each a 5 or 6-membered aromatic ring, and wherein A-B represents a bonded pair of aromatic rings coordinated to the iridium via a nitrogen atom on ring A and an sp² hybridized carbon atom on ring B;
wherein variable "n" has an integer value of 1-3;
wherein X is a carbon or nitrogen atom;
wherein P is a polymerizable group with variable "a" having an integer value of 1-5;
wherein S is a spacer group that includes one or more linkage units that are each independently selected from the group consisting of: alkylene, heteroalkylene, arylene, heteroarylene, borane, ether, ester, amine, imine, amide, imide, thioether, and phosphine; and
wherein each of rings A and B are optionally substituted with groups $R_1$ and $R_2$, respectively, wherein each of $R_1$ and $R_2$ represents one or more independently selected substitutions located on any position of their respective rings, wherein each of the substitutions are fused or linked to their respective rings, and wherein each of the substitutions are independently selected from the group consisting of: alkyl, heteroalkyl, aryl, and heteroaryl.

In another aspect, the present invention provides a method of making an organic light-emitting device, comprising: providing a first electrode disposed on a substrate; forming a first organic layer by solution depositing a cross-linkable metal complex over the first electrode and cross-linking the cross-linkable metal complex; forming a second organic layer over the first electrode, wherein the second organic layer comprises an organic electroluminescent material; and forming a second electrode disposed over the first and second organic layers. In some cases, the solution used in solution depositing the cross-linkable metal complex further comprises a dopant.

In another aspect, the present invention provides an iridium complex having the formula:

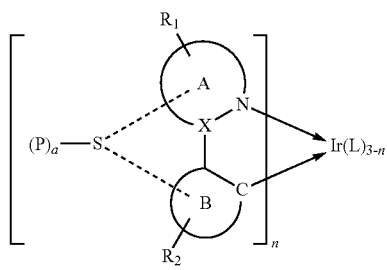

wherein L is a ligand coordinated to the iridium;
wherein A and B are each a 5 or 6-membered aromatic ring, and wherein A-B represents a bonded pair of aromatic rings coordinated to the iridium via a nitrogen atom on ring A and an sp² hybridized carbon atom on ring B;
wherein variable "n" has a numerical value of 1-3;
wherein P is a polymerizable group with variable "a" having an integer value of 1-5;
wherein S is a spacer group containing an amine group; and
wherein each of rings A and B are optionally substituted with groups $R_1$ and $R_2$, respectively, wherein each of $R_1$ and $R_2$ represents one or more substitutions, wherein each of the one or more substitutions are located on any position of their respective rings, wherein each of the substitutions are the same or different, wherein each of the substitutions are fused or linked to their respective rings, and wherein each of the substitutions are independently selected from the group consisting of: alkyl, heteroalkyl, aryl, and heteroaryl.

In another aspect, the present invention provides an organic light-emitting device, comprising: a first electrode; a second electrode; and a first organic layer comprising a covalently cross-linked matrix, wherein the cross-linked matrix comprises an iridium complex. In some cases, the first organic layer further comprises a dopant.

DETAILED DESCRIPTION

Figure 1:
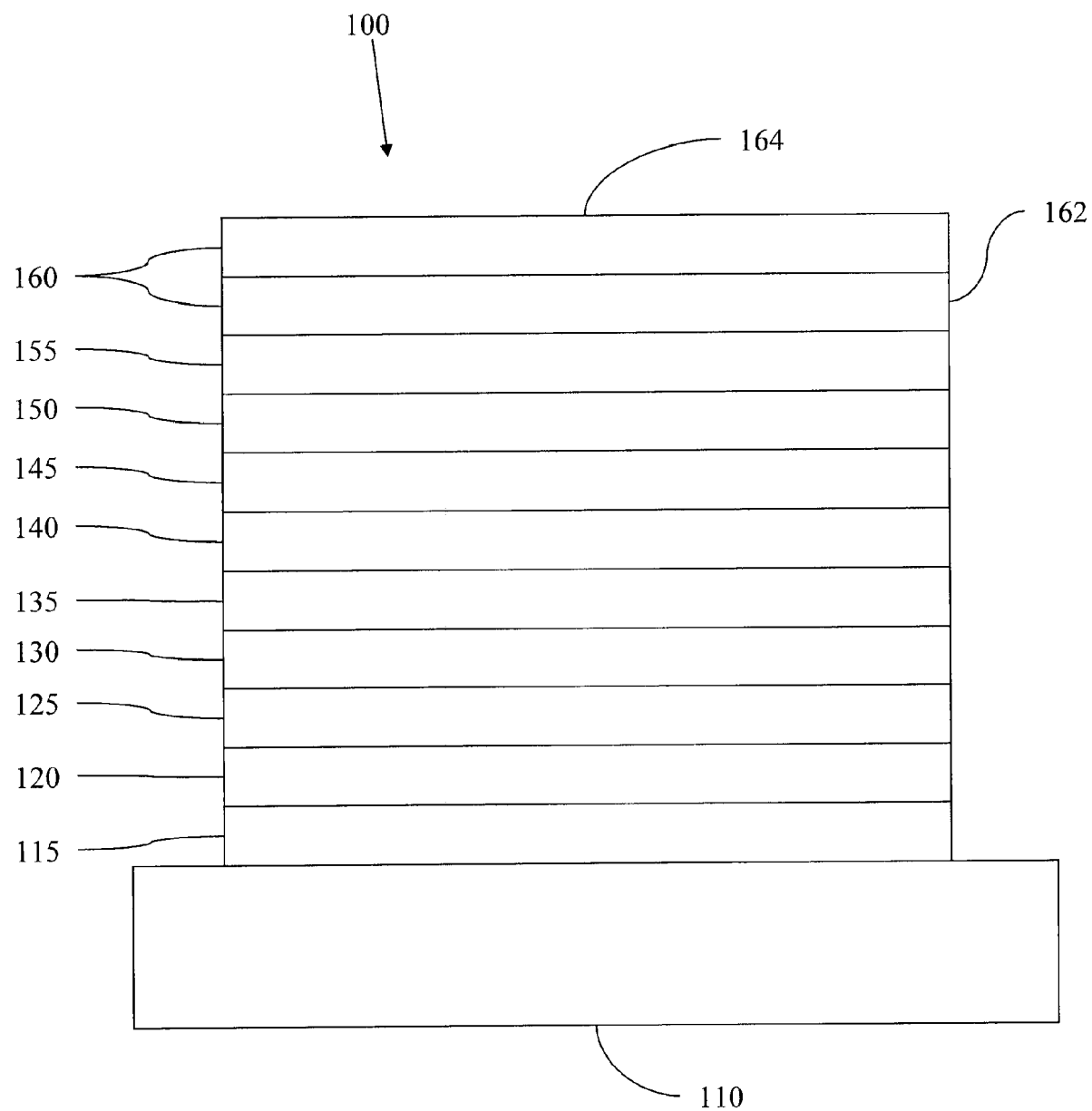
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 1, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. Alq$_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
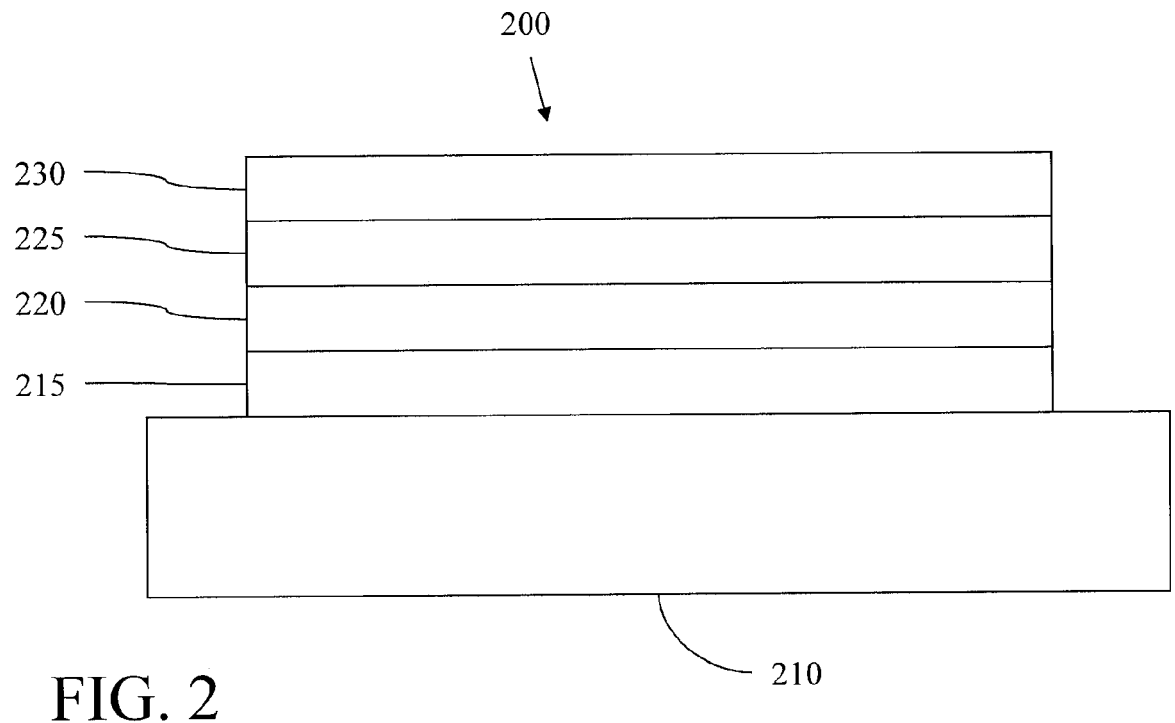
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In one aspect, the present invention provides an organic electronic device comprising a first organic layer, wherein the first organic layer comprises a cross-linked metal complex. The organic electronic device may be a light-emitting device, field-effect transistor, photovoltaic device, and the like. In an organic light-emitting device, the first organic layer may be a charge transport layer such as a hole transport layer, hole injection layer, electron transport layer, or electron injection layer.

In certain instances, the organic electronic device is an organic light-emitting device which comprises a first electrode and a second electrode, wherein the first organic layer is disposed between the first electrode and the second electrode. In some instances, the first electrode is an anode and the first organic layer is in direct contact with the first electrode.

Metal complexes have certain properties that allow them to be suitable for use as charge transport materials. For example, using metal complexes such as CuPC in the hole injection layer can provide stable device operation. Some metal complexes, such as Ir(III), Co(III), and Fe(II) complexes, can be reversibly oxidized, thus making them suitable for use as hole injection or charge transport materials. In addition, cross-linking of the metal complexes can serve various functions which can be useful in device fabrication and/or operation. For example, cross-linking may affix the metal complexes to the substrate or other surfaces to provide high physical robustness.

In certain instances, the first organic layer is non-electroluminescent. As used herein, the term "non-electroluminescent" means that the layer has a luminescence of less than 1 $cd/m^2$.

The cross-linked metal complex may be a cross-linked organometallic complex, such as an organometallic iridium complex. In certain instances, the cross-linked metal complex is formed by cross-linking a cross-linkable iridium complex. The cross-linkable iridium complex comprises a set of ligands coordinated to a central iridium atom. One of more of the ligands have attached thereon, one or more polymerizable groups that are able to polymerize with other molecules to form intermolecular covalent bonds. For example, a plurality of cross-linkable iridium complexes may cross-link with each other via their polymerizable groups. The polymerizable groups may be positioned anywhere on the ligand, and in some cases, may form a terminal group on the ligand.

In certain instances, the cross-linkable iridium complex is represented by Formula I, as shown below:

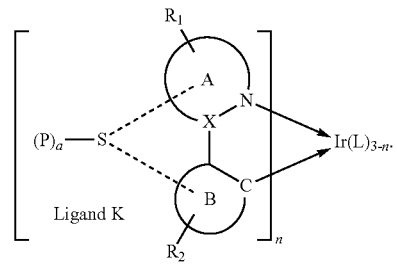

Formula I

Each L represents a ligand that coordinates with the iridium, including any of various bidentate ligands which contain delocalized π-electrons, or which serve to improve the solubility (aqueous or organic), mesogenic property, or charge transport capability of the iridium complex. For example, the ligand L may be a phenylpyridine or acetylacetone.

Each K also represents a ligand, which comprises a structure $R_1$-A-B—$R_2$, spacer group S, and one or more polymerizable groups P. The variable "n" has an integer value ranging from 1 to 3. Where n=1, the ligands L may be same or different from each other. Where n=2 or n=3, each of the ligands K may be same or different from each other.

The structure A-B represents a pair of aromatic rings that are bonded to each other. Rings A and B are each a 5 or 6-membered ring. Atom X on ring A represents a heteroatom, which may be nitrogen or carbon. The structure A-B is coordinated to the iridium via a nitrogen atom on ring A and an $sp^2$ hybridized carbon on ring B.

Each of rings A or B may optionally be substituted by substitution groups $R_1$ and $R_2$, wherein each of $R_1$ and $R_2$ represents one or more independently selected substitutions located at any position on their respective rings. $R_1$ or $R_2$ may be linked or fused to their respective rings. The $R_1$ and $R_2$ substitution groups can include alkyl, heteroalkyl, aryl, and heteroaryl.

The term "alkyl" as used herein refers to alkyl moieties and encompasses both straight and branched alkyl chains. Preferred alkyl moieties are those containing one to fifteen carbon atoms and includes methyl, ethyl, propyl, isopropyl, butyl, isobutyl, tert-butyl, and the like. Additionally, the alkyl moieties themselves may be substituted with one or more substituents. The term "heteroalkyl" as used herein refers to alkyl moieties that include heteroatoms.

The term "aryl" as used herein refers to aryl moieties and encompasses structures containing at least one aromatic ring, including single-ring groups and polycyclic ring systems. The polycyclic rings may have two or more rings in which two atoms are common by two adjoining rings (the rings are "fused") wherein at least one of the rings is aromatic.

The term "heteroaryl" as used herein refers to heteroaryl moieties and encompasses single-ring heteroaromatic groups that may include from one to four heteroatoms. Examples of heteroaryl moieties include pyrrole, furan, thiophene, imidazole, oxazole, thiazole, triazole, tetrazole, pyrazole, pyridine, pyrazine, and pyrimidine, and the like. The term "heteroaryl" also includes polycyclic heteroaromatic systems having two or more rings in which two atoms are common to two adjoining rings (the rings are "fused") wherein at least one of the rings is a heteroaryl. The other rings can be cycloalkyls, cycloalkenyls, aryl, heterocycles, and/or heteroaryls.

In some instances, ring A may be a pyridine, pyrimidine, quinoline, isoquinoline, imidazole, benzimidazole, or pyrazine. Examples of $R_1$-A-B—$R_2$ structures suitable for use in ligand K include:

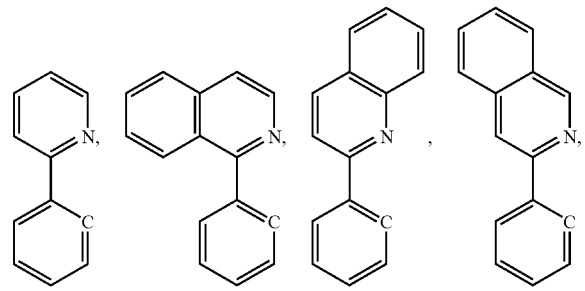

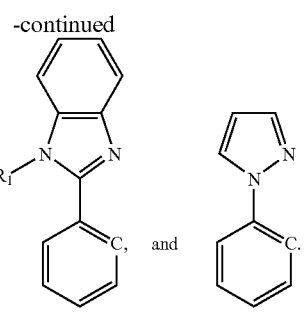

P represents a polymerizable group that is attached to spacer group S. As used herein, "polymerizable group" refers to any atom, functional group, or portion of a molecule having sufficient reactivity to form at least one covalent bond with another cross-linkable iridium complex, with a cross-linking agent, or with a co-monomer. The variable "a" represents the number of polymerizable groups on the spacer group and may have an integer value of 1-5. In some instances, variable "a" has a value of 2 or greater. In some instances, the polymerizable group P is a terminal group on the spacer group.

Various polymerizable groups are known in the art, including those derived from amines, imides, amides, alcohols, esters, epoxides, siloxanes, moieties containing unsaturated carbon-carbon bonds, and strained ring compounds. For example, the polymerizable groups may be a vinyl, acrylate, epoxide, oxetane, trifluoroethylene, benzocyclobutene, siloxane, maleimide, cyanate ester, ethynyl, nadimide, phenylethynyl, biphenylene, phthalonitrile, or boronic acid. In some cases, the polymerizable groups may be vinyl, siloxane, or boronic acid.

S represents a spacer group, which is attached to one or both of rings A or B by a linkage or by ring fusion. The spacer group may contain one or more bonds and/or linkage units. In certain instances, the linkage units may be branched. Linkage units suitable for use in the spacer group include alkylene, heteroalkylene, arylene, heteroarylene, borane, ether, ester, amine, imine, amide, imide, thioether, and phosphine units.

In certain instances, the spacer group is selected to facilitate the ability of the polymerizable group to engage in polymerization reactions; improve the electrochemical stability of the iridium complex or the first organic layer; and/or improve the operational lifetime of the organic electronic device. For example, increasing the length of the spacer group can facilitate polymerization by reducing steric interference to the polymerizable groups. Also, the spacer group may be designed to have increased flexibility, or to impart increased range of motion or degrees of freedom to the polymerizable group. In some cases, the spacer group may separate the polymerizable group from one of the pair of aromatic rings, A or B, by a distance of at least 5 bonds; and in some cases, this distance may be at least 7 bonds.

In some instances, the spacer group contains a nitrogen. For example, the spacer group may contain an amine group, such as a triphenylamine structure. Without intending to be bound by theory, it is believed that amino groups can modulate the HOMO and LUMO levels to enhance the electrochemical properties of the cross-linkable iridium complex. As such, a spacer group containing an amino group can be used to tune or enhance the performance of the organic electronic device.

In certain instances, the cross-linkable iridium complexes are monomeric units. Cross-linking of the monomeric units forms polymers or polymeric matrices. In other instances, the cross-linkable iridium complexes are cross-linkable polymeric molecules or a part thereof. For example, the iridium complex may constitute the backbone of the polymer or constitute a side group on the polymer chain. Cross-linking of the polymeric molecules produces larger polymers or polymeric matrices containing the iridium complex.

In certain instances, the cross-linkable iridium complex is represented by Formula II, as shown below:

Formula II

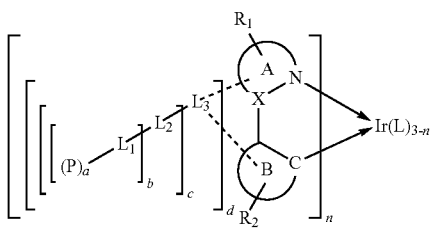

In Formula II, spacer group S comprises $L_1$, $L_2$, and $L_3$, each of which independently represents a direct bond linkage or a linkage unit selected from the group consisting of any single atom, alkylene, heteroalkylene, arylene, heteroarylene, borane, ether, ester, amine, imine, amide, imide, thioether, and phosphine. Each of variables "a," "b," "c," and "d" has an integer value of 1-5. When representing a direct bond linkage, $L_1$, $L_2$, or $L_3$ consists of a bond connecting two adjacent units. For example, $L_2$ may represent a bond between $L_1$ and $L_3$. In another example, $L_3$ may represent a bond between ring B and $L_2$. Further, more than one of $L_1$, $L_2$, and $L_3$ may be direct bond linkages. Thus, it is readily apparent to one of ordinary skill in the art that $L_1$, $L_2$, and $L_3$ can be combined in various ways to represent iridium complexes as expressed by Formula II.

In some instances, the cross-linkable iridium complex of Formula II is:

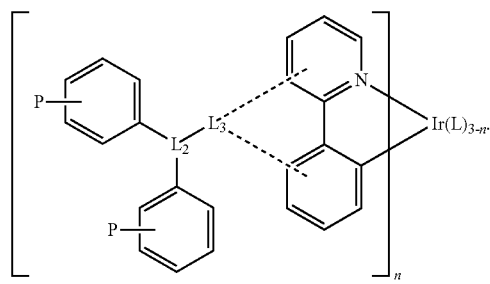

Here, there are two $L_1$ units, each of which are a phenyl ring substituted with a polymerizable group P on any position on the phenyl ring. $L_2$ is an intermediate branching unit that is bonded to the two $L_1$ units.

In some instances, the cross-linkable iridium complex of Formula II is:

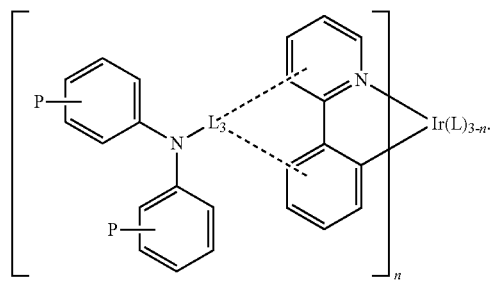

This particular iridium complex can be expressed by Formula II in various ways. In one example, $L_2$ is the nitrogen atom which is bonded to the two P-substituted phenyl rings, each representing $L_1$. In another example, $L_1$ represents the P-substituted N-phenylaniline structure and $L_2$ represents the bond between $L_1$ and $L_3$.

In some instances, the cross-linkable iridium complex of Formula II is:

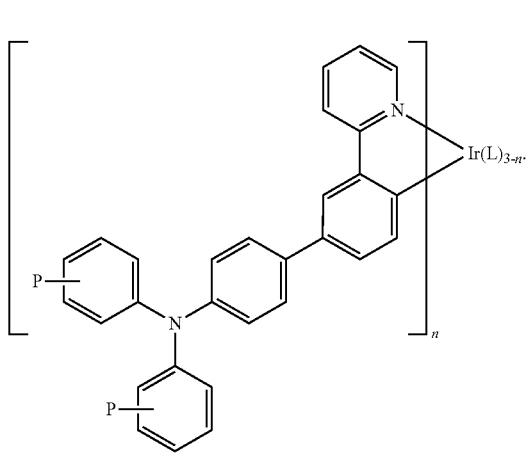

This particular iridium complex can be expressed by Formula II in various ways. In one example, $L_3$ is a phenyl ring that serves as a linker for the $L_1$-$L_2$ group. In another example, $L_1$ is the P-substituted triphenylamine structure and the combination of $L_2$ and $L_3$ represent the bond between $L_1$ and ring B.

In another aspect, the present invention provides a method of making an organic light-emitting device. The method comprises providing a substrate with a first electrode disposed thereon. A first organic layer is formed by solution depositing a cross-linkable metal complex over the first electrode and then cross-linking the cross-linkable metal complex. In certain instances, the first electrode is an anode and the first organic layer is in direct contact with the first electrode.

Cross-linking can be performed by exposing the charge transport material to heat and/or actinic radiation, including UV light, gamma rays, or x-rays. Cross-linking may be carried out in the presence of an initiator that decomposes under heat or irradiation to produce free radicals or ions that initiate the cross-linking reaction. The cross-linking may be performed in-situ during fabrication of the device.

An organic layer formed of a covalently cross-linked matrix can be useful in the fabrication of organic devices by solution processing techniques, such as spin coating, spray coating, dip coating, ink jet, and the like. In solution processing, the organic layers are deposited in a solvent. Therefore, in a multi-layered structure, any underlying layer is preferably resistant to the solvent that is being deposited upon it.

Thus, in certain instances, the cross-linking of the first organic layer can render the organic layer resistant to solvents. As such, the first organic layer can avoid being dissolved, morphologically influenced, or degraded by a solvent that is deposited over it. The first organic layer may be resistant to a variety of solvents used in the fabrication of organic devices, including toluene, xylene, anisole, and other substituted aromatic and aliphatic solvents. The process of solution deposition and cross-linking can be repeated to create a multilayered structure.

In certain instances, the method further comprises forming a second organic layer over the first organic layer, wherein the second organic layer comprises an organic electroluminescent material. In some instances, the second organic layer is formed by solution deposition. In some instances, the first organic layer is insoluble in the solvent used in depositing the second organic layer.

In certain instances, the method further comprises forming a third organic layer over the first organic layer, wherein the third organic layer comprises a hole transport material and is disposed between the first organic layer and the second organic layer. In some instances, the third organic layer is formed by solution deposition. In some instances, the first organic layer is insoluble in the solvent used in depositing the third organic layer. In some instances, the hole transport material in the third organic layer is cross-linked.

In certain instances, the cross-linkable metal complex is represented by Formula I, wherein L is a ligand coordinated to the iridium;

wherein A and B are each a 5 or 6-membered aromatic ring, and wherein A-B represents a bonded pair of aromatic rings coordinated to the iridium via a nitrogen atom on ring A and an $sp^2$ hybridized carbon atom on ring B;

wherein variable "n" has an integer value of 1-3;

wherein X is a carbon or nitrogen atom;

wherein P is a polymerizable group with variable "a" having an integer value of 1-5;

wherein S is a spacer group that includes one or more linkage units that are each independently selected from the group consisting of: alkylene, heteroalkylene, arylene, heteroarylene, borane, ether, ester, amine, imine, amide, imide, thioether, and phosphine; and wherein each of rings A and B are optionally substituted with groups $R_1$ and $R_2$, respectively, wherein each of $R_1$ and $R_2$ represents one or more independently selected substitutions located on any position of their respective rings, wherein each of the substitutions are fused or non-fused, and wherein each of the substitutions are independently selected from the group consisting of: alkyl, heteroalkyl, aryl, and heteroaryl.

In yet another aspect, the present invention provides a cross-linkable iridium complex of Formula I, wherein L is a ligand coordinated to the iridium;

wherein A and B are each a 5 or 6-membered aromatic ring, and wherein A-B represents a bonded pair of aromatic rings coordinated to the iridium via a nitrogen atom on ring A and an $sp^2$ hybridized carbon atom on ring B;

wherein variable "n" has a numerical value of 1-3;

wherein P is a polymerizable group with variable "a" having an integer value of 1-5;

wherein S is a spacer group containing an amine group; and wherein each of rings A and B are optionally substituted with groups $R_1$ and $R_2$, respectively, wherein each of $R_1$ and $R_2$ represents one or more substitutions, wherein each of the one or more substitutions are located on any position of their respective rings, wherein each of the substitutions are the same or different, wherein each of the substitutions are fused or linked to their respective rings, and wherein each of the substitutions are independently selected from the group consisting of: alkyl, heteroalkyl, aryl, and heteroaryl.

In certain instances, the spacer group S is represented by the structure:

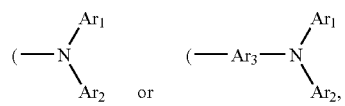

wherein $Ar_1$, $Ar_2$, and $Ar_3$ are each an aryl group.

In certain instances, the spacer group S is represented by the structure:

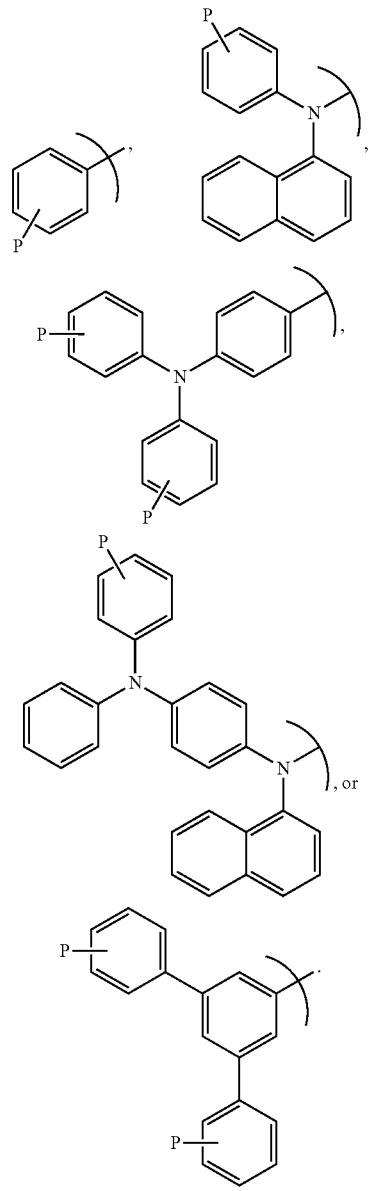

In certain instances, in addition to the aforementioned structures, the spacer group S is further represented by the structure:

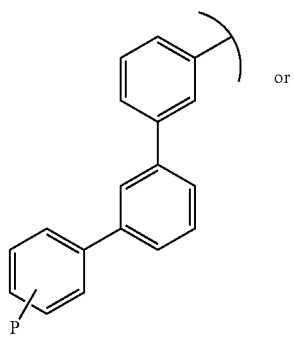

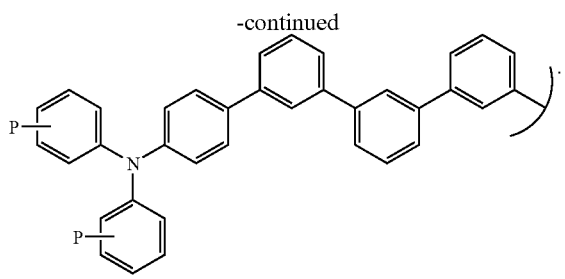

In certain instances, the cross-linkable iridium complex is any of Compounds 1-9 as identified below. In certain instances, the cross-linkable iridium complex is any of Compounds 10-18 as identified below.

In certain instances, the first organic layer may further comprise any of various dopants which may be selected for their electrical properties. The dopants may serve to increase the conductivity of the layer. For example, the dopants may be strong electron acceptors such as F4-TCNQ or tris(pentafluorophenyl)borane; or strong electron donors such as trialkylamines, triarylamines, or alkali metals; or strong oxidants such as ferric chloride or iodine. In addition, the dopant system can be selected to adjust the interaction between the hole injection layer and the anode (e.g., ITO) surface. A localized highly doped region close to the anode surface can facilitate charge injection into the hole injection layer.

In some cases, the dopant may be any of the ionic compounds disclosed in European Patent Application EP 1,725,079 (Iida et al.). In some cases, the dopant may be any of the electron acceptor compounds disclosed in JP2005-075948 (Iida et al.). Some examples of suitable dopants include the following:

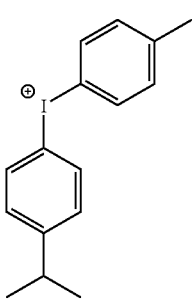

CD1 trityl-tetrakis(pentafluorophenyl)borate

CD2

4-isopropyl-4'-methyl-diphenyliodonium(pentafluorophenyl)borate

CD3

N,N-dimethylanilinium-tetrakis(pentafluorophenyl)borate

The dopant may be included in the organic layer in various ways. In certain instances, the dopant is a separate and distinct molecular species from the cross-linked metal complex (host material). In other instances, the dopant is incorporated into the host material. Incorporation of the dopant into the host material may be accomplished by bonding the dopant as a pendant group on the host material, by incorporating the dopant into the backbone of a host material, so as to form a co-polymer, or by formation of a charge-transfer complex between the dopant and the host material.

EXAMPLES

Specific representative embodiments of the invention will now be described, including how such embodiments may be made. It is understood that the specific methods, materials, conditions, process parameters, apparatus and the like do not necessarily limit the scope of the invention.

Synthesis of Compound 1

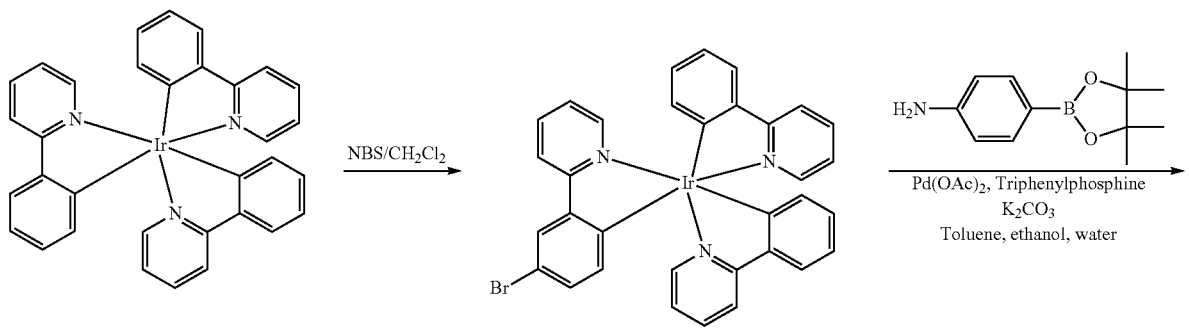

Intermediate A

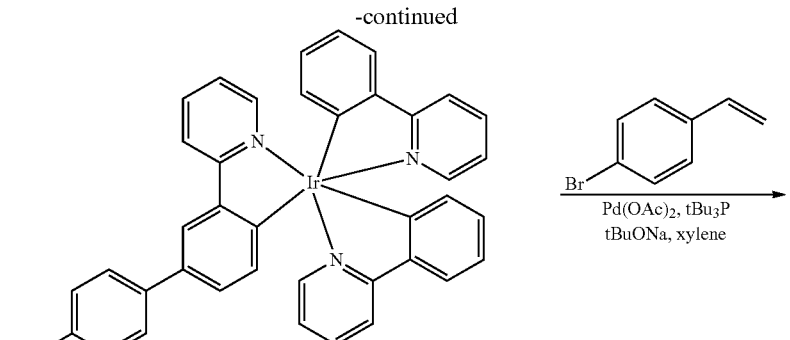

Intermediate B

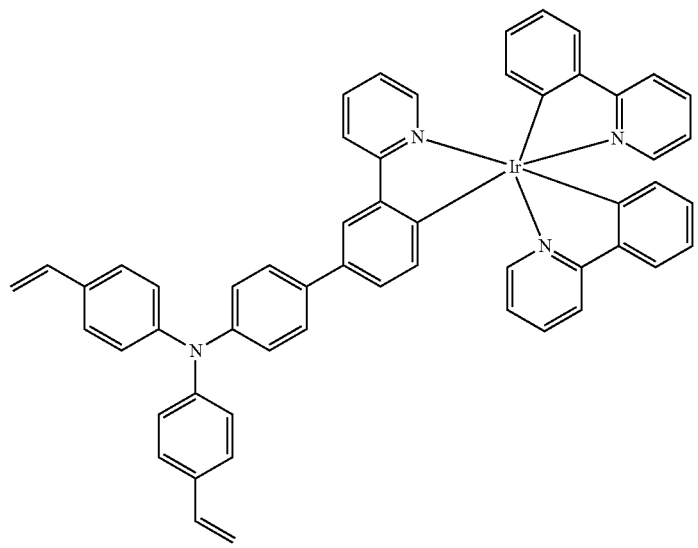

Compound 1

Intermediate A: fac-bis[2-(2-pyridinyl-κN)phenyl-κC]-[2-(2-pyridinyl-κN)-(5-bromophenyl)-κ C]iridium(III)

With the exclusion of light, a solution of 2.53 g (14.2 mmol) of N-bromosuccinimide in 200 ml dichloromethane was added dropwise to an efficiently stirred solution of 9.3 g (14.2 mmol) of fac-tris[2-(2-pyridinyl-κN)pheny-1-κC]iridium(III) in 2300 ml of dichloromethane. The solution was further stirred at room temperature for 15 hours. After concentrating under reduced pressure to a volume of 200 ml, the solution was admixed with 1000 ml of ethanol. Subsequently, the microcrystalline precipitate was filtered off, washed three times with 100 ml of ethanol, and then dried under reduced pressure. 9.3 g of product (Intermediate A) was obtained. The product contains about 80% of the desired monobromo product, 10% of the starting material, 10% of the dibromo product.

Intermediate B: 2.0 g (2.7 mmol) of fac-bis[2-(2-pyridinyl-κN)phenyl-κC]-[2-(2-pyridinyl-κN)-(5-bromophenyl)-κC]iridium(III) (Intermediate A), 0.9 g (4.1 mmol) of 4-(4,4,5,5-tetramethyl-1,3,2-dioxaborolan-2-yl)aniline, 1.0 g (7 mmol) of potassium carbonate, 500 mg of toluene, 100 ml of ethanol, and 50 ml of water were mixed and purged with nitrogen for 10 minutes. To the mixture was then added 0.3 g of Pd (PPh$_3$)$_4$. The mixture was heated to reflux for 30 hours. The mixture was cooled to room temperature and organic layer was separated. The solvent was evaporated under reduced pressure and the residue was purified in a column using dichloromethane as eluent. 1.2 g of product (Intermediate B) was obtained.

Compound 1: 1.34 mmol of fac-Bis[2-(2-pyridinyl-κN)phenyl-κC]-[2-(2-pyridinyl-κN)-(5-(4-aminophenyl)phenyl)-κ C]iridium(III) (Intermediate B), 0.49 g (2.68 mmol) of 4-bromostyrene, 9 mg of palladium acetate, 0.08 ml of 1 M tri-tert-butylphosphine in toluene, and 0.39 g (4.0 mmol) of sodium tert-butoxide, and 100 ml of p-xylene was heated to 110° C. for 6 hours under nitrogen. After cooling to room temperature, the reaction mixture was poured to 500 ml of methanol. The precipitate was collected and purified in a column using toluene as eluent. 0.36 g of product (Compound 1) was obtained after purification.

Synthesis of Compound 2

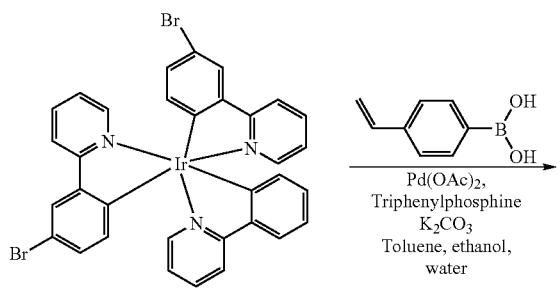

Compound 2

1.2 g (1.47 mmol) of fac-[2-(2-pyridinyl-κN)phenyl-κC]-Bis[2-(2-pyridinyl-κN)-(5-bromophenyl)-κ C]iridium(III), 0.6 g (4 mmol) of 4-vinylphenylboronic acid, 0.08 g of Pd(PPh$_3$)$_4$, 0.5 g (3.68 mmol) of potassium carbonate, 180 ml of toluene, 80 ml of ethanol, and 60 ml of water were added to a three-neck flask. The mixture was purged with nitrogen for 20 min and then heated up to reflux for 20 hours. After cooling to room temperature, the organic phase was separated and dried over magnesium sulfate. The solvent was evaporated under reduced pressure and the residue was purified in a column using 1:1 hexane and dichloromethane as eluent. 1.0 g of the product (Compound 2) was isolated.

Synthesis of Compound 3

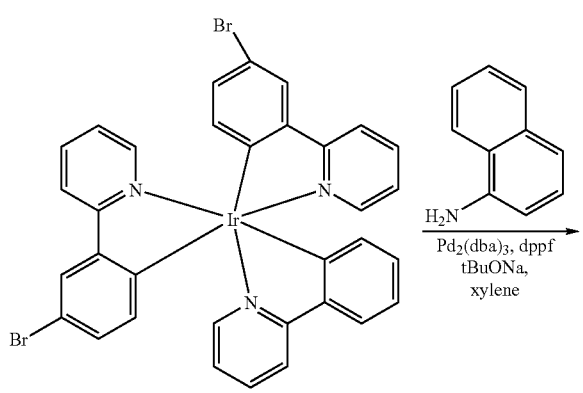

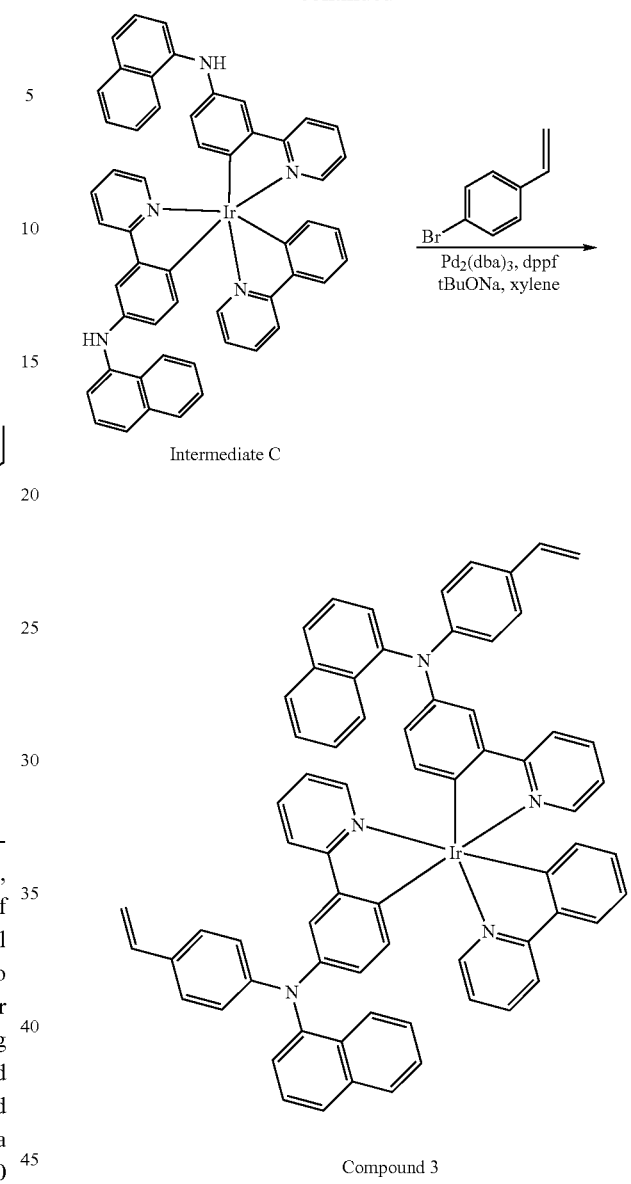

Intermediate C

Compound 3

0.02 g (0.08 mmol) of palladium acetate and 0.16 ml of 1M tri-tert-butylphosphine in toluene were added to 100 ml of toluene under nitrogen. The mixture was stirred under nitrogen until the color disappeared. To this solution was then added 2.0 g (2.5 mmol) of fac-[2-(2-pyridinyl-κN)phenyl-κC]-Bis[2-(2-pyridinyl-κN)-(5-bromophenyl)-κ C]iridium (III), 1.4 g (10 mmol) of 1-naphthalen-1-amine, and 0.72 g (7.5 mmol) of sodium tert-butoxide. The mixture was heated up to reflux for 20 hours. After cooling to room temperature, the reaction mixture was precipitated from methanol. The solid was collected by filtration and then purified in a column using 2:1 dichloromethane and hexane as eluent. 0.6 g of product (Intermediate C) was isolated. 0.5 g of the isolated product (Intermediate C) was further reacted with 2 equivalents of 4-bromostyrene under the same coupling conditions to give 0.2 g of Compound 3.

Synthesis of Compound 4

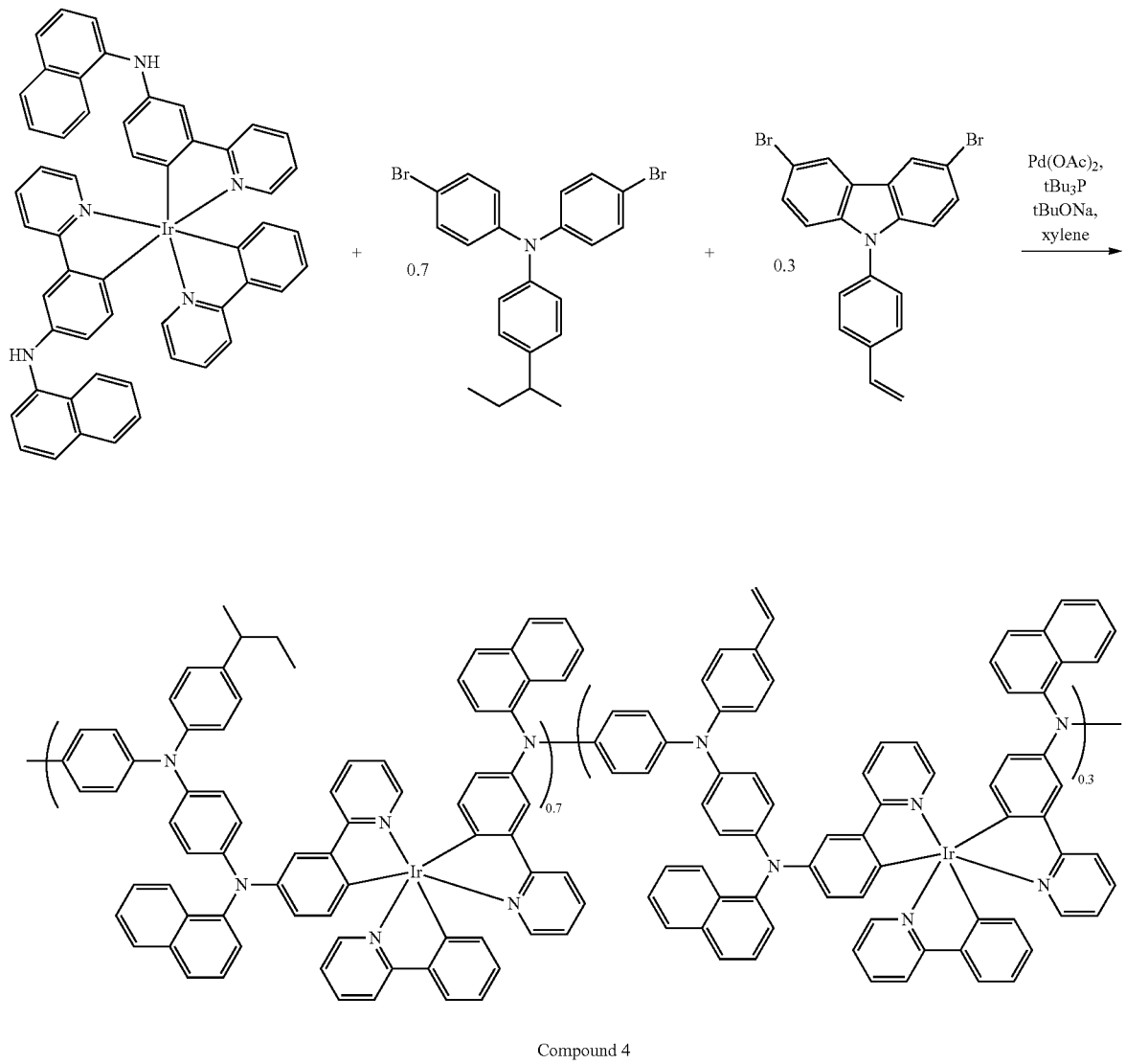

Compound 4

2 mg of palladium acetate and 0.02 ml of 1M tri-tert-butylphosphine in toluene were added to 40 ml of xylene under nitrogen. The mixture was stirred under nitrogen until the color disappeared. To this solution was then added 1.03 g (1.1 mmol) of the iridium containing diamine compound, 0.321 g (0.7 mmol) of 4-bromo-N-(4-bromophenyl)-N-(4-sec-butylphenyl)aniline, 0.128 g (0.3 mmol) of 3,6-dibromo-9-(4-vinylphenyl)-9H-carbazole, and 0.58 g (6.0 mmol) of sodium tert-butoxide. The mixture was heated to 120° C. for 3 hours. 0.2 g of iodobenzene was added. The reaction was further reacted for 2 hours. After cooling to room temperature, the reaction mixture was poured into methanol. The precipitate was collected by filtration. The solid was then passed through a triethylamine-treated silica gel column using toluene as the solvent. The solution was again poured into methanol. 0.2 g of polymeric Compound 4 was collected after drying under vacuum.

Synthesis of Compound 5

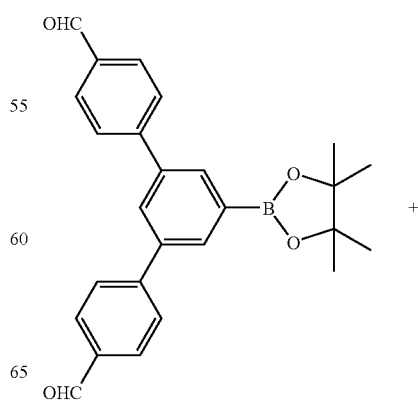

+

27

-continued

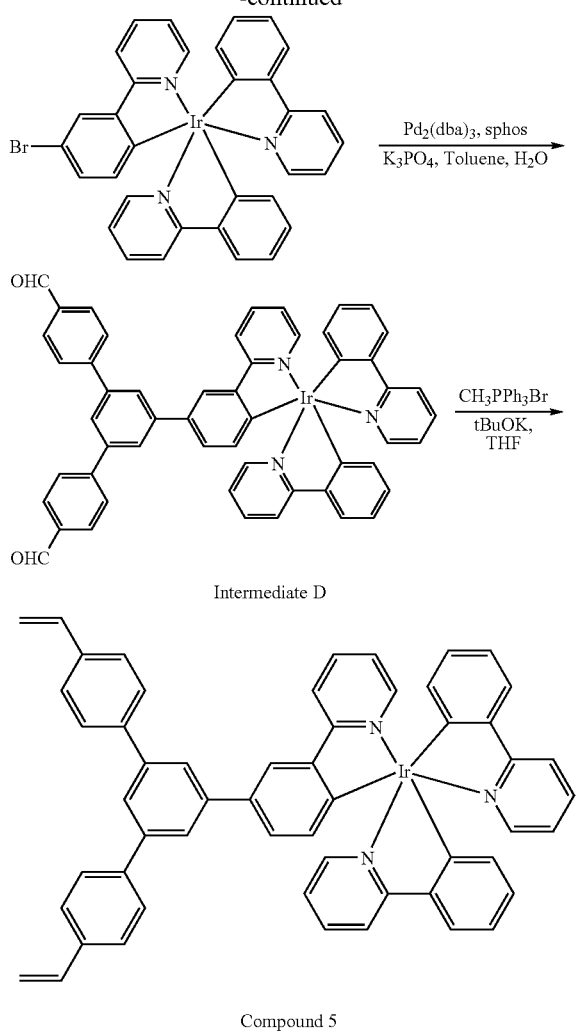

Intermediate D

Compound 5

Intermediate D: 2.14 g (2.9 mmol) of fac-bis[2-(2-pyridinyl-κN)phenyl-κC]-[2-(2-pyridinyl-κN)-(5-bromophenyl)-κ C]iridium(III), 1.8 g (4.4 mmol) of the boronic ester, 0.08 g (0.09 mmol) of $Pd_2(dba)_3$, 0.143 g (0.35 mmol) of sphos, 1.85 g (8.7 mmol) of potassium phosphate, 100 ml of toluene, and 10 ml of water were heated to reflux under nitrogen for 4 hours. After cooling to room temperature, the layers were separated. The organic layer was dried with magnesium sulfate. The solvent was evaporated and the residue was purified by column using 60% dichloromethane in hexanes. 2.33 g of pure product (Intermediate D) was isolated. The mass was confirmed with LC-MS.

Compound 5: 0.48 g (0.5 mmol) of Intermediate D was dissolved in 40 ml of anhydrous THF. To this solution was added 0.4 g of methyltriphenylphosphine bromide. The suspension was then cooled with an ice water bath. 1.5 ml of 1M potassium tert-butoxide in THF was added dropwise to the mixture. The reaction mixture was allowed to warm to room temperature for 30 minutes. The reaction mixture was poured into ice water and extracted with methylene chloride. After drying with magnesium sulfate and solvent evaporation, the product (Compound 5) was purified by column using 1:1 hexane and dichloromethane as solvent. 68 mg of pure Compound 5 was obtained.

28

Synthesis of Compound 6

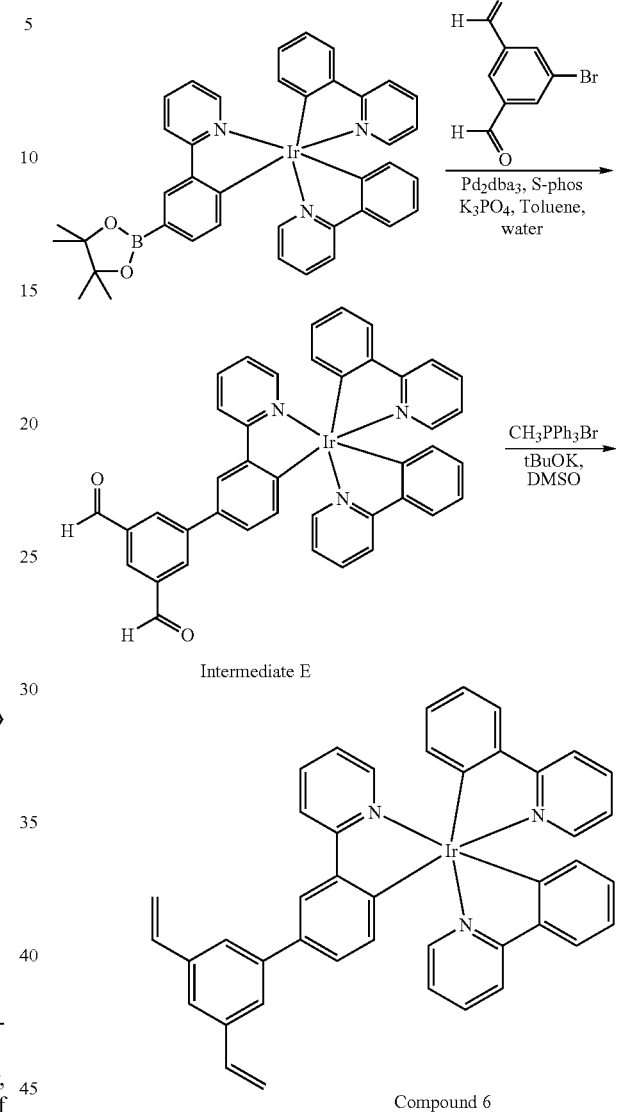

Intermediate E

Compound 6

Intermediate E: 1.99 g (2.55 mmol) of Irppy monoboronic ester, 0.65 g (3.06 mmol) of 5-bromoisophthalaldehyde, 0.628 g of S-Phos, 1.62 g of potassium phosphate were mixed in 4:1 toluene/water. The system was purged with nitrogen for 1 hour and 0.38 g of $Pd_2(dba)_3$ was then added. The mixture was heated up to reflux overnight. After cooling to room temperature, the mixture was extracted with dichloromethane, and washed with water. The residue was purified by column chromatography using dichloromethane as a solvent. 1.39 g of intermediate E was obtained.

Compound 6: 0.8 g of intermediate E was dissolved in 40 mL of anhydrous DMSO. To the solution was added 1.09 g of $CH_3PPh_3Br$. Then 3.05 mL of tert-butoxide in THF was added dropwise to the mixture and the mixture was stirred for 2 hours at room temperature. The reaction mixture was poured into 500 mL of water, and extracted with dichloromethane. After evaporating the solvent, the residue was purified by column chromatography using 50-75% dichloromethane/hexanes as solvent. 0.35 g of pale yellow product (Compound 6) was obtained.

Synthesis of Compound 7

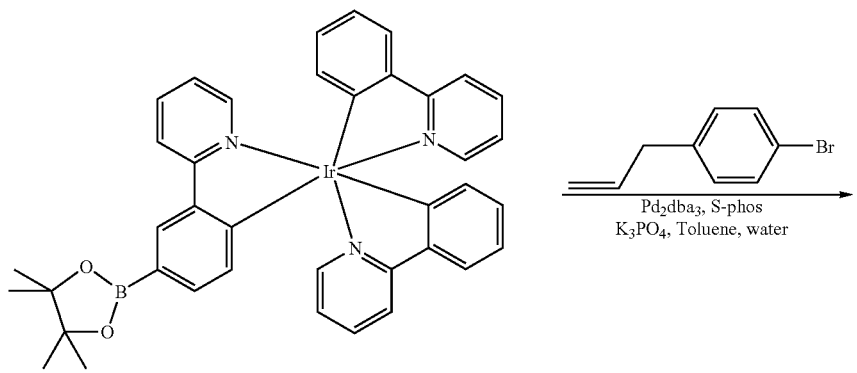

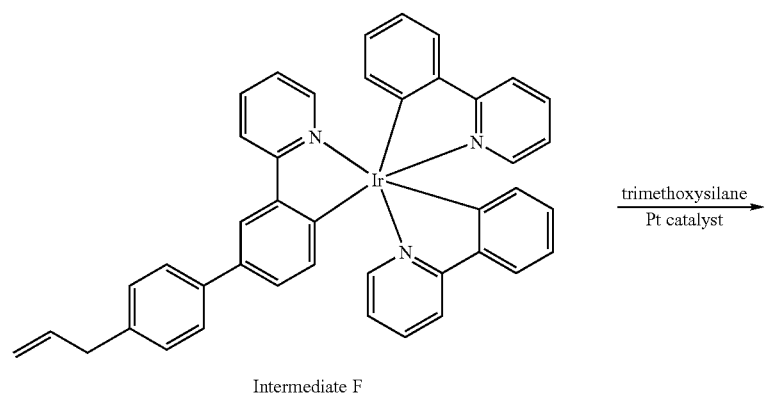

Intermediate F

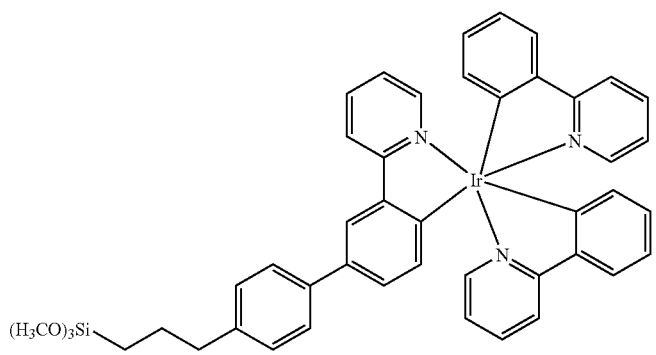

Compound 7

Intermediate F: 1.0 eq. of Irppy monoboronic ester, 1.2 eq of 1-allyl-4-bromobenzene, 0.08 eq. of S-phos, and 3 eq. of potassium phosphate are mixed in 4:1 toluene and water. The mixture is purged with nitrogen for 30 minutes. To the mixture is then added 0.02 eq. of $Pd_2(dba)_3$ under nitrogen. The mixture is heated up to reflux overnight and then worked up. The coupling product can be purified by column chromatography using a mixture of hexanes and dichloromethane as solvent.

Compound 7: 1.0 eq. of intermediate F, 3.0 eq. of trimethoxysiloxane, and 5% eq of PtO2 are mixed in anhydrous dichloromethane under nitrogen. The mixture is heated to reflux overnight. The catalyst is filtered off and the final product (Compound 7) can be precipitated from methanol.

Synthesis of Compound 8
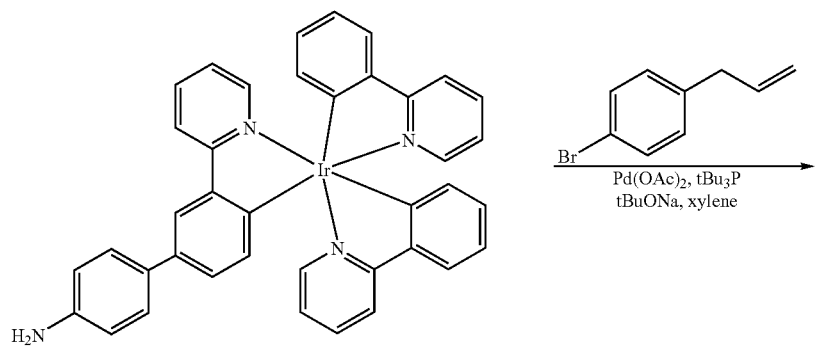
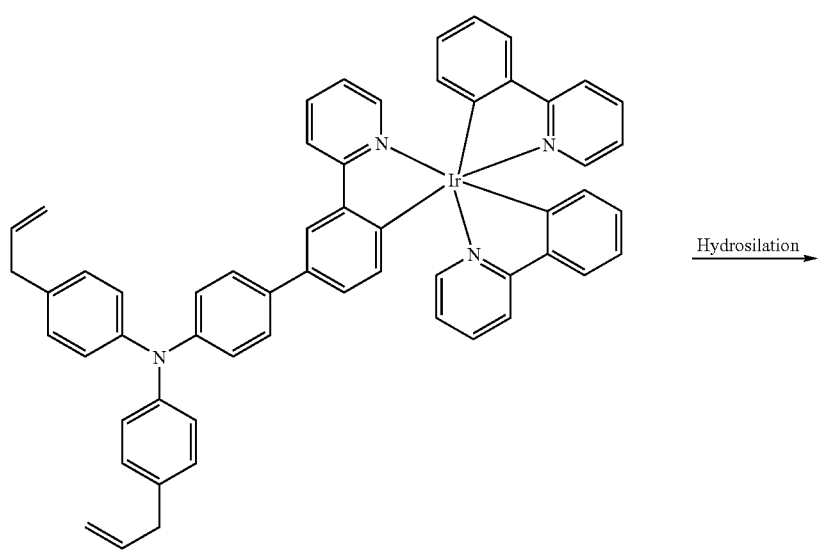
Intermediate G
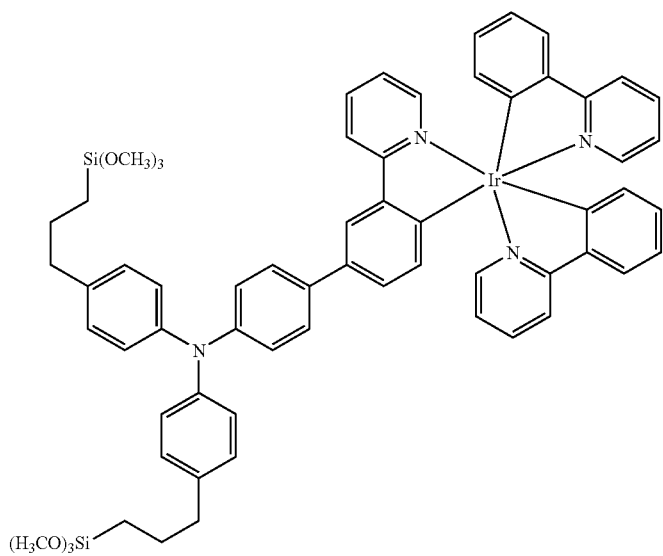
Compound 8

Intermediate G: 1.0 eq. of intermediate B, 2.2 eq. of 1-allyl-4-bromobenzene, 3 eq. of sodium t-butoxide, 3% eq. of palladium acetate, and 6% eq. of tBu$_3$P are mixed in anhydrous xylene under nitrogen. The mixture is then heated up to reflux for 6 hours. The product (intermediate G) can be isolated through column chromatography using a mixture of hexanes and dichloromethane as solvent.

Compound 8: 1.0 eq of intermediate F, 6.0 eq. of siloxane, and 10% eq. of PtO$_2$ are mixed in anhydrous dichloromethane under nitrogen. The mixture is heated to reflux overnight. The catalyst is filtered off and the final product (Compound 8) can be obtained by precipitating from methanol.

Synthesis of Compound 9

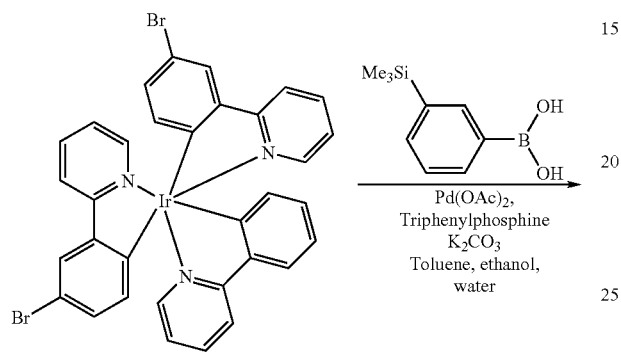

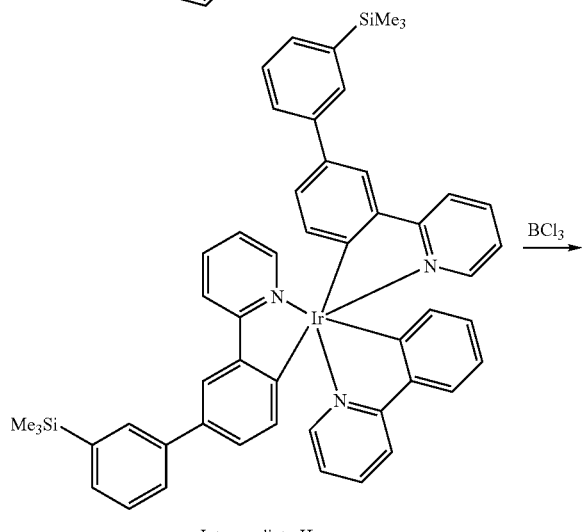

Intermediate H

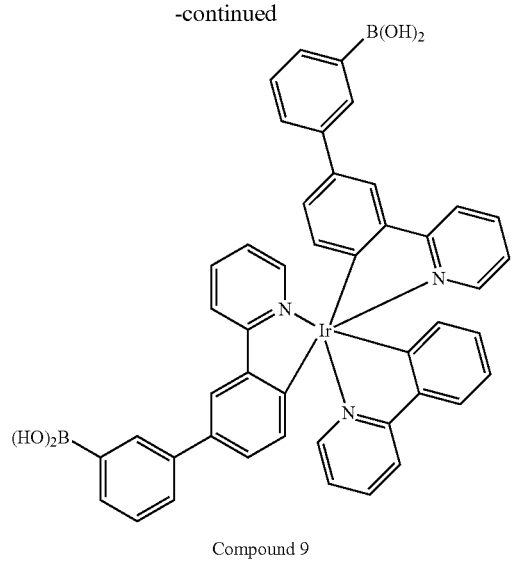

Compound 9

Intermediate H, 1.2 g of dibromo-Irppy, 0.86 g of 3-(trimethylsilyl)phenylboronic acid, 0.07 g of S-Phos, and 2.04 g of potassium phosphate were mixed with 250 mL of toluene and 50 mL of water. The system was purged with nitrogen for 30 minutes and 0.04 g of Pd$_2$(dba)$_3$ was added. The mixture was heated up to reflux overnight. After cooling to room temperature, the organic layer was separated. The product was purified by column chromatography using 2:3 dichloromethane/hexanes as solvent, yielding 0.9 g of desired product (intermediate H).

Compound 9: 0.87 g of intermediate H was dissolved in 50 mL of anhydrous dichloromethane and cooled to −78° C. To this solution was added 0.35 mL of BBr$_3$. The reaction mixture was warmed to room temperature slowly overnight. The reaction was quenched by methanol, and then water was added. The solution was extracted with ethyl acetate and washed with water. The product was then precipitated from hexanes. The precipitate was collected by filtration. The solid was again dissolved in ethyl acetate and precipitated from hexanes, yielding 0.2 g of product (Compound 9).

Synthesis of Compound 10

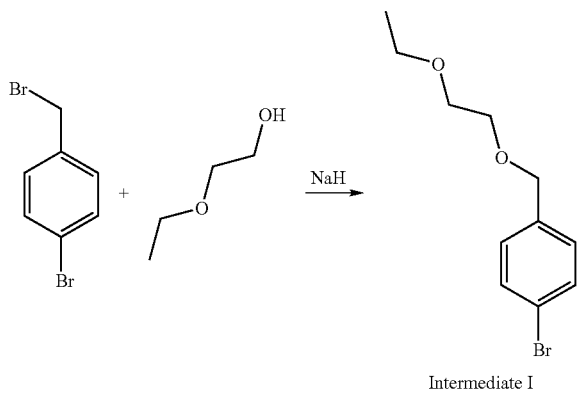

Intermediate I

-continued
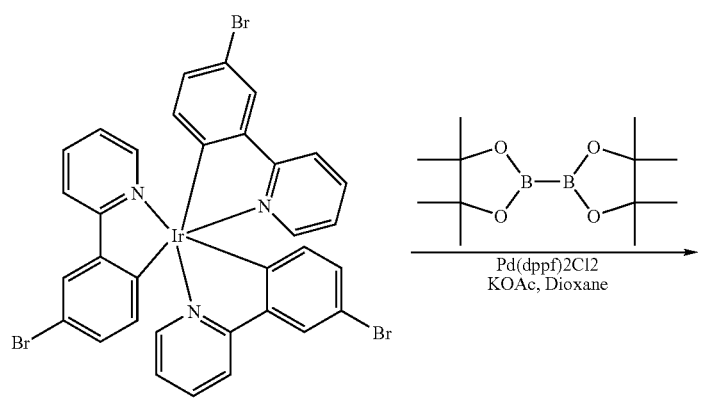
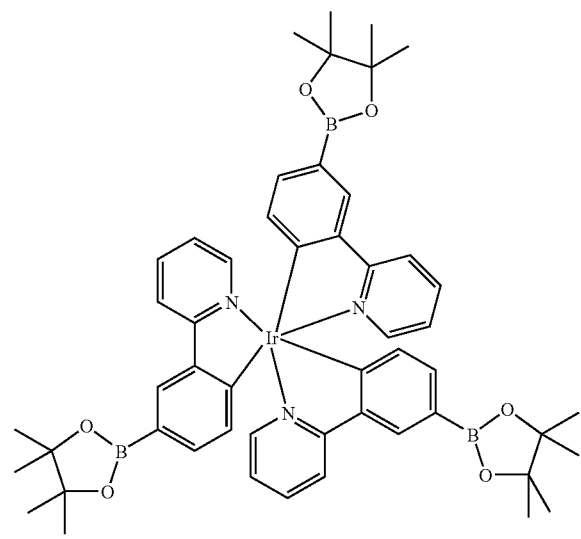
Intermediate J
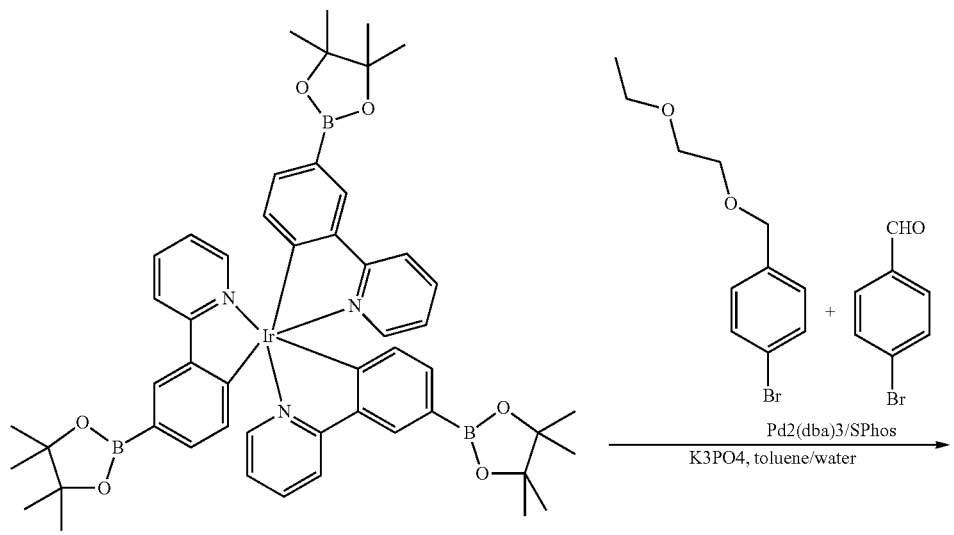

-continued
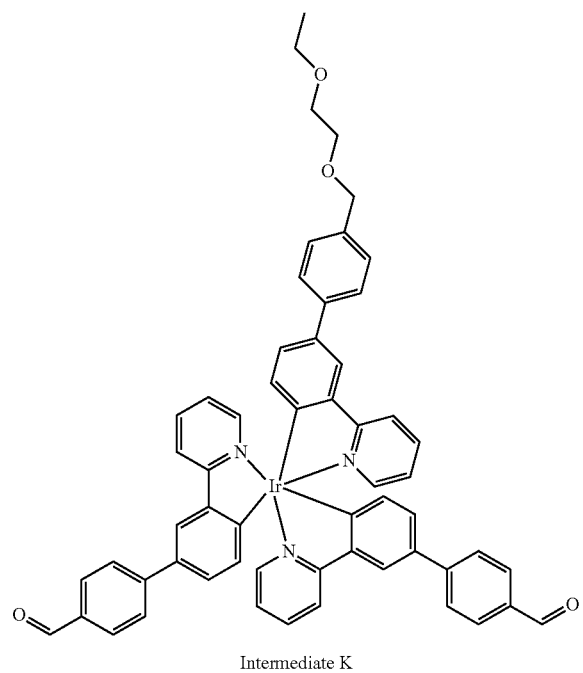
Intermediate K
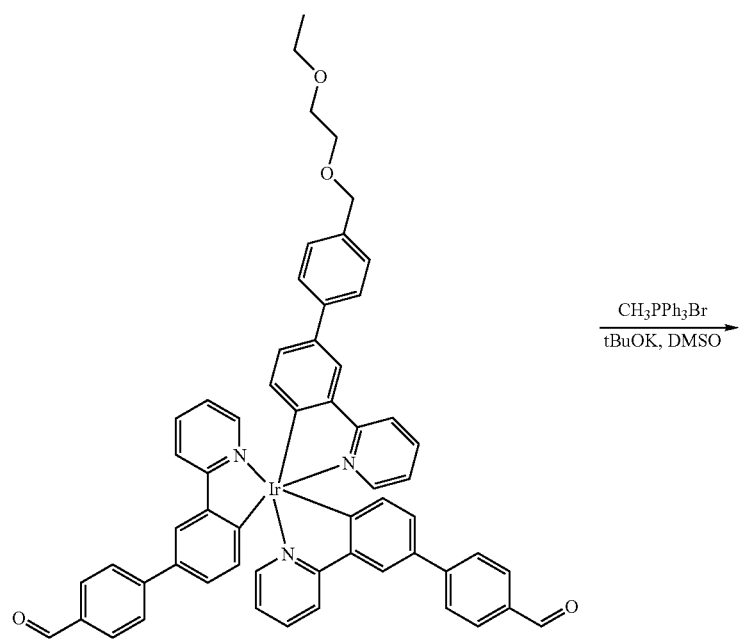
CH₃PPh₃Br / tBuOK, DMSO →

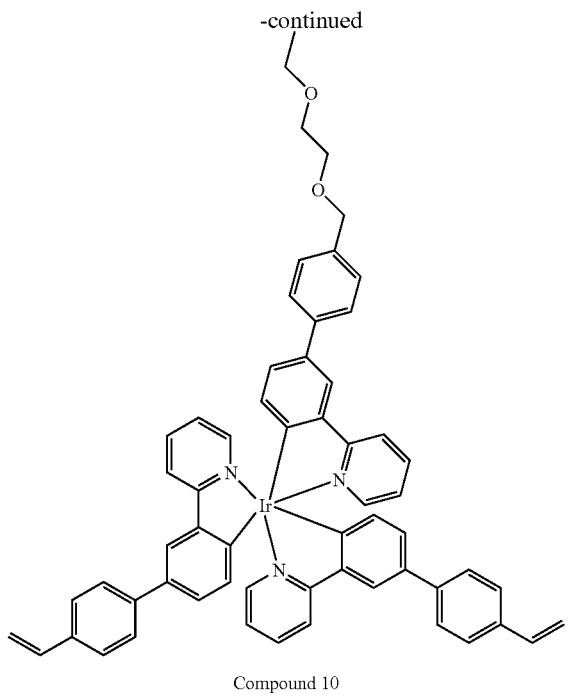

Compound 10

Intermediate I: 8.5 g of benzyl bromide and 10 mL 2-ethoxyethanol were weighed in a round bottom flask with 100 mL anhydrous THF solvent. The solution was cooled in an ice bath and 4 g of NaH was slowly added. The solution was warmed to room temperature and stirred overnight. Ethyl acetate was added to quench residual NaH. The solution was washed with water, dried with $MgSO_4$ and filtered. The solvent was removed by rotary evaporation. The intermediate was dry packed on celite and purified by column chromatography using hexanes/ethyl acetate as eluent.

Intermediate J: 1 equivalent of tris-5-bromophenylpyridine iridium, 5 equivalents bis(pinacolato)diboron, 0.09 equivalents of $Pd(dppf)_2Cl_2$, and 9 equivalents of potassium acetate were weighed in a flask with dioxane used as solvent. The solution was purged with nitrogen and heated to 90° C. for 12 hours. The dioxane was removed by rotary evaporation, the solid was dissolved in dichloromethane and washed with water. The dichloromethane was removed by rotary evaporation and the material was dry packed on celite and purified by column chromatography using hexanes/dichloromethane as eluent.

Intermediate K: 0.5 g (0.48 mmol) tris-(5-pinacolatoboron-phenylpyridine) iridium (intermediate J), 0.16 g (0.63 mmol) 4-bromobenzyl ether (intermediate I), 0.23 g (1.25 mmol) 4-bromobenzyaldehyde, 0.066 g (0.072 mmol) tris (dibenzylideneacetone)dipalladium(0) [$Pd_2(dba)_3$], 0.12 g (0.29 mmol) 2-dicyclohexylphosphino-2',6'-dimethoxybiphenyl (SPhos) and 0.92 g (4.32 mmol) potassium phosphate tribasic ($K_3PO_4$) were weighed into a flask. 80 mL toluene and 20 mL water were used as solvent and the solution was purged with nitrogen. The solution was heated to reflux for twelve hours. Upon cooling, the organic layer was separated, and dried with $MgSO_4$. The product was separated by column chromatography using dichlormethane/ethyl acetate as eluent (1% ethyl acetate gradient to 50%). The solvent was removed by rotary evaporation, and the product dried overnight under vacuum.

Compound 10: 0.3 g (0.28 mmol) Intermediate K and 0.51 g (1.4 mmol) methyltriphenylphosphonium bromide were added in a flask with 15 mL anhydrous DMSO under nitrogen. 1.4 mL (1.4 mmol) potassium tert-butoxide as a 1 molar solution in THF was added slowly by syringe. The solution was stirred at room temperature for 12 hours and water was added to precipitate the product. The solid was collected by filtration, dissolved in dichloromethane and dried with $MgSO_4$. The solvent was removed by rotary evaporation. The product was dry packed on celite and purified by column chromatography using hexanes/ethyl acetate (1:1) as eluent.

Synthesis of Compound 11
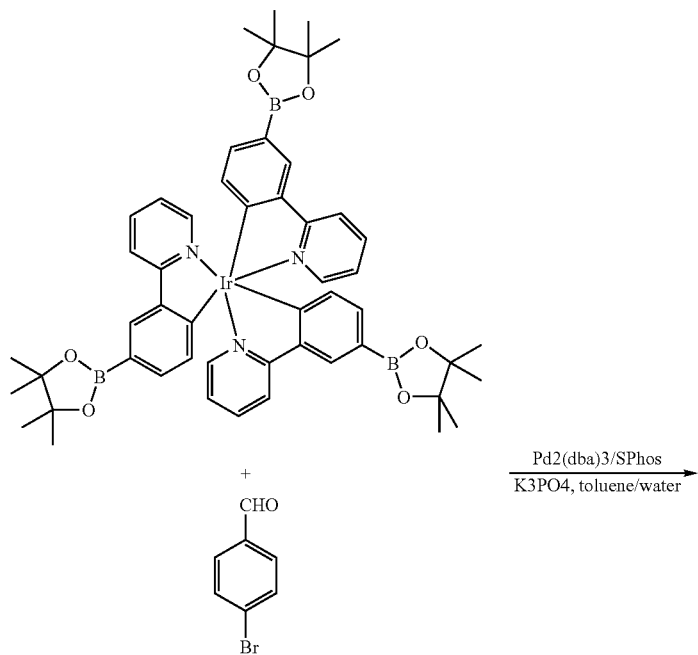
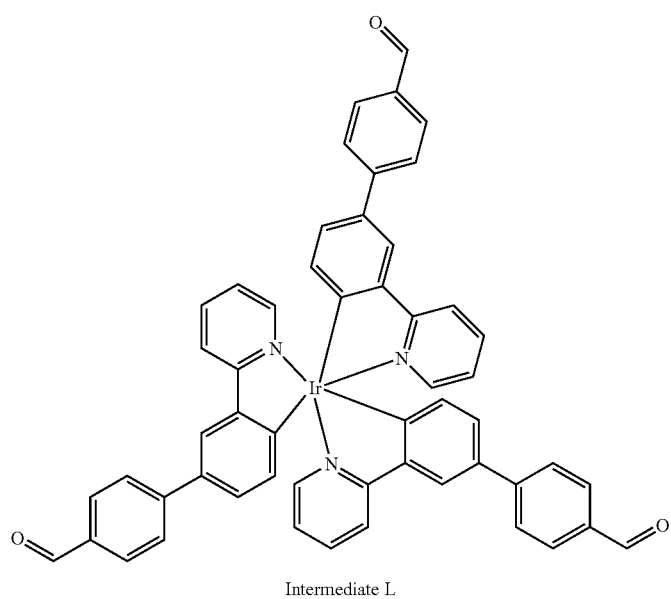
Intermediate L

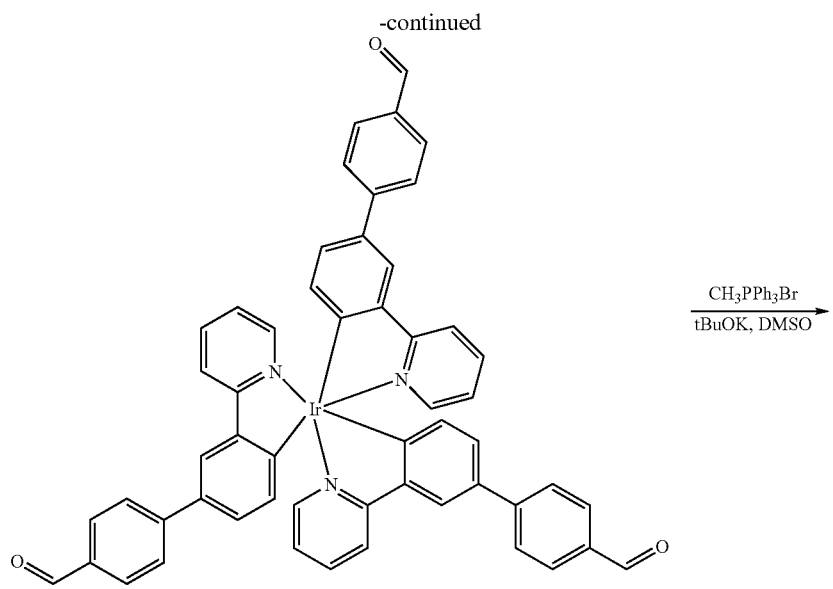

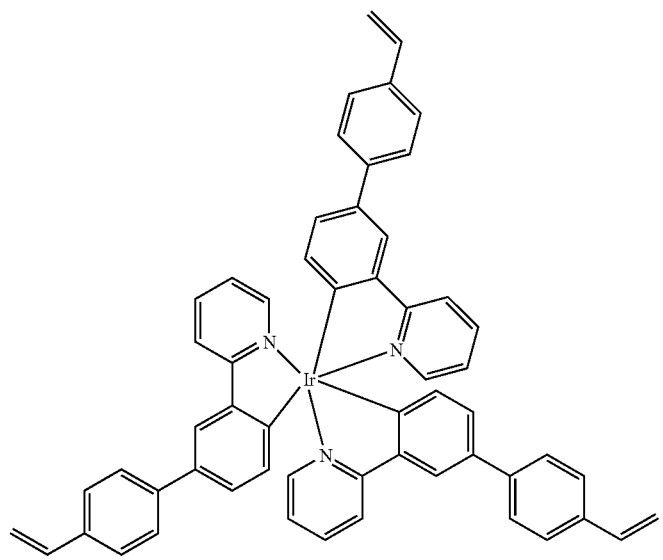

Compound 11

Intermediate L: 0.5 g (0.48 mmol) tris-(5-pinacolatoboronphenylpyridine) iridium (intermediate J), 0.46 g (2.5 mmol) 4-bromobenzyaldehyde, 0.066 g (0.072 mmol) tris(dibenzylideneacetone)dipalladium(0) [$Pd_2(dba)_3$], 0.12 g (0.29 mmol) 2-dicyclohexylphosphino-2',6'-dimethoxybiphenyl (SPhos) and 0.92 g (4.32 mmol) potassium phosphate tribasic ($K_3PO_4$) were weighed into a flask. 80 mL toluene and 20 mL water are used as solvent and the solution was purged with nitrogen. The solution was heated to reflux for twelve hours. Upon cooling, the organic layer was separated, and dried with $MgSO_4$. The product was separated by column chromatography using dichloromethane/ethyl acetate as eluent (1% ethyl acetate). The solvent was removed by rotary evaporation, and the product dried overnight under vacuum.

Compound 11: 0.2 g (0.21 mmol) Intermediate L and 0.37 g (1.03 mmol) methyltriphenylphosphonium bromide were added in a flask with 15 mL anhydrous DMSO. 1.03 mL (1.03 mmol) potassium tert-butoxide as a 1 molar solution is added slowly by syringe. The solution is stirred at room temperature for 12 hours and water is added to precipitate the product. The solid is collected by filtration, dissolved in dichloromethane and dried with $MgSO_4$. The solvent is removed by rotary evaporation. The product is dry packed on celite and purified by column chromatography using hexanes/toluene (1:0 to 1:4) as eluent.

Synthesis of Compound 12
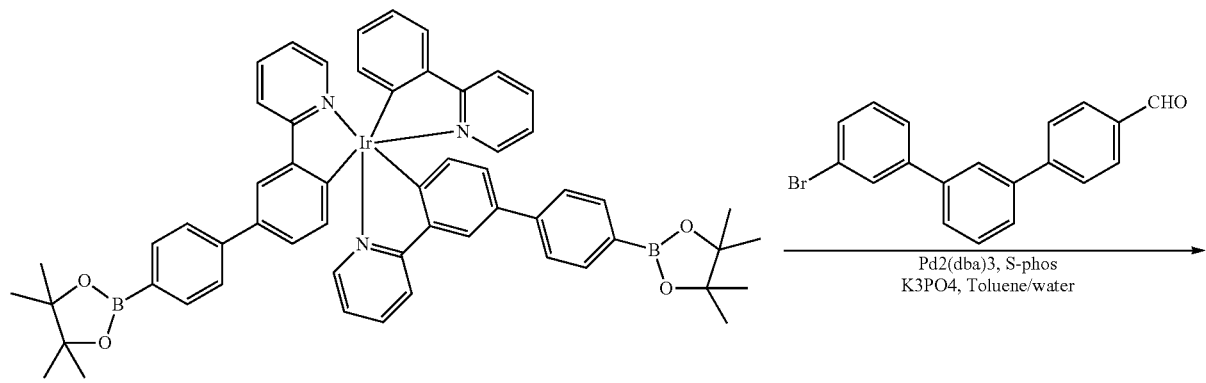
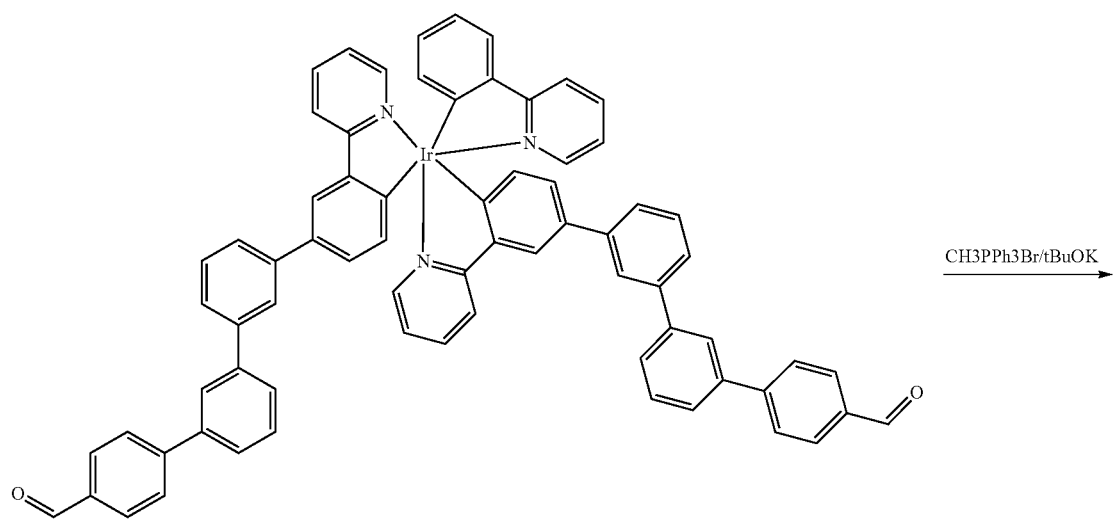
Intermediate M
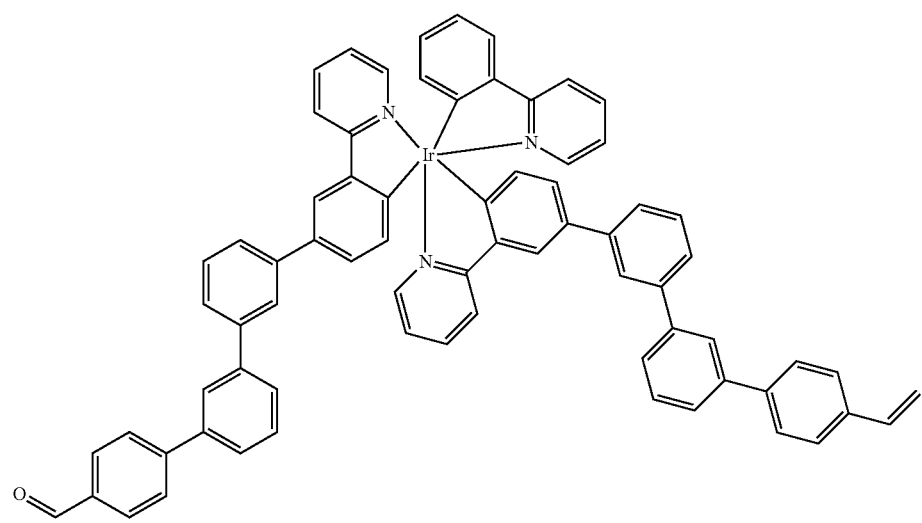
Compound 12

Intermediate M: 0.6 g (0.772 mmol) of boronic ester, 0.78 g (2.3 mmol) of aldehyde, 0.05 g (4 mol %) of S-phos, 1.1 g (4.6 mmol) of potassium phosphate, 100 ml of toluene, and 10 ml of water was added into a three-neck flask. The flask was purged with nitrogen for 20 minutes before adding 0.03 g of $Pd_2(dba)_3$. The mixture was heated up to reflux for 14 hours. After cooling to room temperature, the organic layer was separated and dried over magnesium sulfate. After evaporating solvent, the residue was purified by silica gel column using 1:4 dichloromethane/hexanes as eluent. 0.35 g of desired product was collected.

Compound 12: 0.25 g (0.21 mmol) of intermediate M and 0.23 g (0.64 mmol) of methyl triphenylphosphine bromide were dissolved in 20 ml of DMSO. To this solution was added 0.64 ml 1.0 M tBuOK in THF dropwise. The reaction was allowed to react overnight. Methanol was added to precipitate the product. The precipitate was collected by filtration. The product was purified by column using 3:1 toluene/hexanes. 0.12 g of pure product was collected after purification.

Synthesis of Compound 13

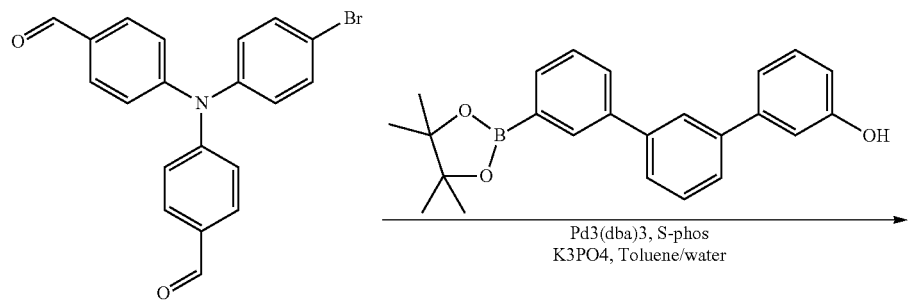

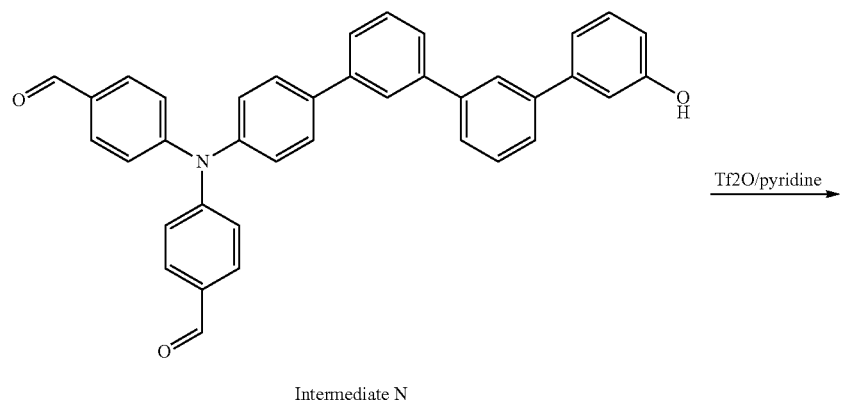

Intermediate N

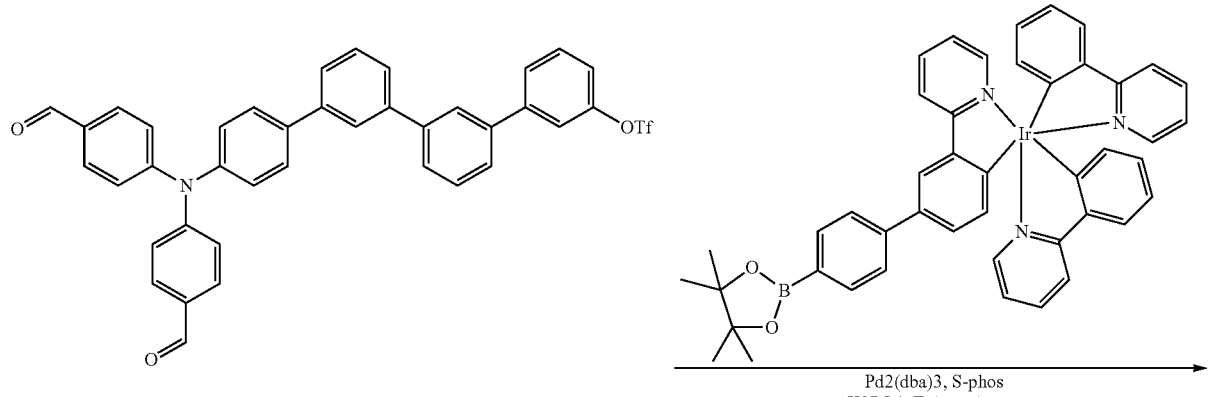

Intermediate O

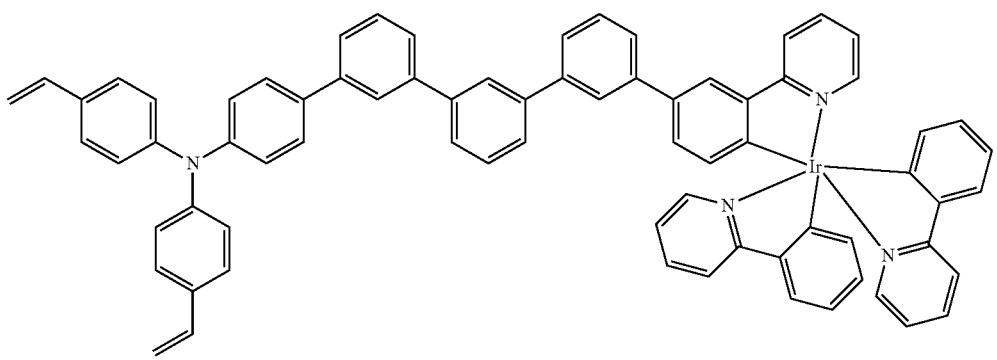

Intermediate P

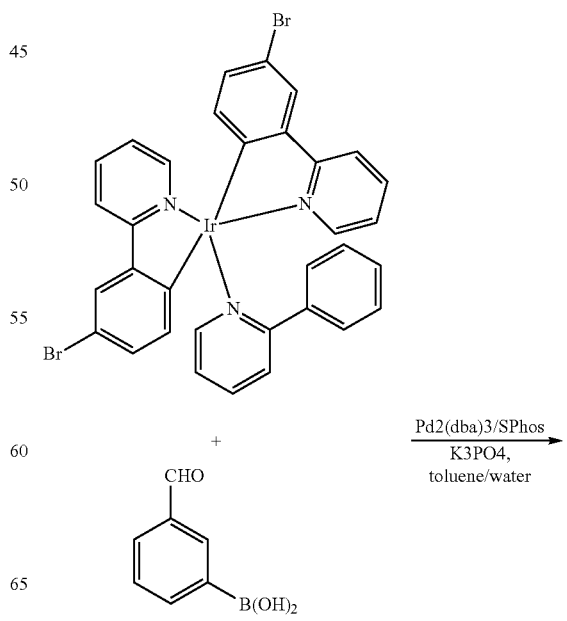

Compound 13

Intermediate N: 1.2 g (32 mmol) of 4,4'-(4-bromophenylazanediyl)dibenzaldehyde, 1.08 g (2.9 mmol) of boronic ester, 0.1 g (0.23 mmol) of S-phos, and 2.1 g (8.7 mmol) of potassium phosphate were mixed with 100 ml of toluene and 10 ml of water in a three-neck flask. The mixture was purged with nitrogen for 20 minutes. 0.05 g of $Pd_2(dba)_3$ was added to the mixture. The reaction was heated to reflux overnight. After cooling to room temperature, the organic layer was separated and dried with magnesium sulfate. The product was purified by column chromatography using 5% ethyl acetate in dichloromethane as eluent. 1.3 g of desired product was collected. (Yield: 82%)

Intermediate O: 1.25 g (2.3 mmol) of Intermediate N was dissolved in 50 ml of dichloromethane. 0.45 g (5.75 mmol) of pyridine was added. The solution was cooled with an ice-water bath. To the solution was added dropwise 0.46 ml (5.75 mmol) of triflic anhydride. The solution was reacted for 15 min at 0° C., then quenched with water. After purified with column using 2:1 dichloromethane/hexanes as eluent. 0.56 g product was collected.

Intermediate P: 0.56 g (0.83 mmol) Intermediate O, 0.63 g (0.69 mmol) of iridium boronic ester, 0.012 g (0.014 mmol) $Pd_2(dba)_3$, 0.023 g (0,056 mmol) of S-phos, 0.48 g of $K_3PO_4$, 50 ml of toluene and 5 ml of water were reacted the same manner as Intermediate N. The product was purified by column chromatography using dichloromethane as eluent. 0.75 g (92% yield) of desired product was isolated.

Compound 13: 0.65 g (0.55 mmol) intermediate P and 0.69 g (1.92 mmol) $MePPh_3Br$ were dissolved in 30 ml of DMSO. To this solution was added dropwise 1.65 ml of 1.0 M tBuOK. After stirring overnight at room temperature, the product was precipitated from 100 ml of methanol. The product was purified by column chromatography using 2:1 toluene/hexanes. 0.26 g (40% yield) of desired product was isolated.

Synthesis of Compound 14

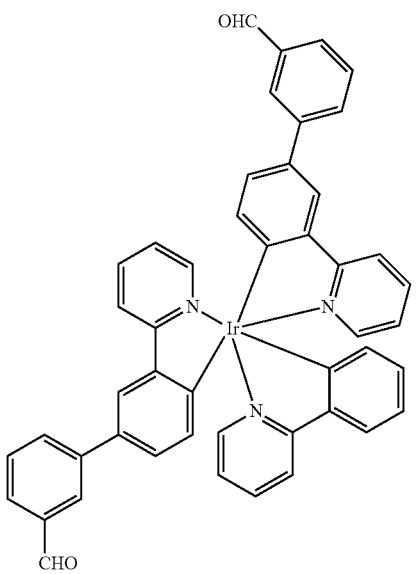

Intermediate Q

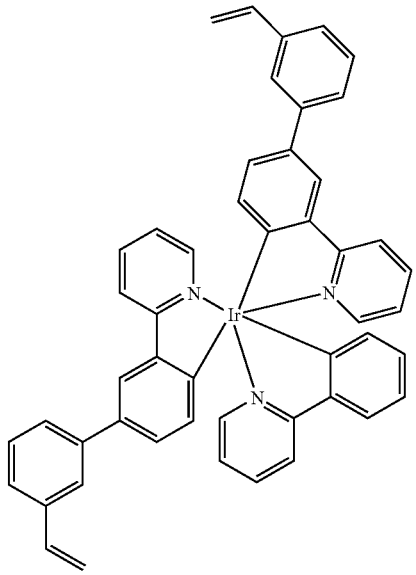

Compound 14

Intermediate Q: 1 g (1.23 mmol) bis(5-bromo-2-phenylpyridine)-2-phenylpyridine iridium, 0.75 g (4.9 mmol) 3-formylphenylboronic acid, 0.11 g (0.123 mmol) tris(dibenzylideneacetone)dipalladium(0) [Pd$_2$(dba)$_3$], 0.2 g (0.49 mmol) 2-dicyclohexylphosphino-2',6'-dimethoxybiphenyl (SPhos) and 1.6 g (7.4 mmol) potassium phosphate tribasic (K$_3$PO$_4$) were weighed into a flask. 80 mL toluene and 20 mL water were used as solvent and the solution was purged with nitrogen. The solution was heated to reflux for twelve hours. Upon cooling, the organic layer was separated, and dried with MgSO$_4$. The product was separated by column chromatography using dichloromethane/ethyl acetate as eluent (1% ethyl acetate). The solvent was removed by rotary evaporation, and the product dried overnight under vacuum.

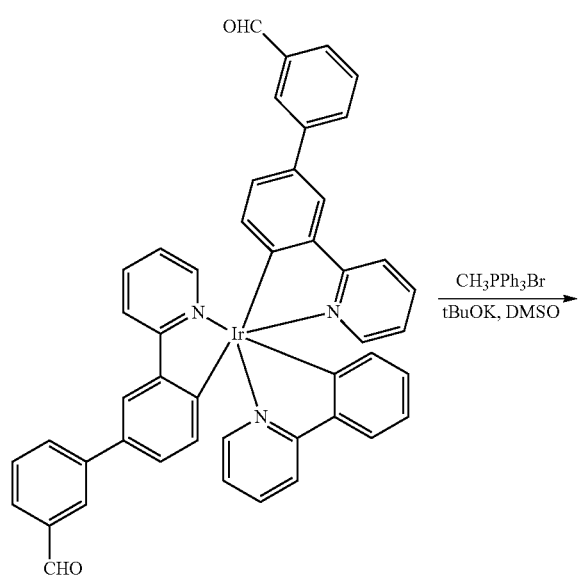

CH$_3$PPh$_3$Br
tBuOK, DMSO

Compound 14: 0.6 g (0.69 mmol) Intermediate Q and 1.24 g (3.5 mmol) methyltriphenylphosphonium bromide were added in a flask with 35 mL anhydrous DMSO. 3.5 mL (3.5 mmol) potassium tert-butoxide as a 1 molar solution was added slowly by syringe. The solution was stirred at room temperature for 12 hours and water was added to precipitate the product. The solid was collected by filtration, dissolved in dichloromethane and dried with MgSO$_4$. The solvent was removed by rotary evaporation. The product was dry packed on celite and purified by column chromatography using hexanes/toluene (1:0 to 1:4) as eluent.

Synthesis of Compound 15

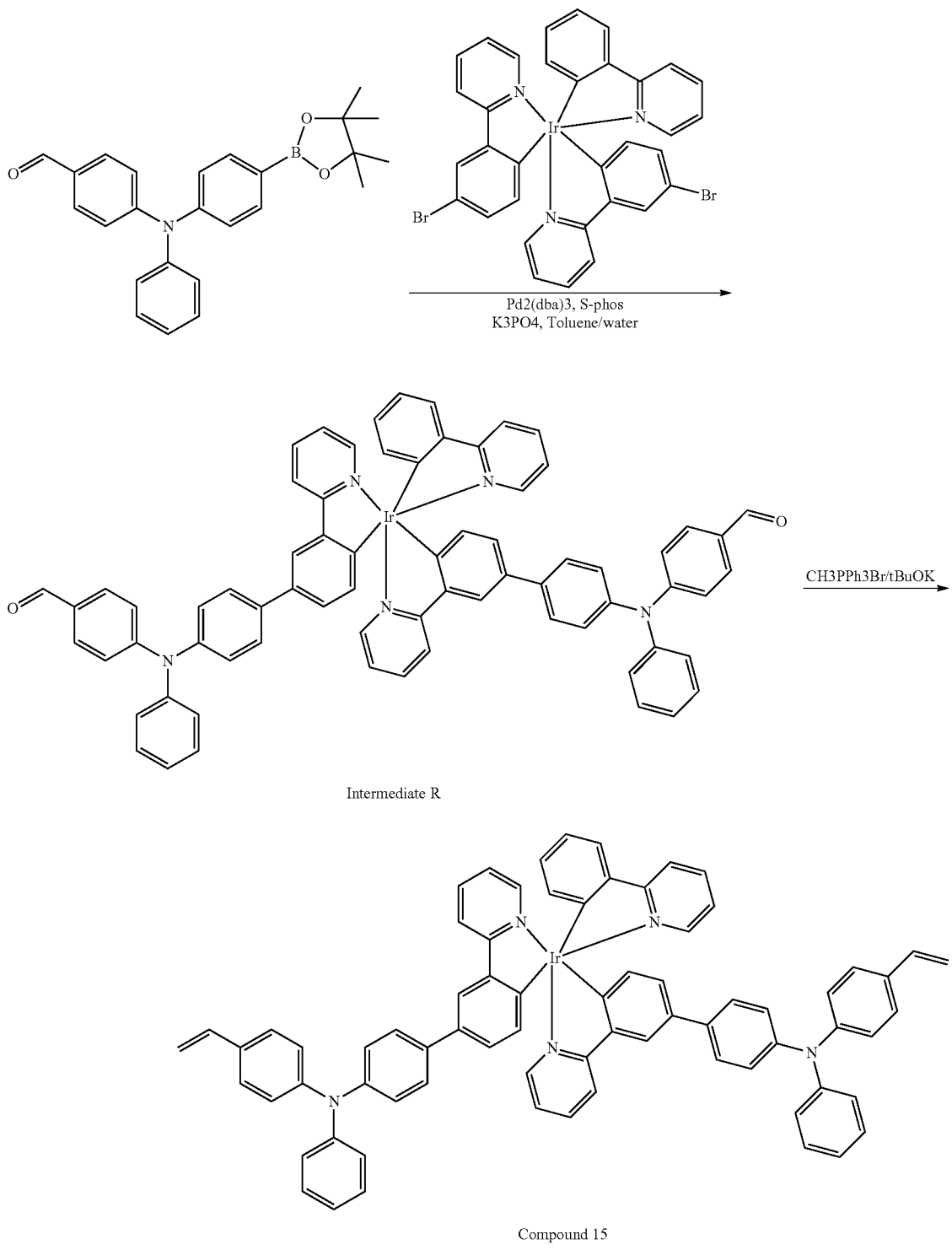

Intermediate R: 2.6 g of boronic ester (6.46 mmol), 1.75 g (2.15 mmol) of dibromo(Irppy), 0.079 g (0.086 mmol) of Pd$_2$(dba)$_3$, 0.15 g (0.344 mmol) S-Phos, and 3.0 g (12.9 mmol) of K$_3$PO$_4$ in 300 ml toluene and 30 ml water were reacted the same manner as Intermediate Q. The product was purified by column chromatography using dichloromethane as eluent. 1.2 g (60% yield) of desired product was isolated.

Compound 15: 1 g (0.84 mmol) of Intermediate R and 1.0 g (2.9 mmol) of methyl triphenylphosphonium bromide were dissolved in 40 ml of DMSO. To this solution was added dropwise 2.5 ml of 1.0 M tBuOK. The product was precipitated from methanol. The product was purified by column chromatography using 2:1 toluene/hexanes as eluent. 0.75 g (75% yield) of desired product was isolated.

Synthesis of Compound 16
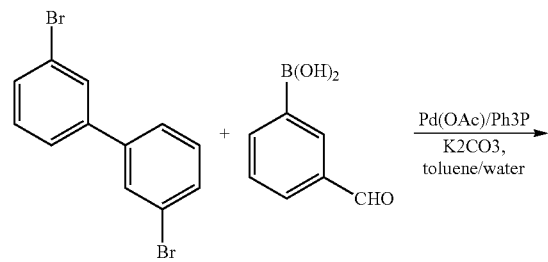
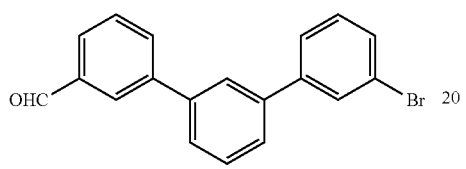
Intermediate S
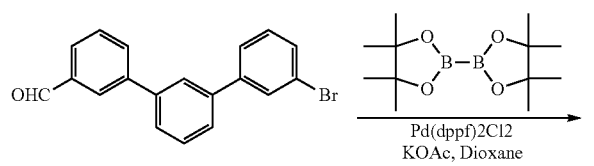
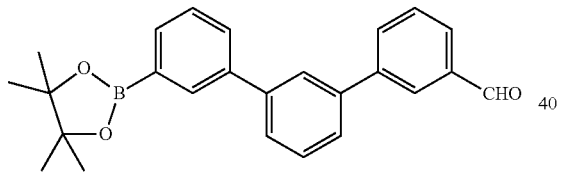
Intermediate T
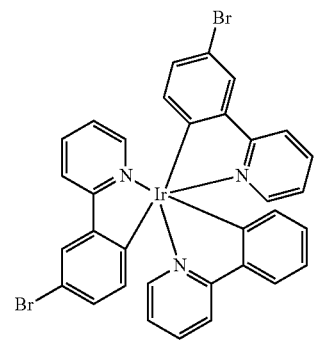
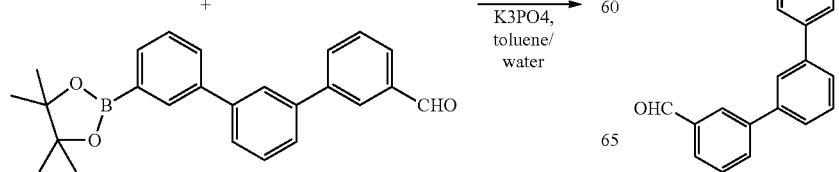
-continued
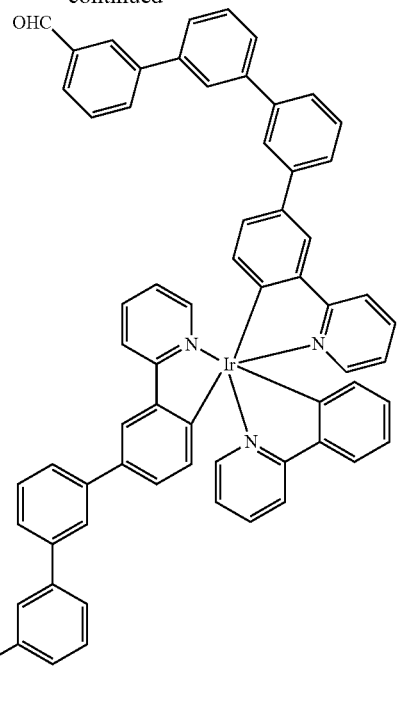
Intermediate U

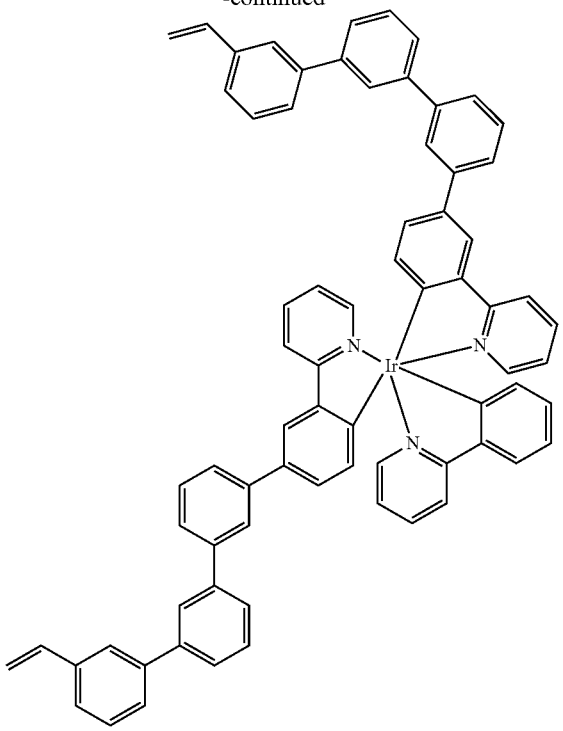

Compound 16

Intermediate S: 2 g (6.4 mmol) 3,3'-dibromobiphenyl, 0.96 g (6.4 mmol) 3-formylphenyl boronic acid, 0.072 g (0.32 mmol) palladium acetate, 0.34 g (1.28 mmol) triphenylphosphine and 2.65 g (19.2 mmol) potassium carbonate were weighed into a flask with 80 mL toluene and 20 mL water as solvent. The solution was purged with nitrogen. The solution was heated to reflux for twelve hours. Upon cooling, the organic layer was separated, and dried with MgSO$_4$. The product was separated by column chromatography using hexanes/ethylacetate as eluent (5% ethyl acetate).

Intermediate T: 2.5 g (7.4 mmol) 3-bromo-meta-terphenylaldehyde (intermediate S), 1.9 g (7.4 mmol) bis(pinacolato)diboron, 0.18 g (0.22 mmol) Pd(dppf)$_2$Cl$_2$, and 2.17 g (22.2 mmol) of potassium acetate were weighed in a flask with anhydrous dioxane used as solvent. The solution was purged with nitrogen and heated to 80° C. for 12 hours. The dioxane was removed by rotary evaporation, the solid was dissolved in dichloromethane and washed with water. The solution was dried with MgSO$_4$, the solvent was removed by rotary evaporation and the material was dry packed on celite and purified by column chromatography using hexanes/ethyl acetate as eluent.

Intermediate U: 1.25 g (1.56 mmol) bis(5-bromo-2-phenylpyridine)-2-phenylpyridine iridium, 2.4 g (6.25 mmol) 3-pinacolatoboron-meta-terphenylaldehyde (intermediate T), 0.14 g (0.156 mmol) tris(dibenzylideneacetone)dipalladium(0) [Pd$_2$(dba)$_3$], 0.25 g (0.62 mmol) 2-dicyclohexylphosphino-2',6'-dimethoxybiphenyl (SPhos) and 2 g (9.36 mmol) potassium phosphate tribasic (K$_3$PO$_4$) were weighed into a flask. 80 mL toluene and 20 mL water were used as solvent and the solution was purged with nitrogen. The solution was heated to reflux for twelve hours. Upon cooling, the organic layer was separated, and dried with MgSO$_4$. The product was separated by column chromatography using dichloromethane/ethyl acetate as eluent (2% ethyl acetate). The solvent was removed by rotary evaporation, and the product dried overnight under vacuum.

Compound 16: 1.3 g (1.11 mmol) Intermediate U and 2.0 g (5.56 mmol) methyltriphenylphosphonium bromide were added in a flask with 40 mL anhydrous DMSO. 5.56 mL (5.56 mmol) potassium tert-butoxide as a 1 molar solution was added slowly by syringe. The solution was stirred at room temperature for 12 hours and methanol was added to precipitate the product. The solid was collected by filtration, dissolved in dichloromethane and dried with MgSO$_4$. The solvent was removed by rotary evaporation. The product was dry packed on celite and purified by column chromatography using hexanes/toluene (1:0 to 1:4) as eluent.

Synthesis of Compound 17

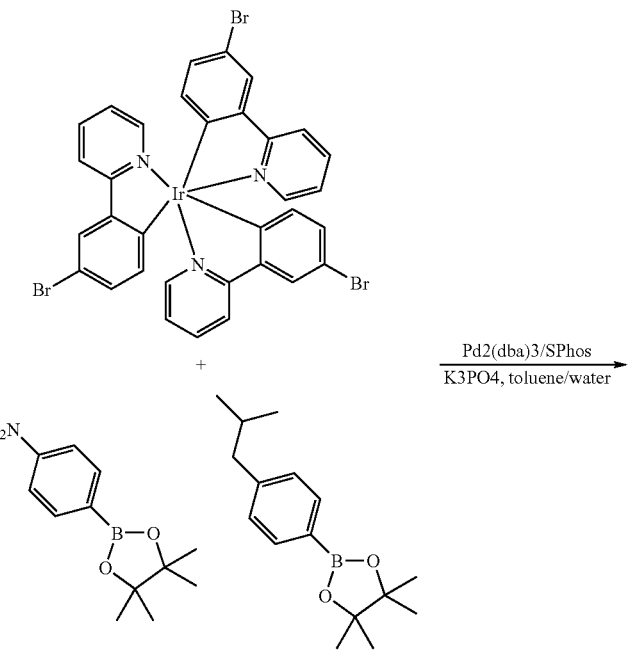

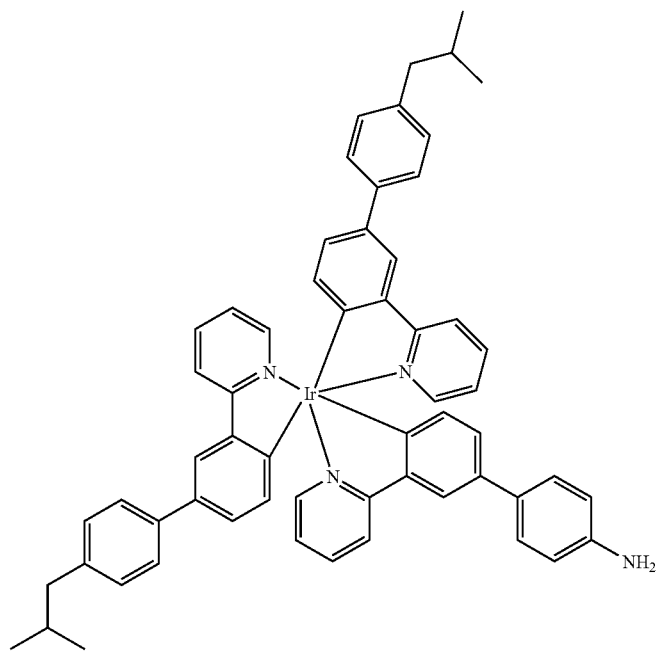
Intermediate V
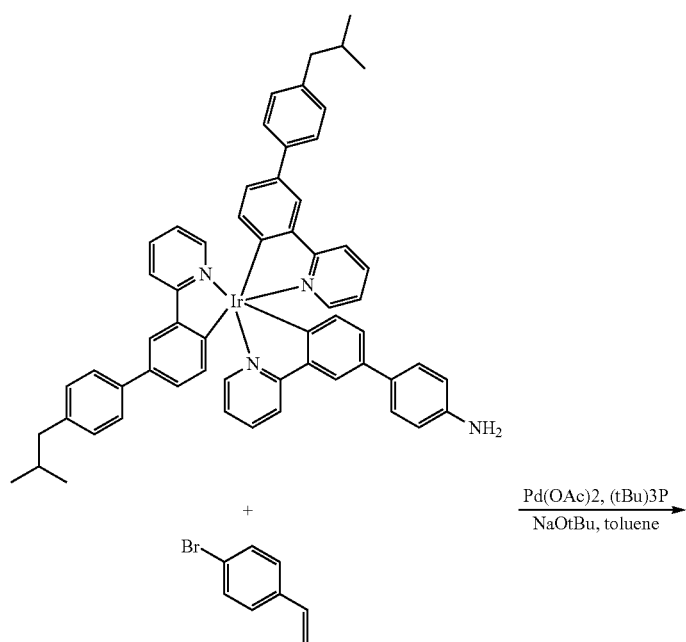

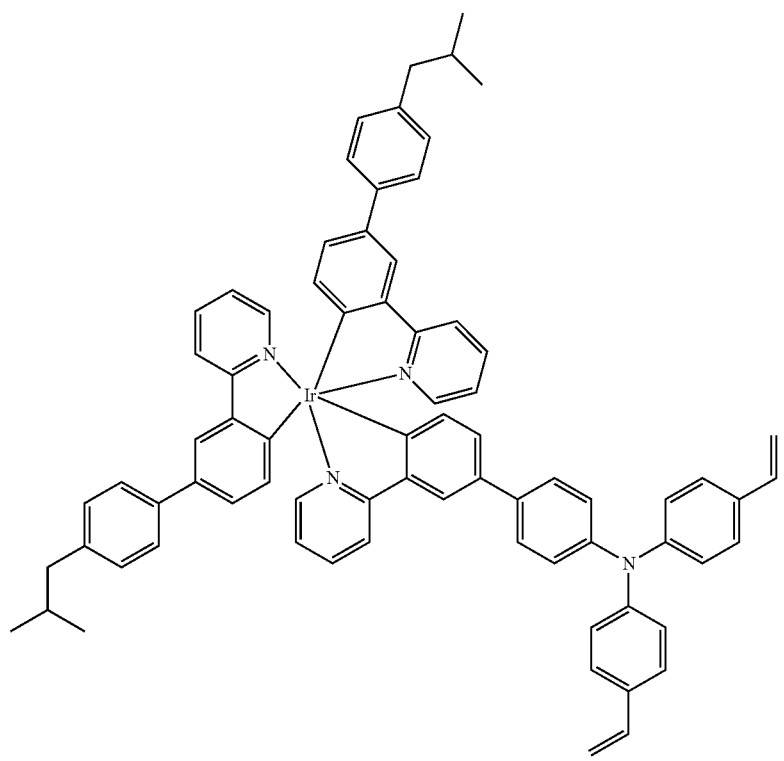

Compound 17

Intermediate V: 2.0 g (2.24 mmol) tris-5-bromophenylpyridine iridium complex, 0.65 g (2.99 mmol) 4-(4,4,5,5-tetramethyl-1,3,2-dioxaborolan-2-yl)aniline, 1.56 g (5.98 mmol) 2-(4-isobutylphenyl)-4,4,5,5-tetramethyl-1,3,2-dioxaborolane, 0.31 g (0.33 mmol) tris(dibenzylideneacetone)dipalladium(0) [Pd$_2$(dba)$_3$], 0.55 g (1.34 mmol) 2-dicyclohexylphosphino-2',6'-dimethoxybiphenyl (SPhos) and 2.4 g (11.2 mmol) potassium phosphate tribasic (K$_3$PO$_4$) were weighed into a flask. 80 mL toluene and 20 mL water were used as solvent and the solution was purged with nitrogen. The solution was heated to reflux for twelve hours. Upon cooling, the organic layer was separated, and dried with MgSO$_4$. The product was separated by column chromatography using dichloromethane. The solvent was removed by rotary evaporation.

Compound 17: 0.0043 g (0.019 mmol) palladium acetate and 38 μL (0.038 mmol) tri-t-butylphosphine (tBu)$_3$P as a 1 M solution in toluene solution were combined in 2 mL toluene and stirred 30 minutes. 0.64 g (0.63 mmol) intermediate V, 149 μL (1.14 mmol) 4-bromostyrene, 0.18 g (1.9 mmol) sodium t-butoxide (NaOtBu) were added with an additional 6 mL toluene. The solution was refluxed 4 hours under nitrogen. The product was precipitated with methanol, filtered and washed with methanol. The product was dry packed on celite and purified by column chromatography using hexanes/toluene (1:0 to 1:4) as eluent.

Synthesis of Compound 18: Compound 18 can be synthesized through the following scheme:

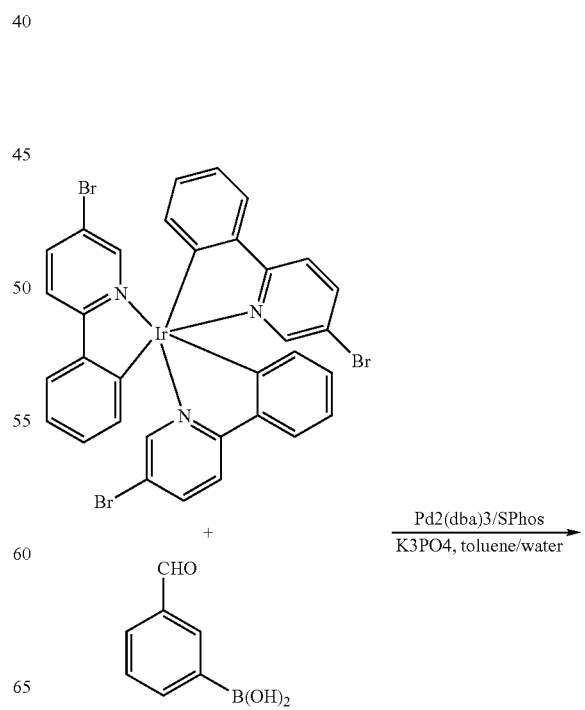

-continued

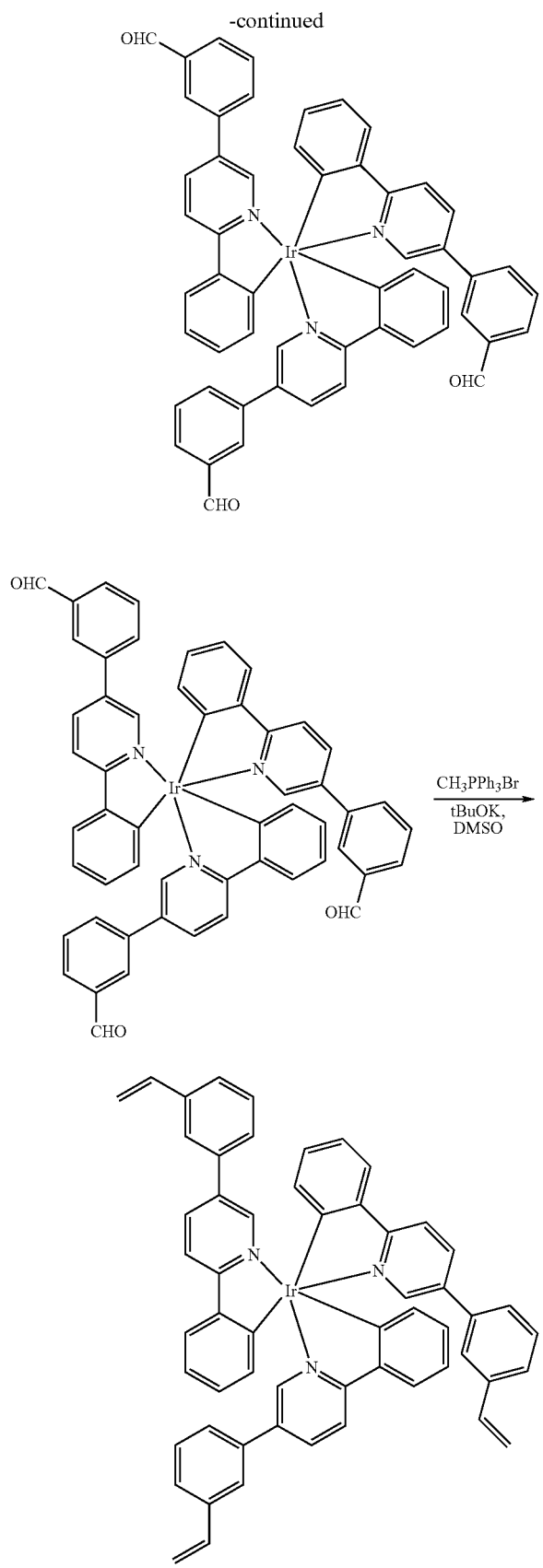

Compound 18

DEVICE EXAMPLES

Figure 3:
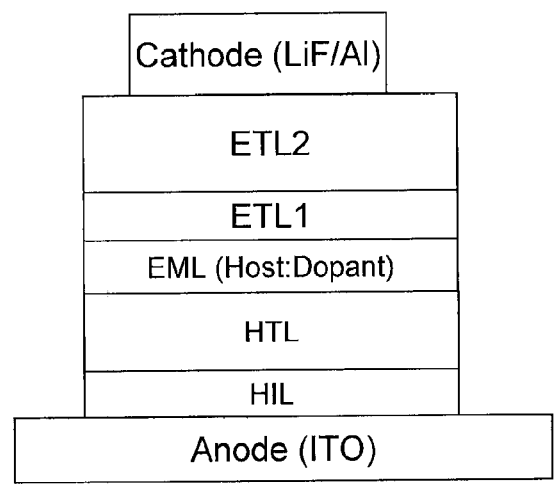
FIG. 3 shows the architecture used in the devices of both Example 1 and Comparative Example 1.

All example organic light-emitting devices were fabricated using spin-coating and vacuum thermal evaporation, and have the architecture shown in FIG. 3. The devices were fabricated on a glass substrate precoated with a 120 nm thick anode of indium tin oxide (ITO). The cathode was a 0.7 nm layer of LiF followed by 100 nm of aluminum. All devices were encapsulated with a glass lid sealed with an epoxy resin under nitrogen (<1 ppm $H_2O$ and $O_2$) immediately after fabrication, and a moisture getter was incorporated inside each device.

For the device of Comparative Example 1, the organic stack was fabricated to consist of PEDOT/PSS as a hole injection layer (HIL); $N^4,N^{4'}$-di(naphthalen-1-yl)-$N^4,N^{4'}$-bis(4-vinylphenyl)biphenyl-4,4'-diamine as a hole transport layer (HTL) at a thickness of 30 nm; 3,5-di(9H-carbazol-9-yl)biphenyl doped with tris(2-(biphenyl-3-yl)-4-tert-butylpyridine)iridium(III) as the emissive layer at a thickness of 30 nm; BAlq [aluminum(III) bis(2-methyl-8-hydroxyquinolinato)4-phenylphenolate] as a first electron transport layer (ETL 1) at a thickness of 10 nm; and $Alq_3$ [8-tris-hydroxyquinoline aluminum] as a second electron transport layer (ETL2) at a thickness of 40 nm.

The PEDOT/PSS layer, hole transport layer, and the emissive layer were deposited by spin coating. For the PEDOT/PSS layer, the solution was spin-coated onto ITO at 4000 rpm for 30 seconds. The film was baked at 200° C. for 10 minutes and then taken into a glovebox. For the hole transport layer, a 1.0 wt % solution of $N^4N^{4'}$-di(naphthalen-1-yl)-$N^4,N^{4'}$-bis(4-vinylphenyl)biphenyl-4,4'-diamine in toluene was spin-coated onto the hole injection layer at 2000 rpm for 30 seconds. The film was then baked at 170° C. for 30 minutes on a hot plate in a glovebox. The film became insoluble after baking. After cooling to room temperature, the emissive layer was deposited by spin-coating a solution of 1.0 wt % Host-1 and dopant Green-1 (host to dopant ratio of 88:12) onto the hole transport layer at 1000 rpm for 30 seconds. The emissive layer was then baked at 100° C. for one hour. The other layers were deposited by vacuum thermal evaporation.

The device of Example 1 was fabricated in a manner similar to the device of Comparative Example 1. The hole injection layer was spin-coated from a 0.5 wt % solution of Compound 1 in cyclohexanone at 4000 rpm for 30 seconds. For the hole transport layer, a 1.0 wt % solution of $N^4,N^{4'}$-di(naphthalen-1-yl)-$N^4,N^{4'}$-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % Host-1 and dopant Green-1 (host to dopant ratio of 88:12) onto the hole transport layer at 1000 rpm for 30 seconds. The emissive layer was then baked at 100° C. for one hour. The other layers were deposited by vacuum thermal evaporation.

The devices of Example 1 and Comparative Example 1 were operated under a DC current producing an initial brightness of 1000 $cd/m^2$. Device lifetime is defined here as the time elapsed for decay of brightness to 80% of the initial level, at room temperature under constant DC drive. The lifetime of the device using PEDOT/PSS in the hole injection layer (Comparative Example 1) was 46 hours, as compared to more than 1000 hours for the device using Compound 1 in the hole injection layer (Example 1). Table 1 below summarizes the composition and performance characteristics of the example devices.

TABLE 1

|  | Example 1 | Comparative Example 1 |
| --- | --- | --- |
| Hole injection layer | Compound 1 | PEDOT/PSS |
| Hole transporting layer | HTL-1 | HTL-1 |
| Emissive layer | Host-1:Green-1 (88:12) | Host-1:Green-1 (88:12) |
| Voltage (V) at 1000 cd/m$^2$ | 13.4 | 10.5 |
| Luminous efficiency (cd/A) at 1000 cd/m$^2$ | 15.3 | 29.5 |
| L 80% (hrs) at L$_0$ = 1000 cd/m$^2$ | >1000 | 46 |

Figure 4:
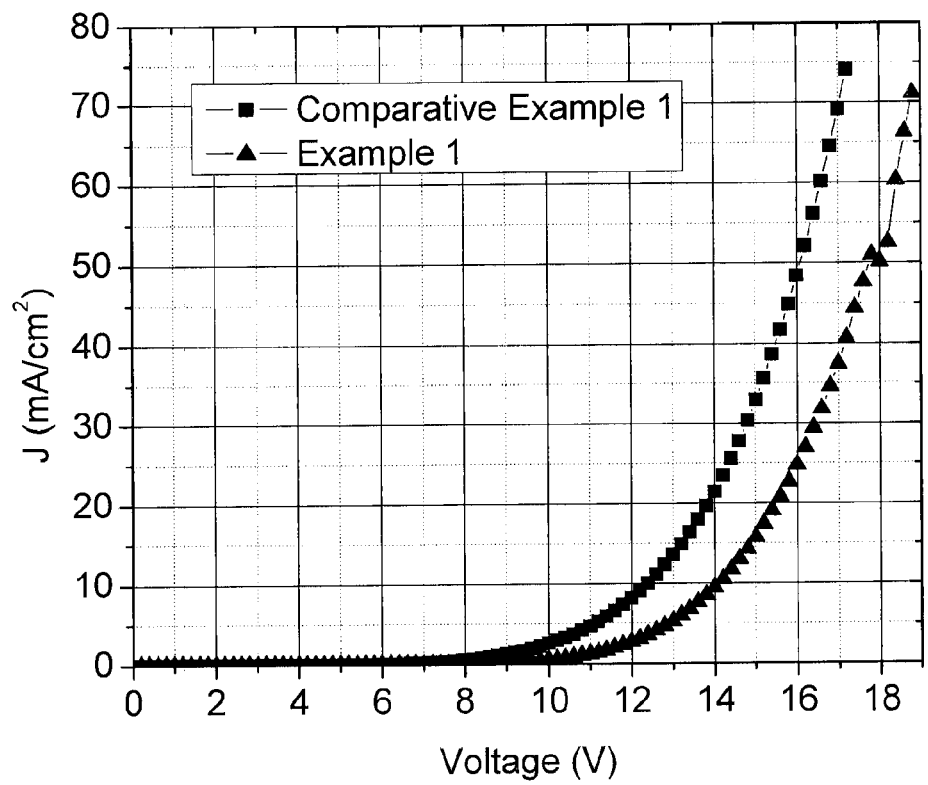
FIG. 4 shows a plot of current density as a function of voltage for the devices of Example 1 and Comparative Example 1.
Figure 5:
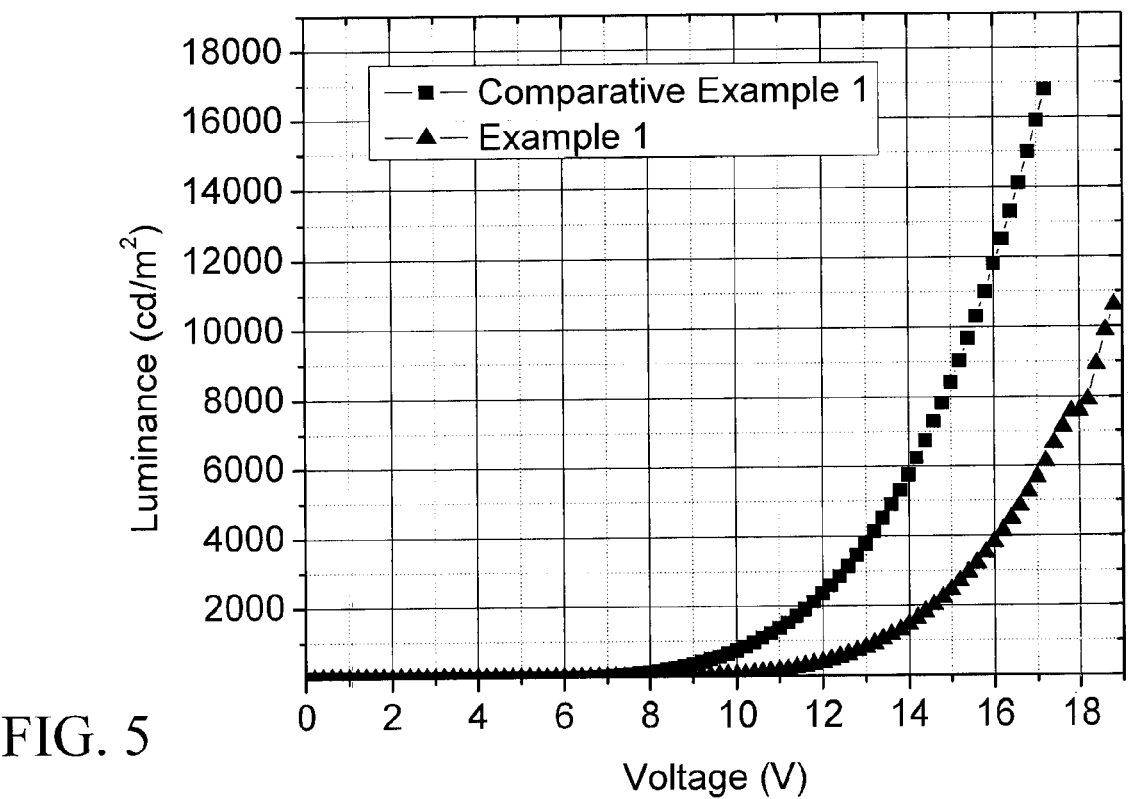
FIG. 5 shows a plot of luminance as a function of voltage for the devices of Example 1 and Comparative Example 1.
Figure 6:
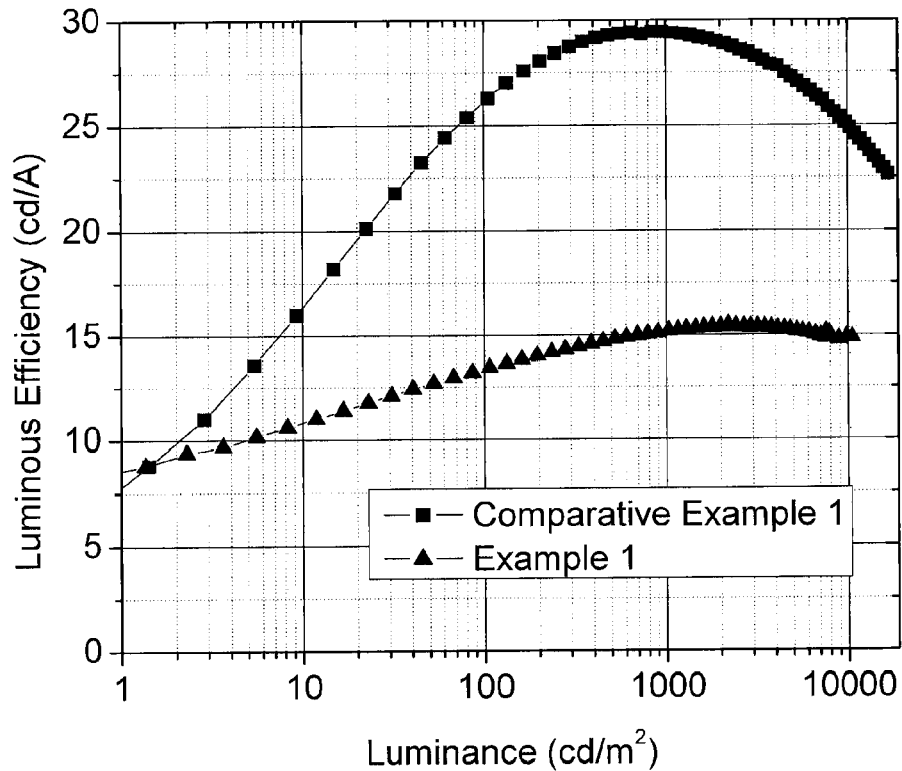
FIG. 6 shows the current efficiencies of the devices of Example 1 and Comparative Example 1, depicted as a plot of luminous efficiency versus luminance.
Figure 7:
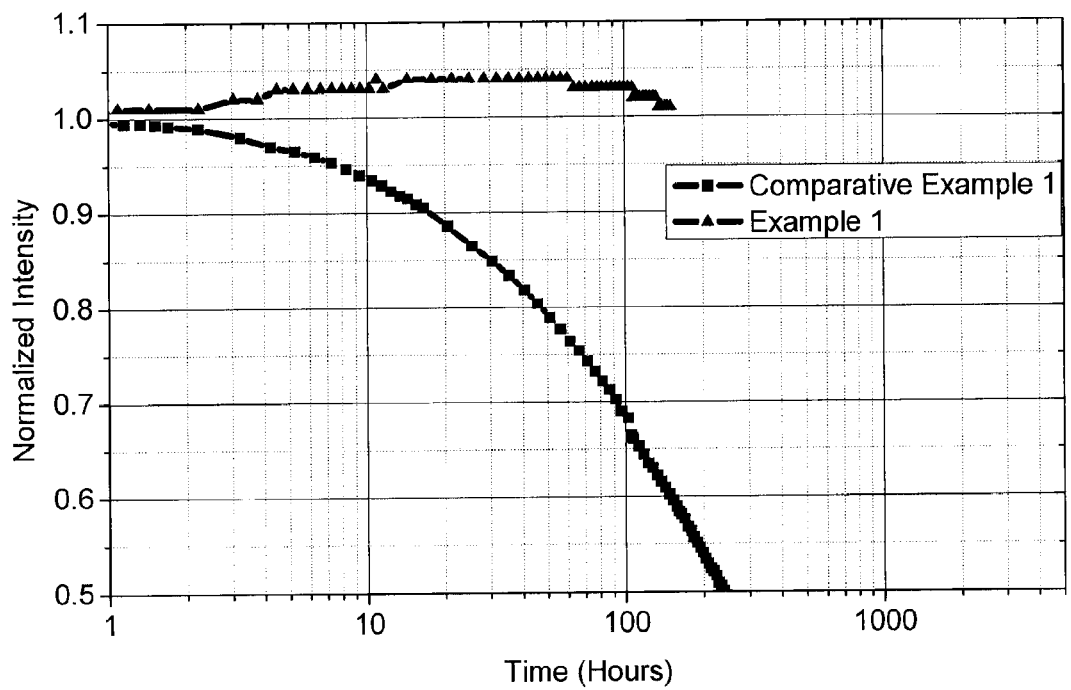
FIG. 7 shows the operating lifetimes of the devices of Example 1 and Comparative Example 1, depicted as a plot of luminous intensity versus time.

Table 1 and FIG. 7 show that using Compound 1 in the hole injection layer instead of PEDOT/PSS results in an unexpectedly dramatic increase in the lifetime of the device, which is far out of proportion to the small reduction in device efficiency and performance as shown in FIGS. 4-6.

Figure 8:
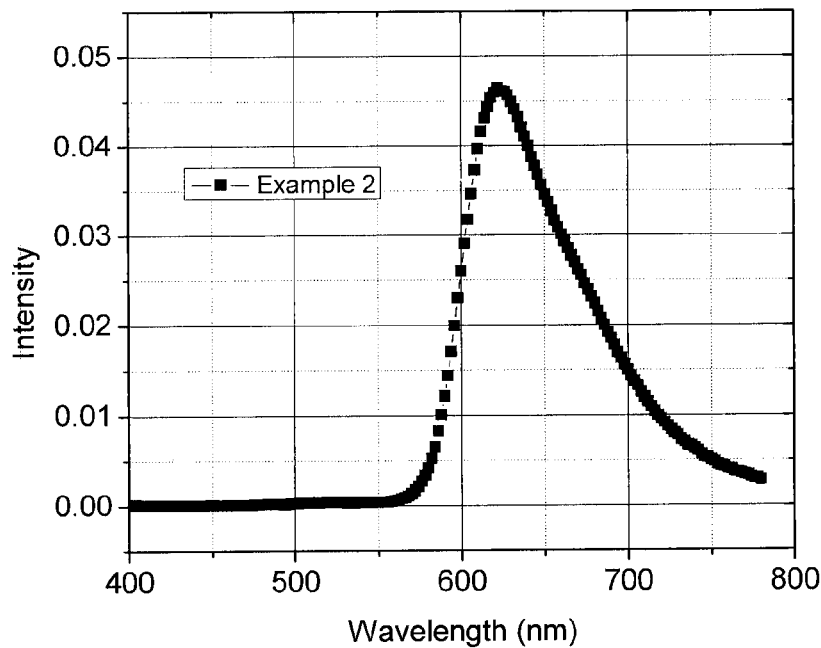
FIG. 8 shows the electroluminescence spectrum produced by the device of Example 2.
Figure 9:
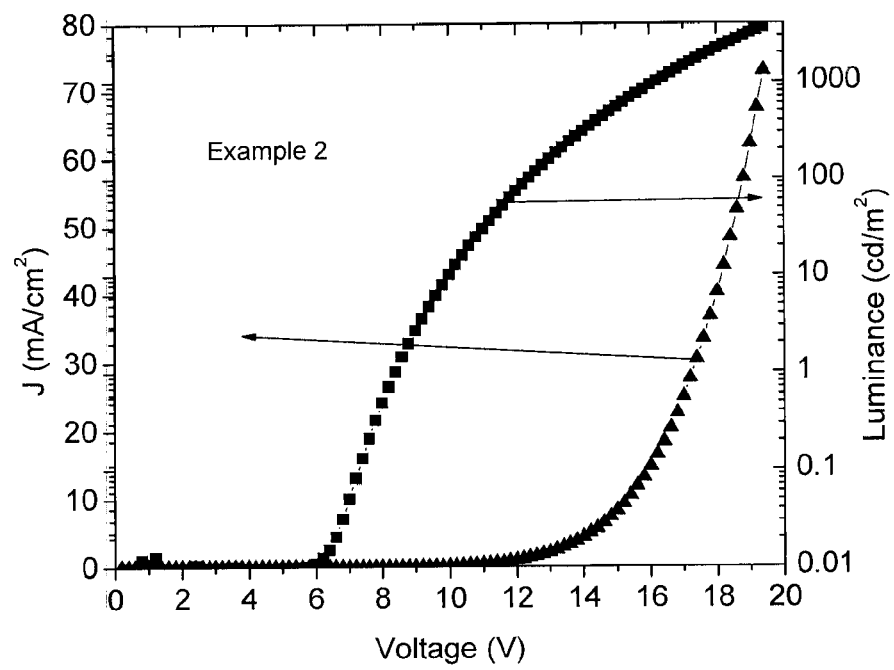
FIG. 9 shows the current-voltage-luminance plots for the device of Example 2.
Figure 10:
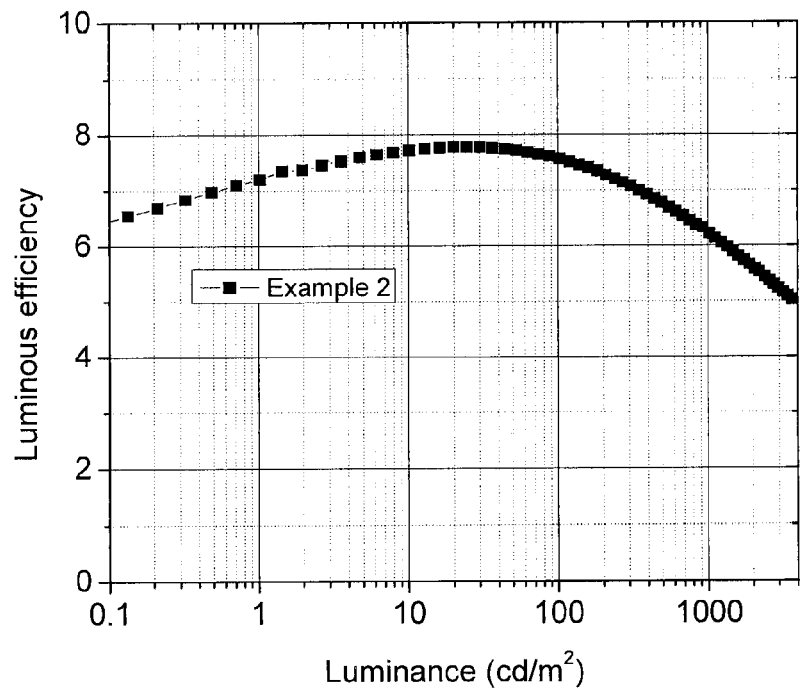
FIG. 10 shows the current efficiency for the device of Example 2, depicted as a plot of luminous efficiency versus luminance.

The device of Example 2 was fabricated in the same manner as Example 1, except that the emissive layer was deposited by spin-coating a solution of 0.75 wt % Host-1 and dopants Green-1 and Red-1 (ratio of 70:20:10). Under DC current, the device of Example 2 produced the emission spectrum shown in FIG. 8, which has a peak at around 622 nm from the red dopant in the emissive layer. Notably absent is any phosphorescence from Compound 1, which would be detected in the green region of the emission spectrum. This data indicates that all the detectable emission is from the emissive layer and none is from Compound 1 in the hole injection layer. Other device performance data are shown in FIGS. 9 and 10.

The device of Example 3 was fabricated in a manner similar to the device of Comparative Example 1. The hole injection layer was spin-coated from a 0.5 wt % solution of Compound 2 in anisole at 4000 rpm for 30 seconds. The film was baked at 250° C. for 30 min. For the hole transport layer, a 1.0 wt % solution of N$^4$,N$^{4'}$-di(naphthalen-1-yl)-N$^4$,N$^{4'}$-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % Host-1 and Green-2 (host to dopant ratio of 88:12) onto the hole transport layer at 1000 rpm for 30 seconds. The emissive layer was then baked at 100° C. for one hour. ETL 1 is 5 nm of 2,3,6,7,10,11-hexaphenyltriphenylene (HPT) and ETL2 is 45 nm of Alq$_3$, both of which were deposited by vacuum thermal evaporation. The device of Example 4 was fabricated in the same manner as Example 3 except that the hole injection material was Compound 1.

Figure 11:
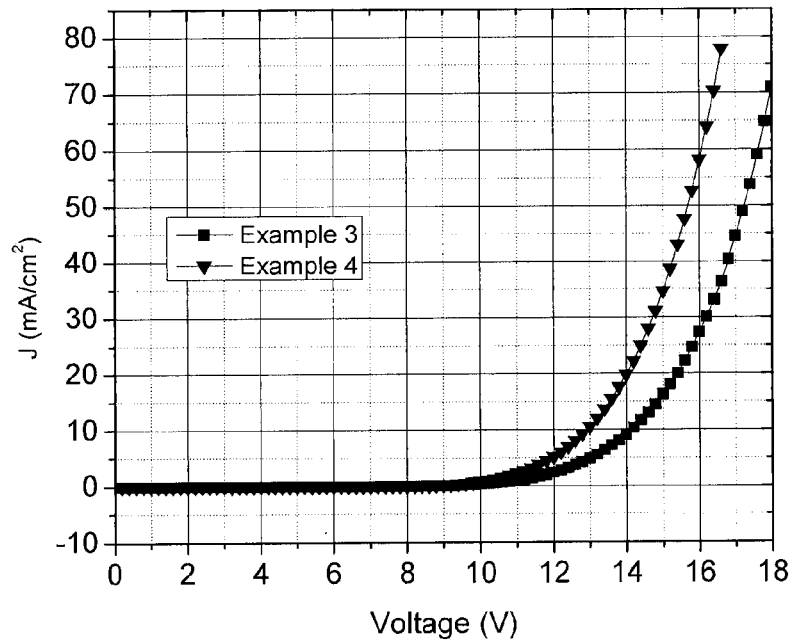
FIG. 11 shows a plot of current density as a function of voltage for the devices of Examples 3 and 4.
Figure 12:
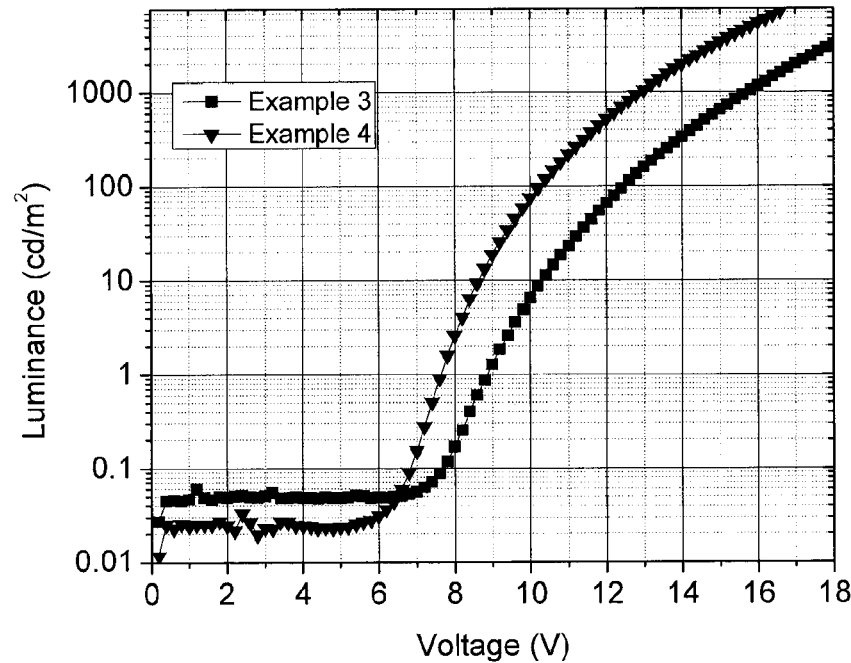
FIG. 12 shows a plot of luminance as a function of voltage for the devices of Examples 3 and 4.
Figure 13:
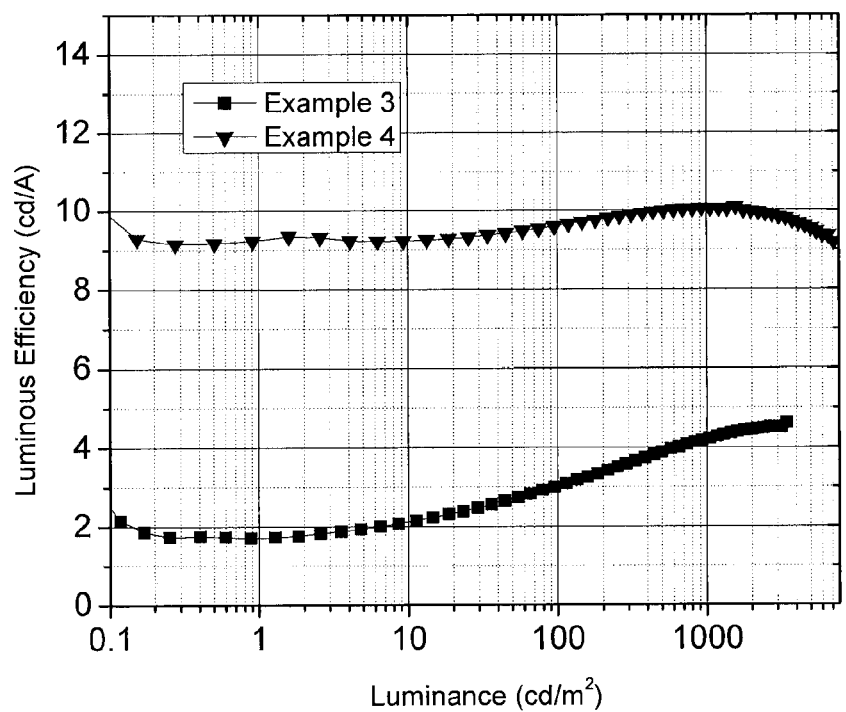
FIG. 13 shows a plot of current efficiency for the devices of Examples 3 and 4, depicted as a plot of luminous efficiency versus luminance.

Device Examples 3 and 4 were operated under DC current and performance data was obtained, as shown in FIGS. 11-13. Table 2 below summarizes the composition and the performance characteristics of device Examples 3 and 4.

TABLE 2

|  | Example 3 | Example 4 |
| --- | --- | --- |
| Hole injection layer | Compound 2 | Compound 1 |
| Hole transporting layer | HTL-1 | HTL-1 |
| Emissive layer | Host-1:Green-2 (88:12) | Host-1:Green-2 (88:12) |
| ETL1 | HPT | HPT |
| Voltage (V) at 1000 cd/m$^2$ | 15.6 | 12.9 |
| Luminous efficiency (cd/A) at 1000 cd/m$^2$ | 4.3 | 10.1 |

This data demonstrates that the device of Example 4, which uses Compound 1 in the hole injection layer, has better performance characteristics than the device of Example 3, which uses Compound 2 in the hole injection layer. This comparison demonstrates that different spacer groups on the cross-linkable iridium complex can influence the device performance. This effect may be due to different spacer groups having different flexibilities, geometries, electrochemistries, or their effect on the ITO anode (e.g., inducing a surface dipole on the ITO anode).

The following examples demonstrate that device performance can be further enhanced by including a dopant in the hole-injection layer. The device of Example 5 was fabricated in a manner similar to the device of Comparative Example 1. The hole injection layer was spin-coated from a 0.25 wt % solution of 95% Compound 1 and 5% of the dopant trityltetrakis(pentafluorophenyl)borate (CD1) in cyclohexanone at 4000 rpm for 30 seconds. The film was baked at 250° C. for 30 min. For the hole transport layer, a 1.0 wt % solution of N4,N4'-di(naphthalen-1-yl)-N4,N4'-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % Host-1 and Green-2 (host to dopant ratio: 88:12) onto the hole transport layer at 1000 rpm for 30 seconds. The emissive layer was then baked at 100° C. for one hour. ETL1 is 5 nm of 2,3,6,7,10,11-hexaphenyltriphenylene (HPT) and ETL2 is 50 nm of Alq$_3$, both of which were deposited by vacuum thermal evaporation. The devices of Examples 6 and 7 were fabricated in the same manner as that of Example 5, except that the dopant used in the hole injection layer was 4-isopropyl-4'-methyl-diphenyliodonium (pentafluorophenyl)borate (CD2) and N,N-dimethylanilinium tetrakis(pentafluorophenyl)borate (CD3), respectively.

Figure 14:
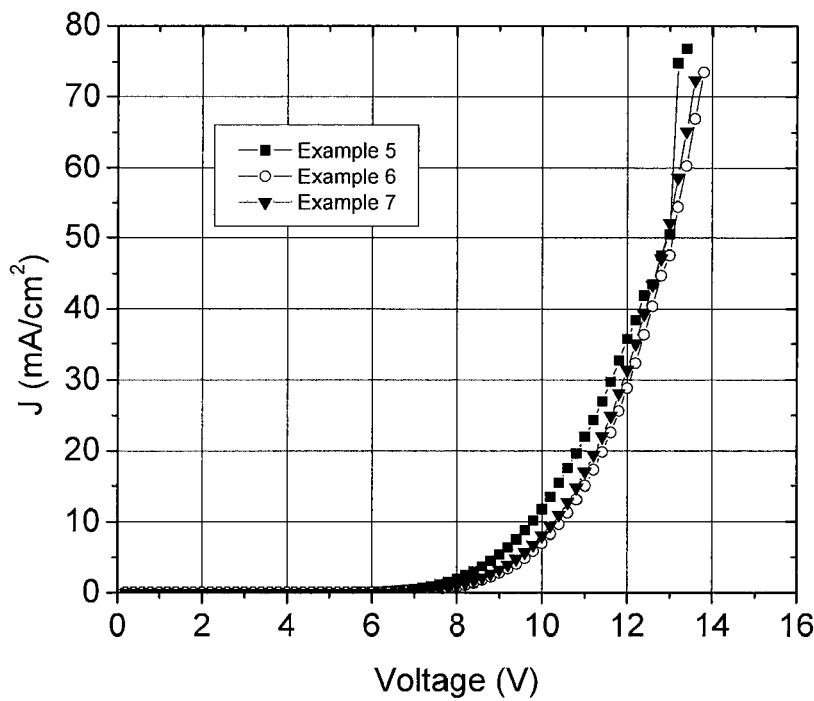
FIG. 14 shows a plot of current density as a function of voltage for the devices of Examples 5, 6, and 7.
Figure 15:
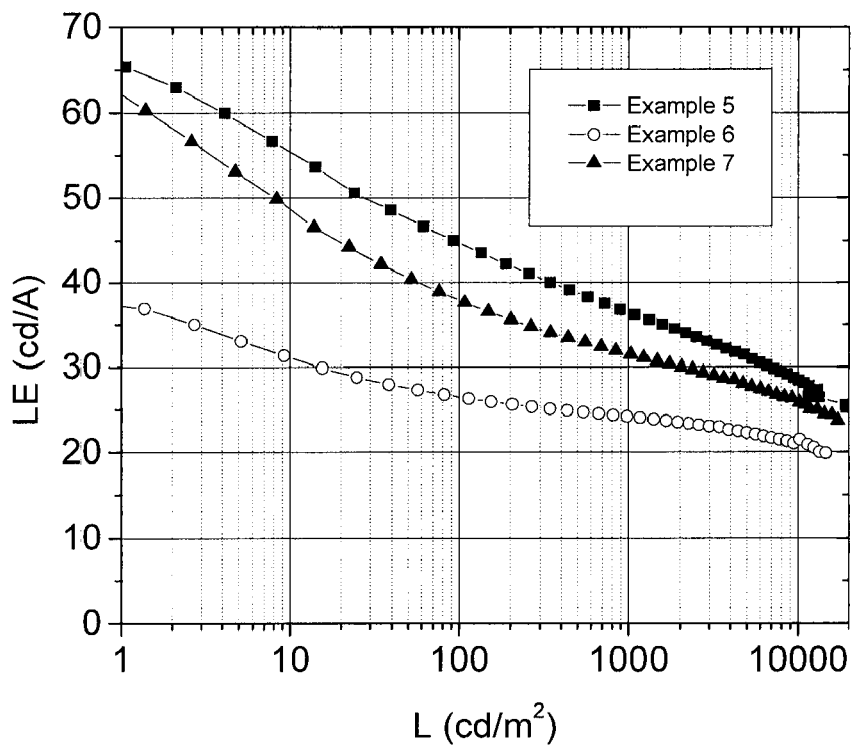
FIG. 15 shows a plot of current efficiency for the devices of Examples 5, 6, and 7 depicted as a plot of luminous efficiency versus luminance.
Figure 16:
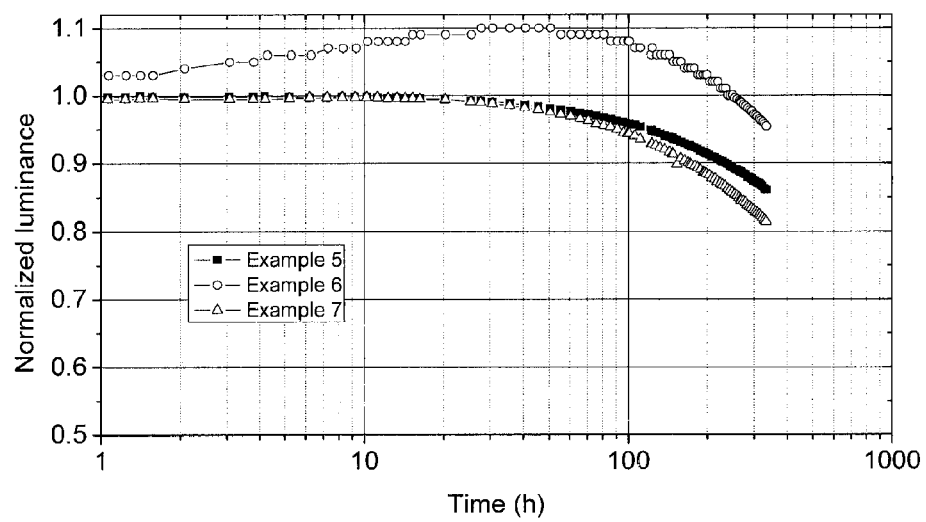
FIG. 16 shows the operating lifetimes of the devices of Examples 5, 6, and 7, depicted as a plot of luminous intensity versus time.

Device Examples 5-7 were operated under DC current and performance data was obtained, as shown in FIGS. 14-16. Table 3 below summarizes the composition and the performance characteristics of device Examples 5-7. This data demonstrates that doping the HIL with a conductivity dopant can serve to improve the performance of the devices. For example, the data shows that the operating voltage of the OLED devices are significantly reduced and the luminous efficiency is increased in comparison to the devices of Examples 3 and 4, which do not have dopants in the HIL. This effect may be due to the ability of the conductivity dopants to enhance hole mobility in the HIL, improve the ITO/HIL interface, improve charge injection, and/or promote polymerization of the cross-linkable iridium complex.

TABLE 3

|  | Example 5 | Example 6 | Example 7 |
| --- | --- | --- | --- |
| Hole injection layer | Compound 1 (95%):CD1 (5%) | Compound 1 (95%):CD2 (5%) | Compound 1 (95%):CD3 (5%) |
| Hole transporting layer | HTL-1 | HTL-1 | HTL-1 |
| Emissive layer | Host-1:Green-2 (88:12) | Host-1:Green-2 (88:12) | Host-1:Green-2 (88:12) |
| ETL1 | HPT | HPT | HPT |
| Voltage (V) at 1000 cd/m$^2$ | 8.3 | 9.4 | 9.0 |
| Luminous efficiency (cd/A) at 1000 cd/m$^2$ | 36.5 | 24.2 | 31.2 |

TABLE 3-continued

| | Example 5 | Example 6 | Example 7 |
|---|---|---|---|
| L 80% (hrs) at $L_0 = 2000$ cd/m² | 450 | 450 | 350 |

The device of Example 8 was fabricated in a manner similar to the device of Comparative Example 1. The hole injection layer was spin-coated from a 0.25 wt % solution of 97% Compound 2 and 3% of the dopant trityl-tetrakis(pentafluorophenyl)borate (CD1) in cyclohexanone at 4000 rpm for 30 seconds. The film was baked at 200° C. for 30 min. For the hole transport layer, a 1.0 wt % solution of N4,N4'-di(naphthalen-1-yl)-N4,N4'-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % Host-2 and Green-2 (host to dopant ratio: 88:12) onto the hole transport layer at 1000 rpm for 30 seconds. The emissive layer was then baked at 100° C. for one hour. ETL1 is 5 nm of 2,3,6,7,10,11-hexaphenyltriphenylene (HPT) and ETL2 is 50 nm of Alq$_3$, both of which were deposited by vacuum thermal evaporation. Device Example 8 was operated under DC current and performance data was obtained. The composition and the performance characteristics of the device are summarized in Table 4.

The device of Example 9 was fabricated in a manner similar to the device of Example 8 except that 7% of CD1 was used as the conductivity dopant. The efficiency of the device was higher than that of device Example 8. Device Example 9 was operated under DC current and performance data was obtained. The composition and the performance characteristics of the device are summarized in Table 4.

The device of Example 10 was fabricated in a manner similar to the device of Example 8. The hole injection layer was spin-coated from a 0.25 wt % solution of 90% Compound 6 and 10% of the dopant trityl-tetrakis(pentafluorophenyl)borate (CD1) in cyclohexanone at 4000 rpm for 30 seconds. The film was baked at 200° C. for 30 min. For the hole transport layer, a 1.0 wt % solution of N4,N4'-di(naphthalen-1-yl)-N4,N4'-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % Host-1 and Green-2 (host to dopant ratio: 88:12) onto the hole transport layer at 1000 rpm for 30 seconds. The emissive layer was then baked at 100° C. for one hour. ETL1 is 5 nm of 2,3,6,7,10,11-hexaphenyltriphenylene (HPT) and ETL2 is 50 nm of Alq$_3$, both of which were deposited by vacuum thermal evaporation. Device Example 10 was operated under DC current and performance data was obtained. The composition and the performance characteristics of the device are summarized in Table 4.

The device of Example 11 was fabricated in a manner similar to the device of Example 10 except that the hole injection layer was spin-coated from a 0.25 wt % solution of 95% Compound 10 and 5% of the dopant trityl-tetrakis(pentafluorophenyl)borate (CD1) in cyclohexanone at 4000 rpm for 30 seconds. Device Example 11 was operated under DC current and performance data was obtained. The composition and the performance characteristics of the device are summarized in Table 4.

The device of Example 12 was fabricated in a manner similar to the device of Example 10 except that the hole injection layer was spin-coated from a 0.25 wt % solution of 95% Compound 11 and 5% of the dopant trityl-tetrakis(pentafluorophenyl)borate (CD1) in cyclohexanone at 4000 rpm for 30 seconds. Device Example 12 was operated under DC current and performance data was obtained. The composition and the performance characteristics of the device are summarized in Table 4.

The device of Example 13 was fabricated in a manner similar to the device of Example 10 except that the hole injection layer was spin-coated from a 0.25 wt % solution of 95% Compound 12 and 5% of the dopant trityl-tetrakis(pentafluorophenyl)borate (CD1) in cyclohexanone at 4000 rpm for 30 seconds. Device Example 13 was operated under DC current and performance data was obtained. The composition and the performance characteristics of the device are summarized in Table 4.

The device of Example 14 was fabricated in a manner similar to the device of Example 8. The hole injection layer was spin-coated from a 0.25 wt % solution of 95% Compound 13 and 5% of the dopant trityl-tetrakis(pentafluorophenyl)borate (CD1) in cyclohexanone at 4000 rpm for 30 seconds. The film was baked at 225° C. for 30 min. For the hole transport layer, a 1.0 wt % solution of N4,N4'-di(naphthalen-1-yl)-N4,N4'-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % Host-3 and Green-2 (host to dopant ratio: 88:12) onto the hole transport layer at 1000 rpm for 30 seconds. The emissive layer was then baked at 100° C. for one hour. ETL1 is 5 nm of 2,3,6,7,10,11-hexaphenyltriphenylene (HPT) and ETL2 is 50 nm of Alq$_3$, both of which were deposited by vacuum thermal evaporation. Device Example 14 was operated under DC current and performance data was obtained. The composition and the performance characteristics of the device are summarized in Table 4.

The device of Example 15 was fabricated in a manner similar to the device of Example 14 except that the hole injection layer was spin-coated from a 0.25 wt % solution of 95% Compound 14 and 5% of the dopant trityl-tetrakis(pentafluorophenyl)borate (CD1) in cyclohexanone at 4000 rpm for 30 seconds. The HIL film was baked at 200° C. for 30 min. Device Example 15 was operated under DC current and performance data was obtained. The composition and the performance characteristics of the device are summarized in Table 4.

The device of Example 16 was fabricated in a manner similar to the device of Example 14 except that the hole injection layer was spin-coated from a 0.25 wt % solution of 95% Compound 15 and 5% of the dopant trityl-tetrakis(pentafluorophenyl)borate (CD1) in cyclohexanone at 4000 rpm for 30 seconds. Device Example 16 was operated under DC current and performance data was obtained. The composition and the performance characteristics of the device are summarized in Table 4.

The device of Example 17 was fabricated in a manner similar to the device of Example 8. The hole injection layer was spin-coated from a 0.25 wt % solution of 95% Compound 16 and 5% of the dopant trityl-tetrakis (pentafluorophenyl) borate (CD1) in cyclohexanone at 4000 rpm for 30 seconds. The film was baked at 200° C. for 30 min. For the hole transport layer, a 1.0 wt % solution of N4,N4'-di(naphthalen-1-yl)-N4,N4'-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % Host-4 and Green-2 (host to dopant ratio: 88:12) onto the hole transport layer at 1000 rpm for 30 seconds. The emissive layer was then baked at 100° C. for one hour. ETL1 is 5 nm of 2,3,6,7,10,11-hexaphenyltriphenylene (HPT) and ETL2 is 50 nm of $Alq_3$, both of which were deposited by vacuum thermal evaporation. Device Example 17 was operated under DC current and performance data was obtained. The composition and the performance characteristics of the device are summarized in Table 4.

devices emit similar colors. But if $L_1$ has a higher molecular weight than $L_2$, then $Ir(L_1)_3$ would require a higher vacuum evaporation temperature than $Ir(L_2)_3$, thus reducing the attractiveness of using $Ir(L_1)_3$. In this case, a heteroleptic $Ir(L_1)(L_2)_2$ or $Ir(L_1)_2(L_2)$ complex may possess desirable features that are imparted by each ligand (i.e., $L_1$ imparts good stability, while $L_2$ imparts reduced molecular weight and lower evaporation temperature).

Also, in another situation, if $Ir(L_1)_3$ is insoluble whereas $Ir(L_2)_3$ is soluble in most organic solvents, $Ir(L_1)_3$ could not be used in solution-based device fabrication methods such as inkjet printing. In this case, a heteroleptic $Ir(L_1)(L_2)_2$ or $Ir(L_1)_2(L_2)$ complex may possess both good stability (as imparted by $L_1$) and good solubility (as imparted by $L_2$).

Although heteroleptic metal complexes can have these advantages, making such heteroleptic complexes can be a challenge. One problem is scrambling of the ligands during the synthesis process, which results in a mixture of $Ir(L_1)(L_2)_2$ and $Ir(L_1)_2(L_2)$, and even $Ir(L_1)_3$ and $Ir(L_2)_3$. Separating the components of this mixture can be difficult using conventional separation techniques, such as column chromatography, sublimation, or recrystallization. Therefore, there is a need for an improved method of making heteroleptic metal complexes.

TABLE 4

| Example | HIL | HTL | EML | ETL1 | Voltage (@ 1000 nits) | Luminous efficiency (@ 1000 nits) | Lifetime (hr) (80% drop from 4000 nits) |
|---|---|---|---|---|---|---|---|
| 8 | Cmpd 2: CD1 (3%) | HTL-1 | Host-2:Green-2 (88:12) | HPT | 8.0 | 46 | 180 |
| 9 | Cmpd 2: CD1 (7%) | HTL-1 | Host-2:Green-2 (88:12) | HPT | 7.4 | 50 | 120 |
| 10 | Cmpd 6: CD1 (10%) | HTL-1 | Host-1:Green-2 (88:12) | HPT | 10.9 | 22 | 215 |
| 11 | Cmpd 10: CD1 (5%) | HTL-1 | Host-1:Green-2 (88:12) | HPT | 8.5 | 40 | 92 |
| 12 | Cmpd 11: CD1 (5%) | HTL-1 | Host-1:Green-2 (88:12) | HPT | 8 | 40 | 76 |
| 13 | Cmpd 12: CD1 (5%) | HTL-1 | Host-1:Green-2 (88:12) | HPT | 8.8 | 41 | 140 |
| 14 | Cmpd 13: CD1 (5%) | HTL-1 | Host-3:Green-2 (88:12) | HPT | 7.8 | 46 | 87 |
| 15 | Cmpd 14: CD1 (5%) | HTL-1 | Host-3:Green-2 (88:12) | HPT | 10.2 | 25 | 700 |
| 16 | Cmpd 15: CD1 (5%) | HTL-1 | Host-3:Green-2 (88:12) | HPT | 8 | 44 | 130 |
| 17 | Cmpd 16: CD1 (10%) | HTL-1 | Host-4:Green-2 (88:12) | HPT | 7.9 | 50 | 208 |

Some of the cross-linkable iridium complexes of the present invention are heteroleptic iridium complexes, represented as $Ir(L_1)_x(L_2)_y$, where $L_1$ and $L_2$ are different C—Ir—N cyclometallating organic ligands. Such heteroleptic metal complexes may take advantage of the desirable properties imparted by the different ligands.

For example, consider where an electrophosphorescent device containing $Ir(L_1)_3$ as the emitter is more stable than a device containing $Ir(L_2)_3$ as the emitter, although both As such, in another aspect, the present invention provides heteroleptic metal complexes which have a separation enhancing functional group that differentiates the heteroleptic metal complexes in the mixture in such a manner that the different metal complexes can be separated by conventional separation techniques, such as column chromatography. The separation enhancing functional groups are used to create metal complexes having the formula: $M(L_1)(L_B)_2$ or $M(L_1)_2(L_B)$, wherein M is a metal atom, wherein $L_1$ and $L_B$ are different ligands that are coordinated to metal M, and wherein $L_B$ includes a separation enhancing functional group.

These metal complexes, having the formula $M(L_1)(L_B)_2$ or $M(L_1)_2(L_B)$, can be made from a mixture containing a metal complex having the formula $M(L_1)(L_A)_2$ and a metal complex having the formula $M(L_1)_2(L_A)$, wherein $L_1$ and $L_A$ are different ligands that are coordinated to the metal atom M. Ligand $L_A$ includes at least one halogen-containing group. As used herein, "halogen-containing group" refers to F, Cl, Br, or I, or a functional group containing at least one of F, Cl, Br, or I. By substituting the halogen-containing groups on the $L_A$ ligands with a separation enhancing functional group, a second mixture is formed containing metal complexes $M(L_1)(L_B)_2$ or $M(L_1)_2(L_B)$. After separation and isolation, metal complexes $M(L_1)(L_B)_2$ or $M(L_1)_2(L_B)$ can be subjected to further reactions (e.g., cross-coupling, deprotection, condensation, cleavage, or acylation) to make other heteroleptic metal complexes, such as those that are phosphorescent emitters or hole transporting materials.

For example, when 2-(biphenyl-3-yl)pyridine and 2-phenylpyridine are reacted with Ir(acac)$_3$, a mixture of I-A, I-B, I-C, and I-D are formed with the ratio depending upon the feed ratio of the two ligands. These four components are not easily separated by column chromatography because their ligands have similar polarity.

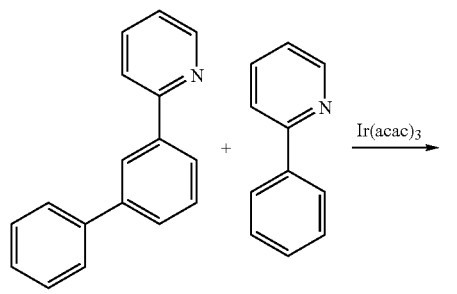

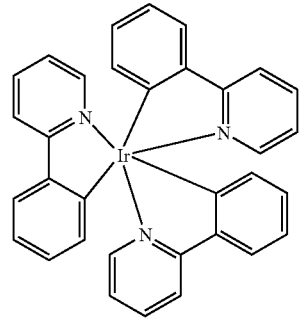

I-A

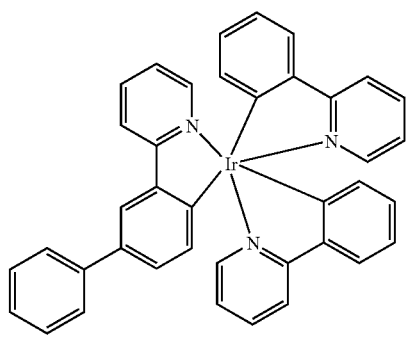

I-B

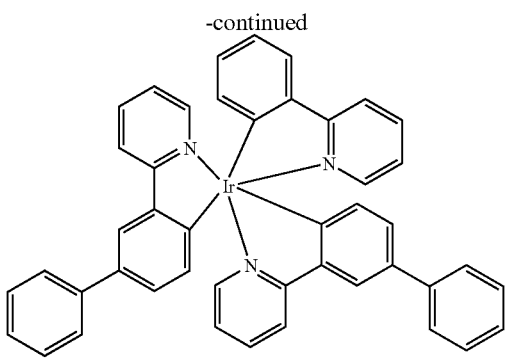

I-C

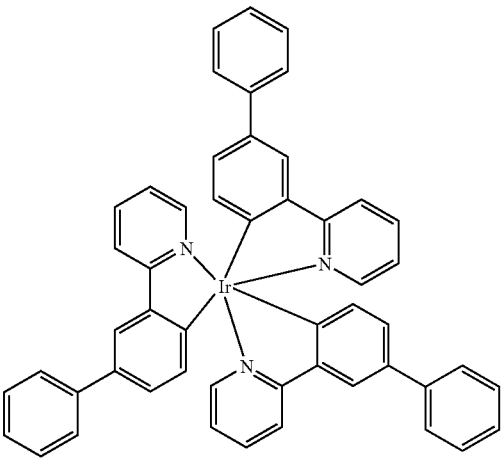

I-D

In order to make pure compound I-B, a mixture of brominated Ir(PPy)$_3$ was first made by reacting of Ir(PPy)$_3$ with one equivalent of N-bromosuccimide (NBS). A mixture of unreacted Ir(PPy)$_3$, monobromo Ir(PPy)$_3$ (II-A), and dibromo Ir(PPy)$_3$ (II-B) was obtained. To increase the polarity difference among the different metal complexes, pinacolborate groups (serving as the separation enhancing functional group) were introduced into the metal complex. By this reaction, the metal complexes were converted to their corresponding boronic esters III-A and III-B, which are more easily separated by column chromatography. Boronic-ester metal complexes III-A and III-B can then be converted to metal complexes I-B and I-C, respectively. The process is shown below.

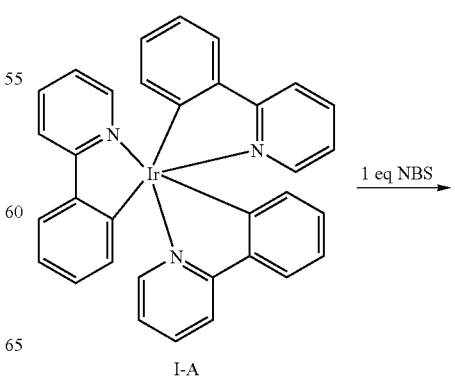

I-A

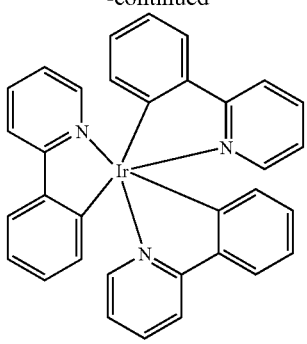
I-A
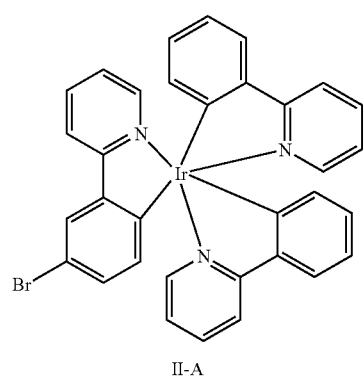
II-A
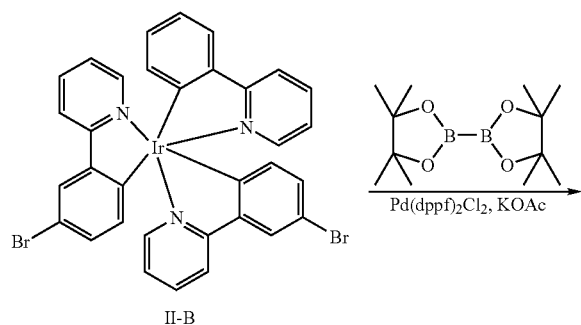
II-B
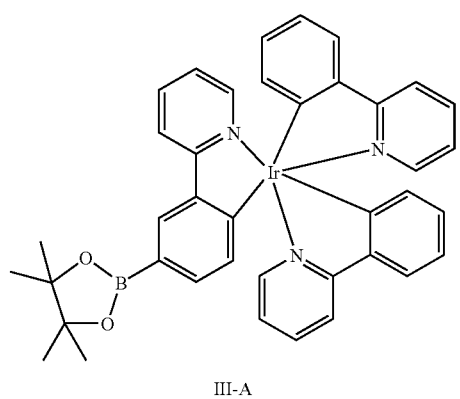
III-A
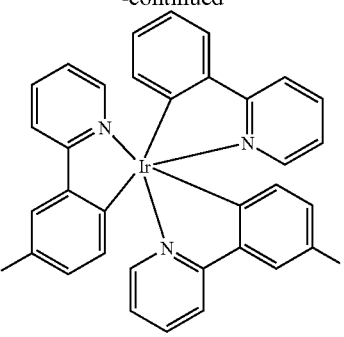
III-B
III-A →(Bromobenzene / Pd catalyst)→
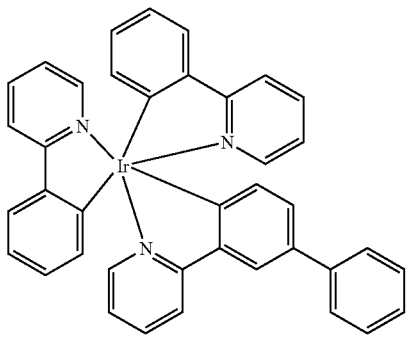
I-B
III-B →(Bromobenzene / Pd catalyst)→
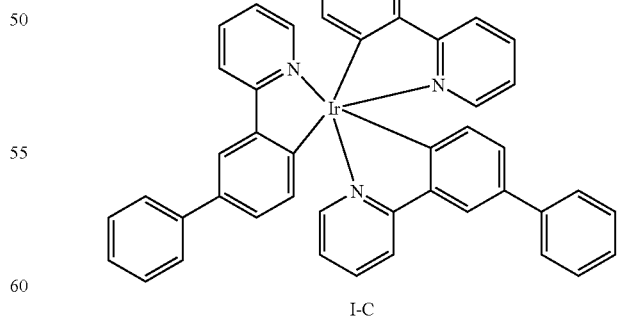
I-C
Other separation enhancing functional groups can be used as well, including those having triflates, trimethysilyl, or amino groups. An example using triflate as a separation enhancing functional group is shown below.

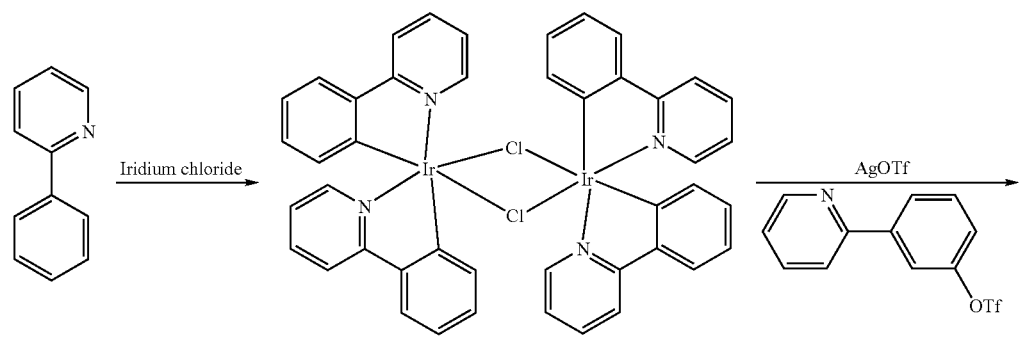
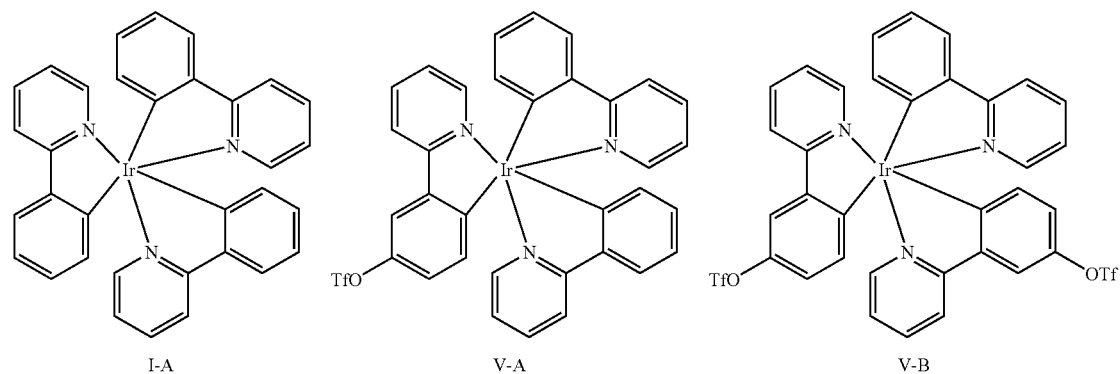
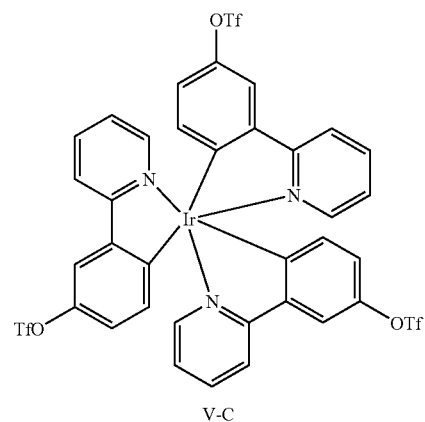
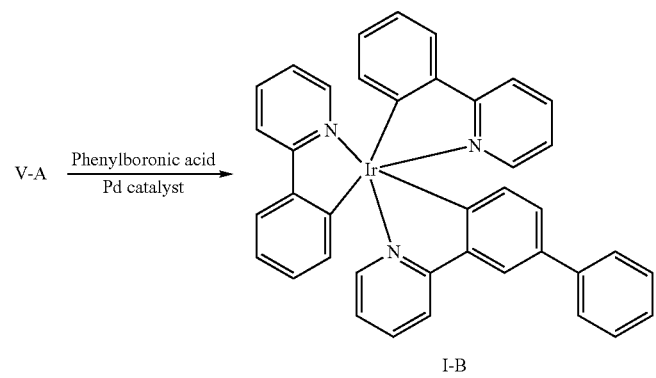

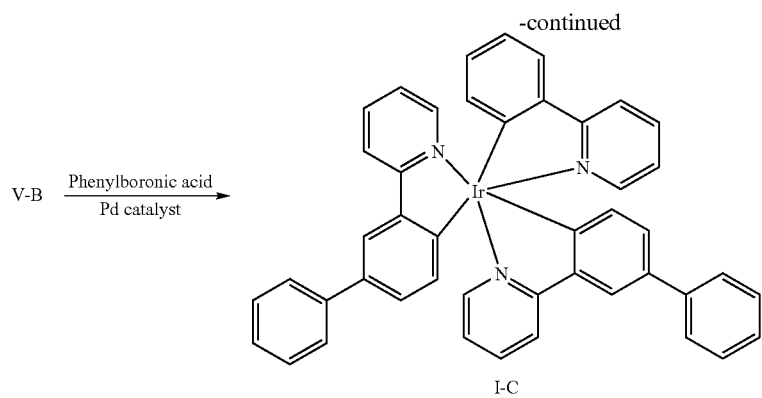
An example using TMS as a separation enhancing functional group is shown below.
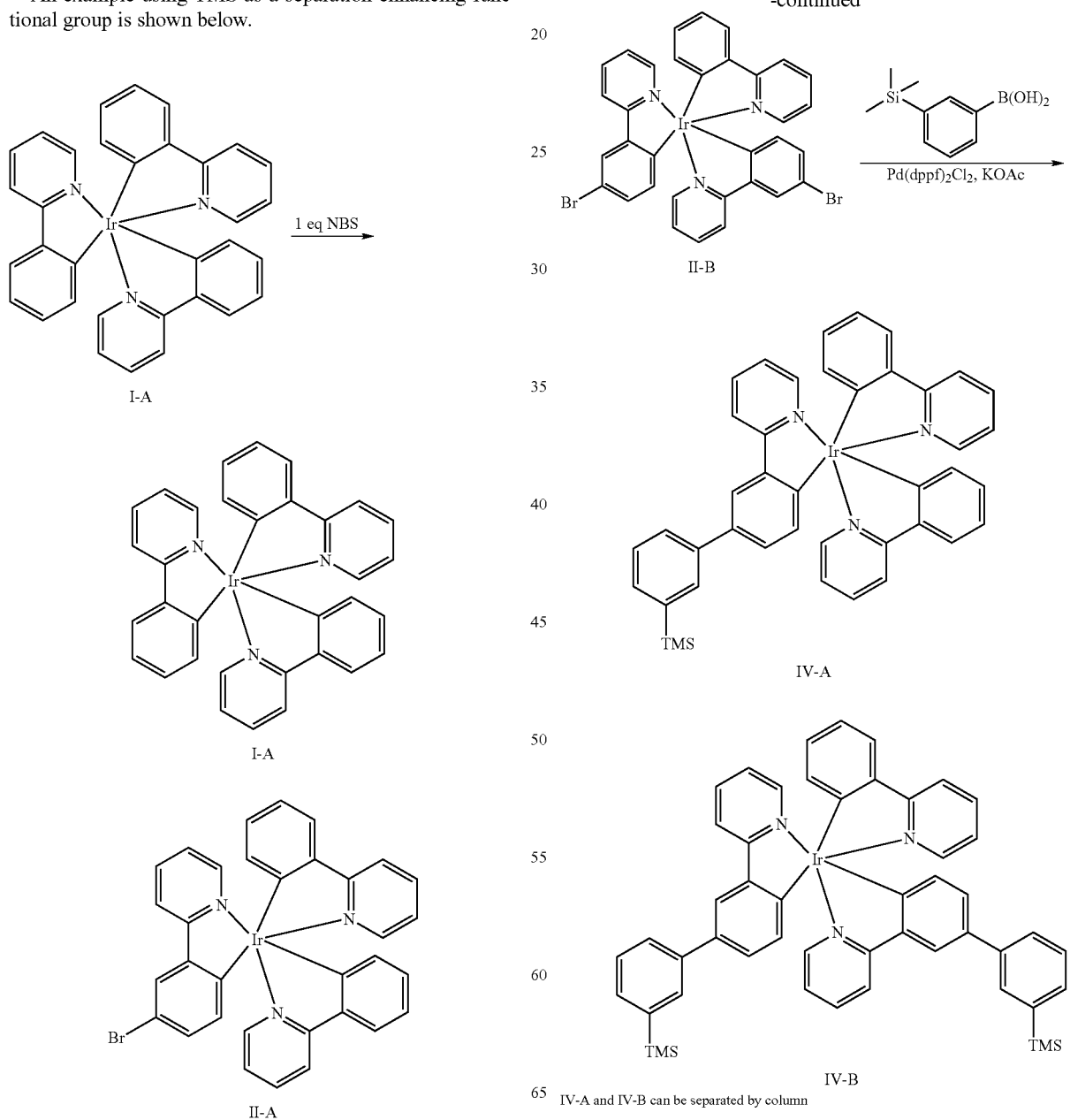
IV-A and IV-B can be separated by column IV-A Cleavage →

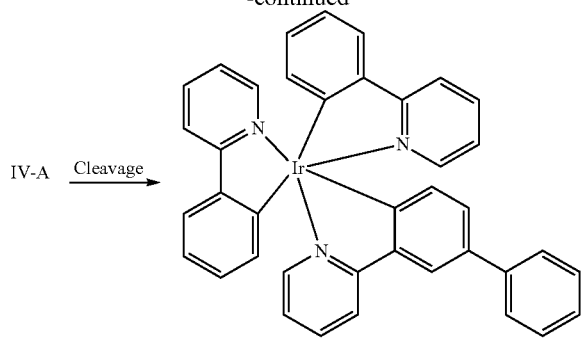

I-B

IV-B Cleavage →

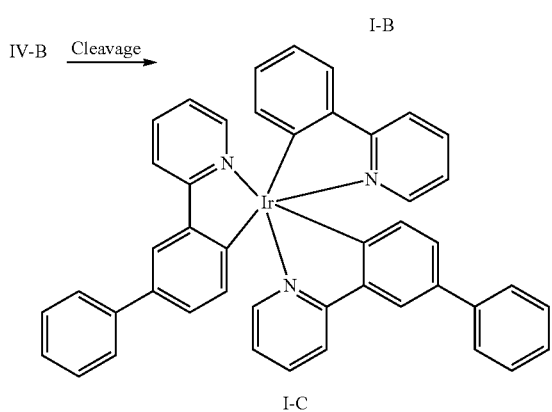

I-C

This method of making heteroleptic metal complexes can be used to make cross-linkable metal complexes of the present invention. The following demonstrates the use of this method for the synthesis of Compound 1, described above.

Synthesis of brominated mixture: With the exclusion of light, a solution of 2.53 g (14.2 mmol) of N-bromosuccimide in 200 ml dichloromethane was added dropwise to an efficiently stirred solution of 9.3 g (14.2 mmol) of fac-tris[2-(2-pyridinyl-κN)pheny-1-κC]iridium(III) in 2300 ml of dichloromethane. The solution was further stirred at room temperature for 15 hours. After concentrating under reduced pressure to a volume of 200 ml, the solution was admixed with 1000 ml of ethanol. Subsequently, the microcrystalline precipitate was filtered off, washed three times with 100 ml of ethanol, and then dried under reduced pressure. 9.3 g of product (brominated mixture) was obtained. The brominated mixture contained about 80% of the monobromo product, 10% of the starting material, and 10% of the dibromo product.

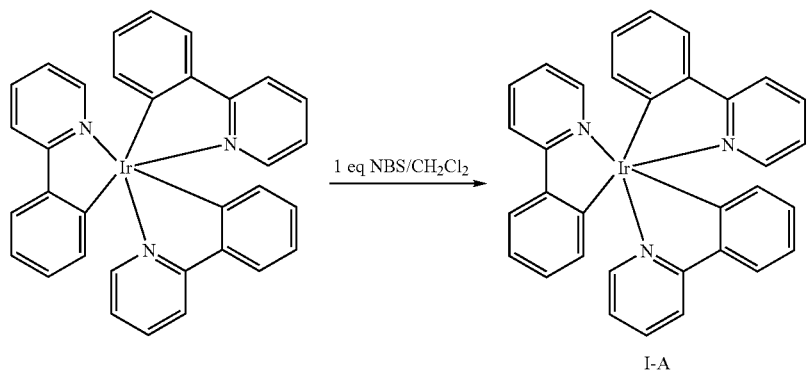

I-A

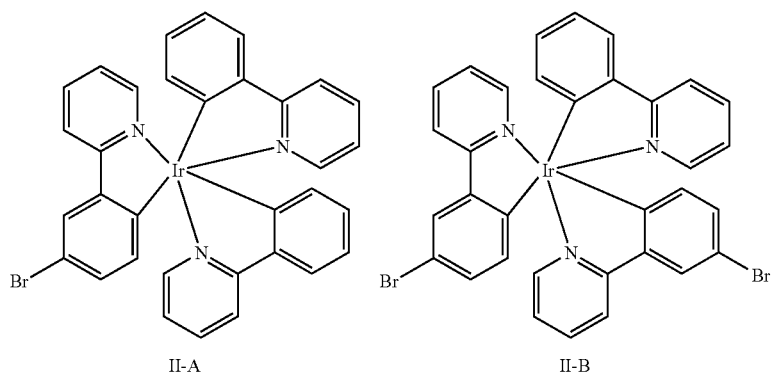

II-A          II-B

Brominated mixture

Synthesis of amino intermediate: fac-bis[2-(2-pyridinyl-κN)phenyl-κC]-[2-(2-pyridinyl-κN)-(5-(4-aminophenyl)phenyl)-κC]iridium(III). 2.0 g of the above brominated mixture, 0.9 g (4.1 mmol) of 4-(4,4,5,5-tetramethyl-1,3,2-dioxaborolan-2-yl)aniline, 1.0 g (7 mmol) of potassium carbonate, 500 mg of toluene, 100 ml of ethanol, and 50 ml of water were mixed and purged with nitrogen for 10 minutes.

To the mixture was then added 0.3 g of Pd(PPh$_3$)$_4$. The mixture was heated to reflux for 30 hours. The mixture was cooled to room temperature and organic layer was separated. The solvent was evaporated under reduced pressure and the residue was purified in a column using dichloromethane as eluent. 1.2 g of mono amino product was obtained.

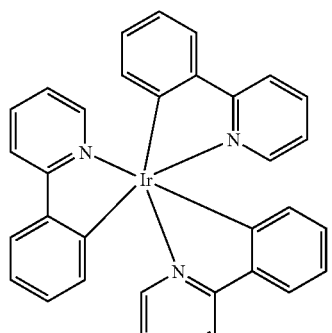

I-A

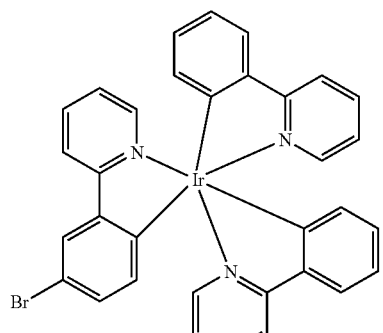

II-A

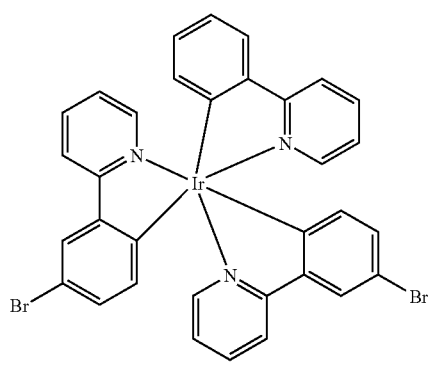

II-B

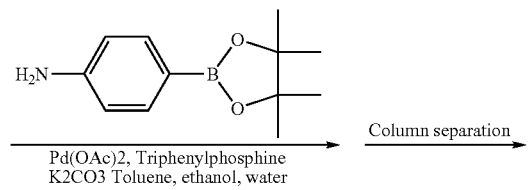

Pd(OAc)2, Triphenylphosphine
K2CO3 Toluene, ethanol, water

Column separation

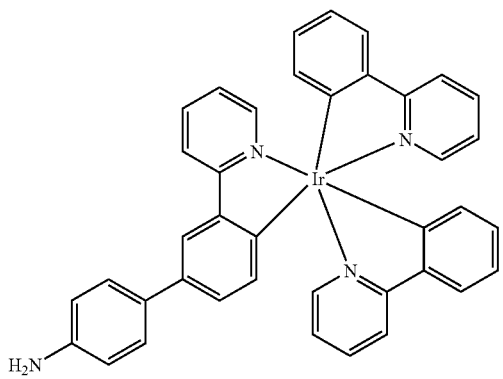

Synthesis of Compound 1: 1.0 g (1.34 mmol) of fac-Bis[2-(2-pyridinyl-κN)phenyl-κC]-[2-(2-pyridinyl-κN)-(5-(4-aminophenyl)phenyl)-κ C]iridium(III) (the above amino intermediate), 0.49 g (2.68 mmol) of 4-bromostyrene, 9 mg of palladium acetate, 0.08 ml of 1M tri-tert-butylphosphine in toluene, 0.39 g (4.0 mmol) of sodium tert-butoxide, and 100 ml of p-xylene was heated to 110° C. for 6 hours under nitrogen. After cooling to room temperature, the reaction mixture was poured into 500 ml of methanol. The precipitate was collected and purified in a column using toluene as eluent. 0.36 g of product (Compound 1) was obtained after purification.

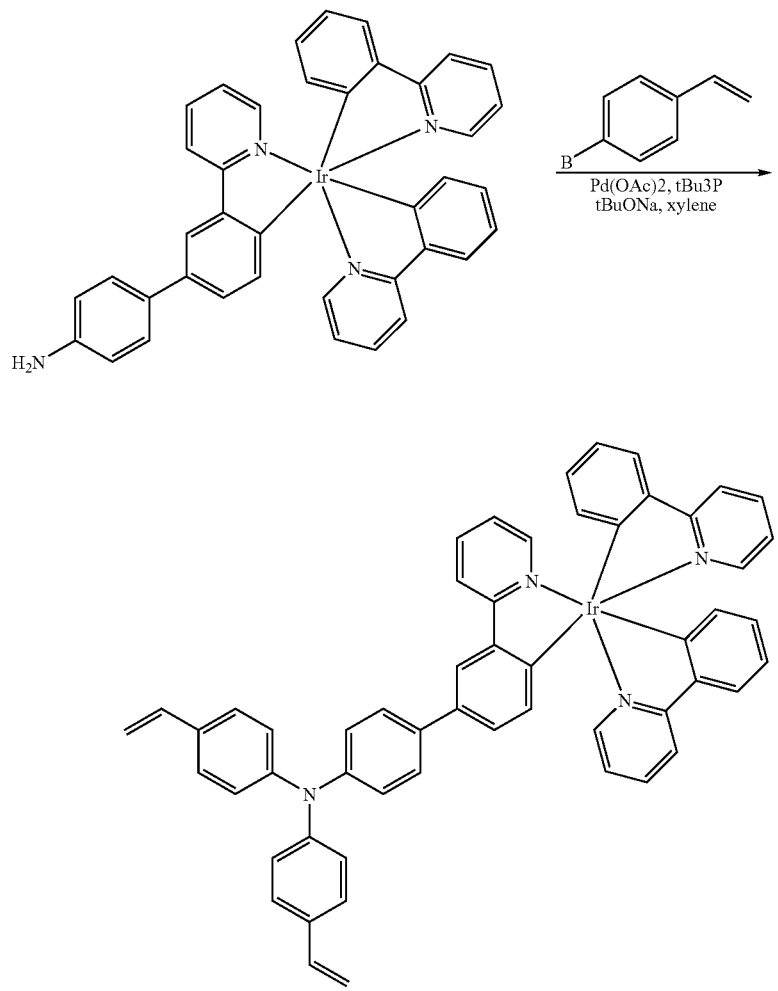

Compound 1

Synthesis of heteroleptic metallic complexes I-B and I-C:

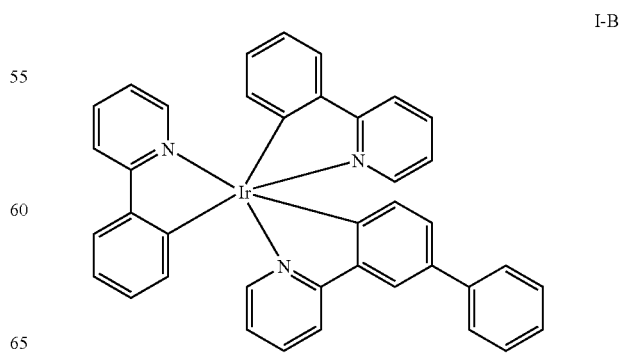

I-B

I-C
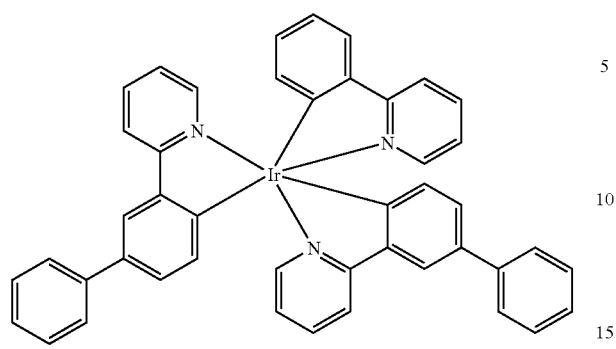
The boronic esters were synthesized as follows:
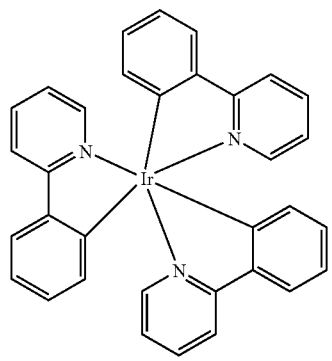
I-A
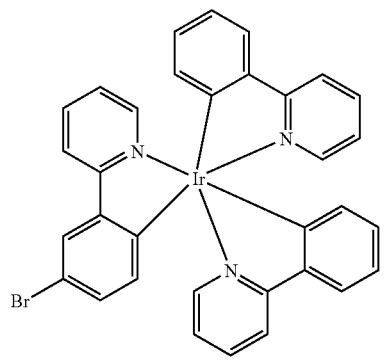
II-A
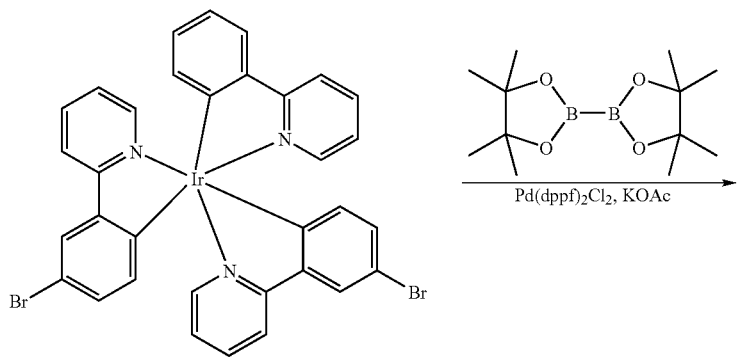
II-B
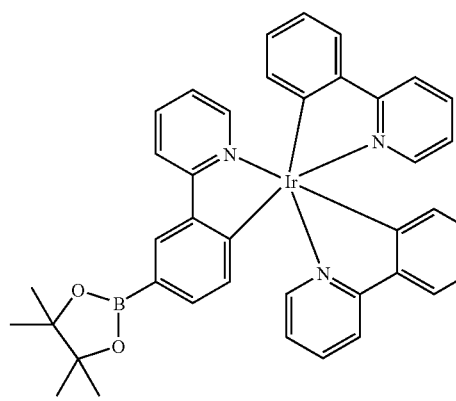
III-A
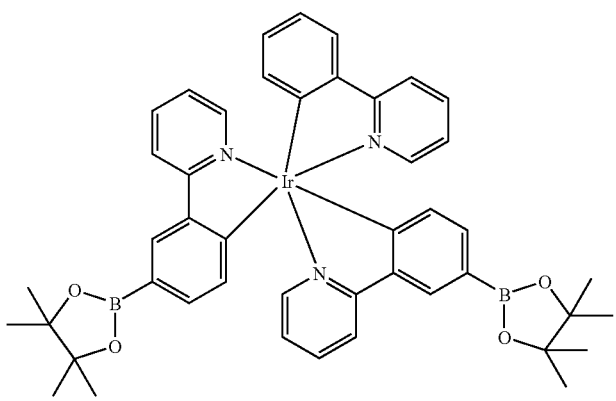
III-B Synthesis of I-B: 1.5 g (1.92 mmol) of the above boronic esters, 0.45 g (2.88 mmol) of bromobenzene, 58 mg (0.12 mmol) of S-phos, 1.2 g (5.7 mmol) of potassium phosphate, 80 ml of toluene, and 8 ml of water were mixed in a three-neck flask. The mixture was bubbled with nitrogen for 20 min. To the degassed mixture was added 0.03 g (0.03 mmol) of Pd$_2$(dba)$_3$. The reaction was refluxed under nitrogen atmosphere for 2 hours. After cooling to room temperature, the reaction mixture was filtered through a celite bed. The yellow precipitate on the celite bed was washed with dichloromethane. The dichloromethane solution was combined with the toluene solution. The solution was dried with magnesium sulfate. After solvent evaporation, the residue was purified by column using 1:1 hexanes and dichloromethane as eluent. 1.2 g pure product (I-B) was obtained. The final product was sublimed under high vacuum at 275° C.

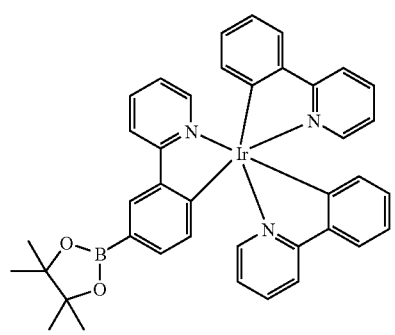

III-A $\xrightarrow{\text{Bromobenzene}}{\text{Pd catalyst}}$

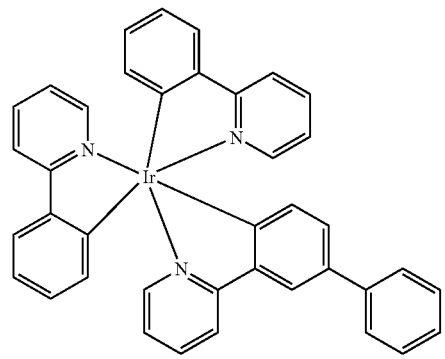

I-B

Synthesis of heteroleptic metal complex I-C (in the same manner as I-B).

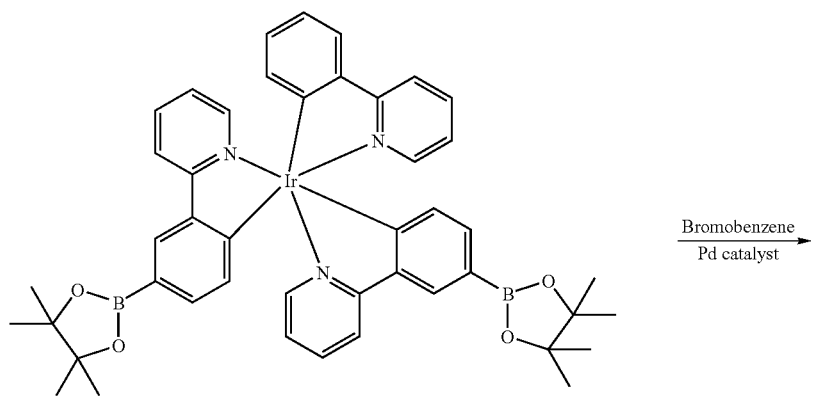

III-B $\xrightarrow{\text{Bromobenzene}}{\text{Pd catalyst}}$

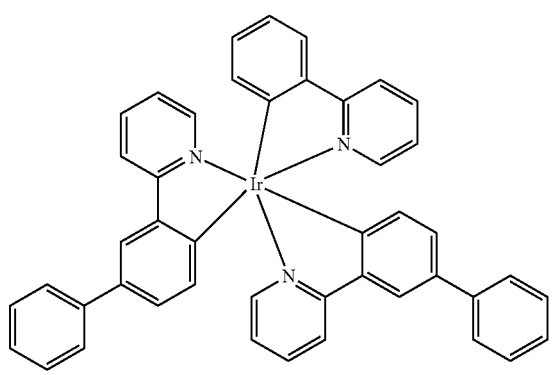

I-C

Synthesis of heteroleptic metal complexes IV-A and IV-B: 6.3 g of brominated Ir(PPy)₃ mixture was put into a three-neck flask. To this flask was then added 2.4 g (12.3 mmol) of 3-trimethylsilylphenyl boronic acid, 0.2 g (0.49 mmol) of S-Phos, 2.8 g (12.3 mmol) of potassium phosphate, 600 ml of toluene, and 60 ml of water. The mixture was degassed for 20 min. 0.11 g (0.12 mmol) of Pd$_2$(dba)$_3$ was added. The mixture was heated up to reflux under nitrogen overnight. The reaction was worked up by separating the organic layer and evaporating solvent. The residue was purified by column chromatography using 1:1 hexanes and dichloromethane as eluent. 1.3 g IV-A and 2 g of IV-B were obtained.

Synthesis of I-B (above): I-B can be synthesized by cleaving the TMS group from IV-A using the method disclosed in Y. Zafrani, E. Gershonov, and I. Columbus, "Efficient and Facile Ar—Si Bond Cleavage by Montmorillonite KSF: Synthetic and Mechanistic Aspects of Solvent-Free Protodesilylation Studied by Solution and Solid-State MAS NMR", *J. Org. Chem.*, vol. 72(18), pp. 7014-7017 (2007).

Synthesis of I-C (above): I-C can be synthesized by cleaving the TMS group from IV-B following the method disclosed in the above-mentioned reference.

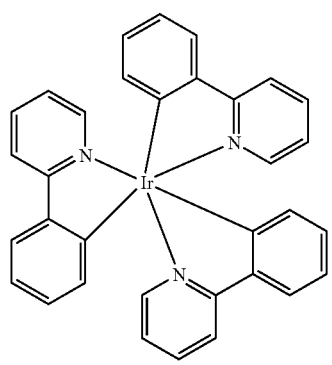

I-A

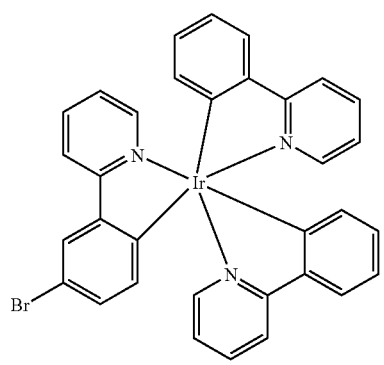

II-A

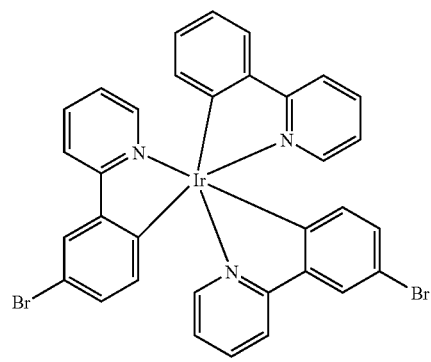

II-B

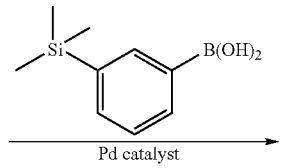

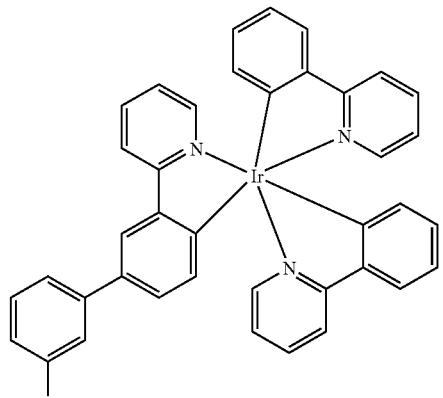

IV-A

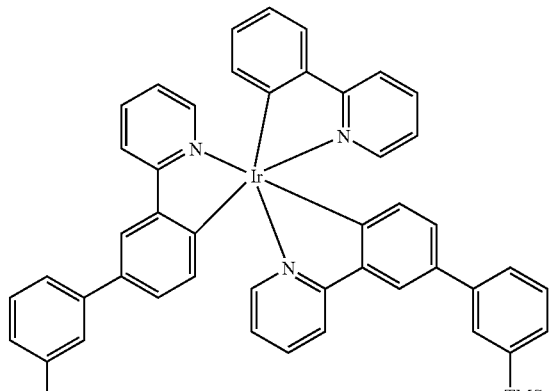

IV-B

Synthesis of Compound V:

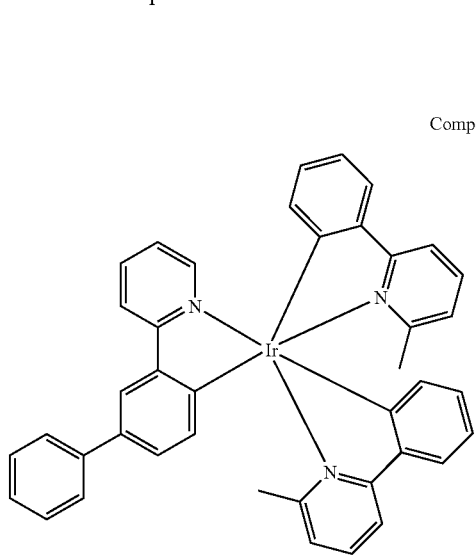

Compound V

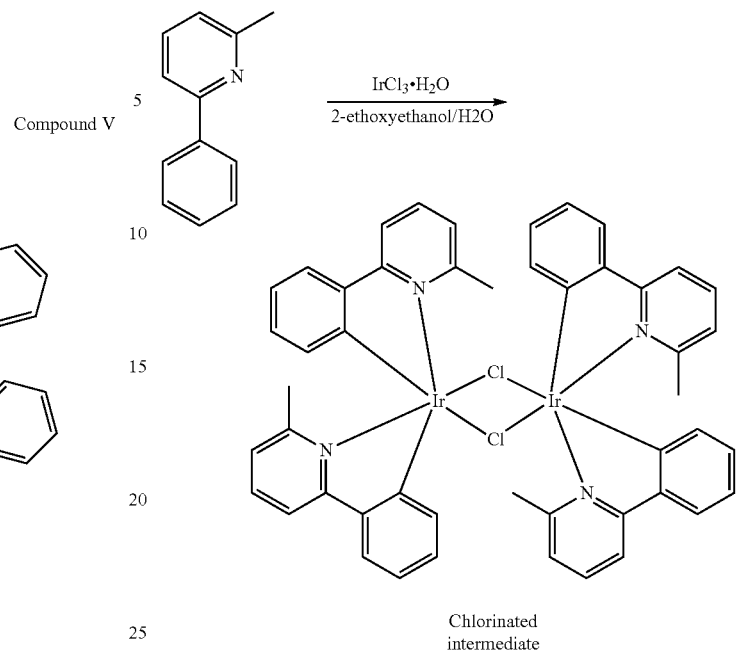

Chlorinated intermediate

Synthesis of chlorinated intermediate: 5 g (29.8 mmol) 2-methyl-6-phenylpyridine and 4.8 g (13 mmol) iridium chloride (IrCl$_3$·H$_2$O) were added together in a flask with 35 mL 2-ethoxyethanol and 8 mL H$_2$O as solvent. The solution was heated to reflux for 24 hours and the red precipitate product was filtered off and washed with methanol. The product was used without further purification. 4.2 g (3.7 mmol) of intermediate A was collected.

Synthesis of brominated mixture: 3.4 g (3.01 mmol) the above chlorinated intermediate, 1.55 g (6.6 mmol) 2-(3-bromophenyl)pyridine, and 1.54 g (6.02 mmol) silver trifluoromethanesulfonate (AgOTf) were weighed together in a flask with approximately 70 mL 2-ethoxyethanol as solvent. The solution was heated to reflux for 18 hours and the product was precipitated in methanol and filtered. The crude intermediate was dry packed on celite and purified by column chromatography using hexanes/dichloromethane as eluent. 1.3 g (1.7 mmol) of brominated mixture was collected.

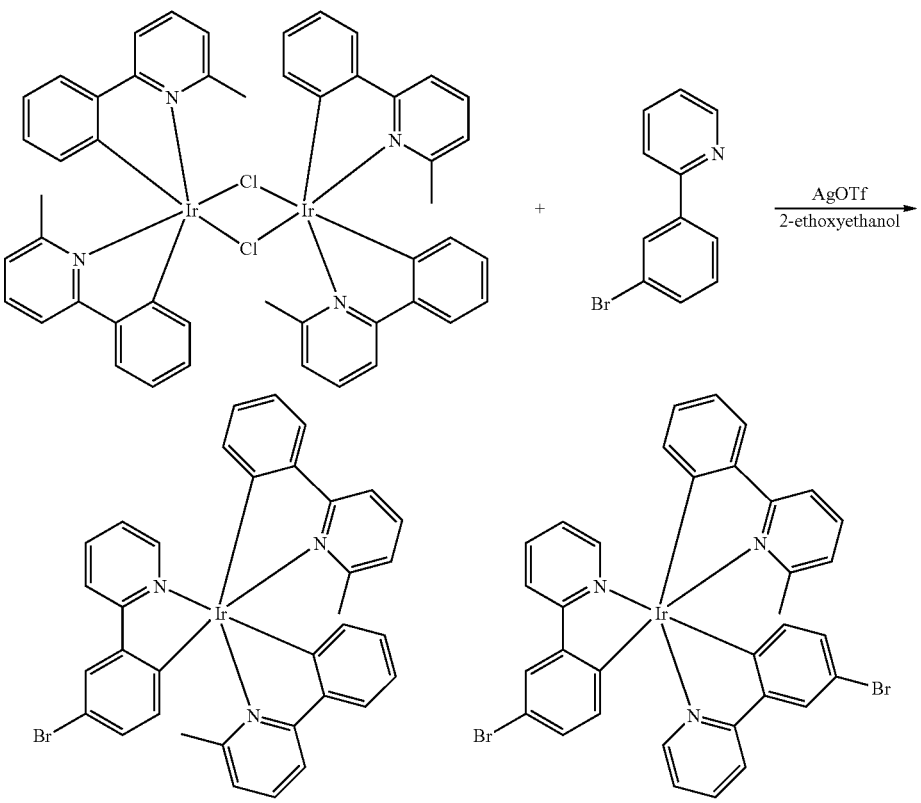

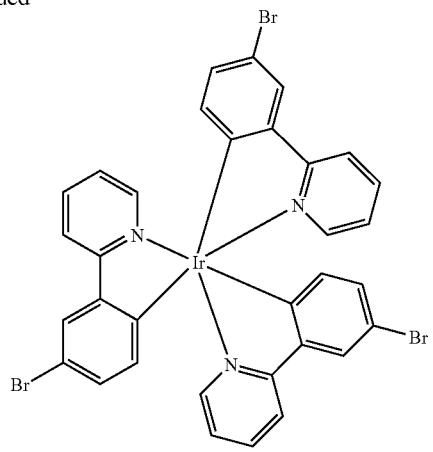

Brominated mixture

Synthesis of boronic ester: 1.3 g of the above brominated mixture, 0.86 g (3.4 mmol) bis(pinacolato)diboron, 0.042 g (0.051 mmol) Pd(dppf)$_2$Cl$_2$, and 0.5 g (5.1 mmol) potassium acetate were weighed in a flask with dioxane used as solvent. The solution was purged with nitrogen and heated to 90° C. for 12 hours. The dioxane was removed by rotary evaporation; the solid was dissolved in dichloromethane and washed with water. The dichloromethane was removed by rotary evaporation and the material was dry packed on celite and purified by column chromatography using hexanes/dichloromethane as eluent. 0.52 g (0.64 mmol) of desired mono boronic ester compound was collected.

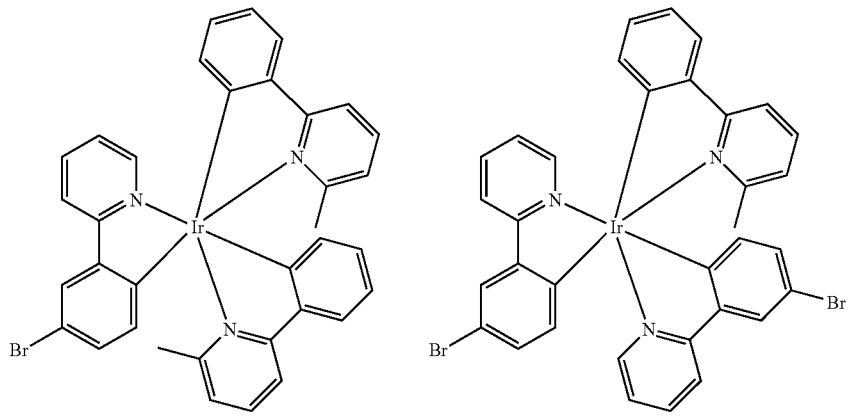

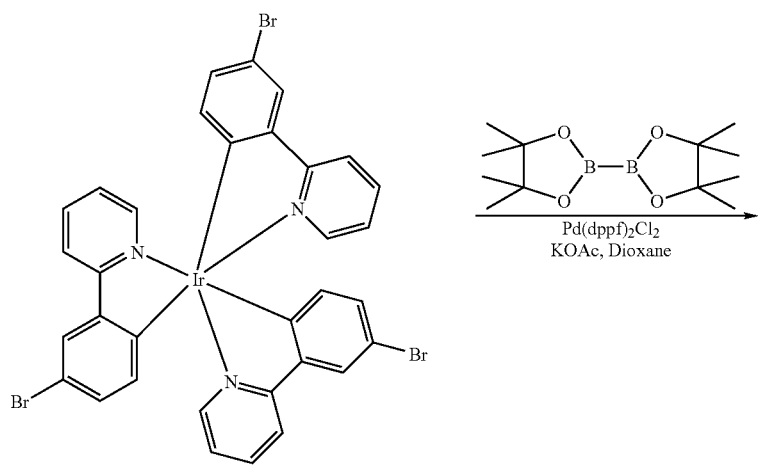

-continued

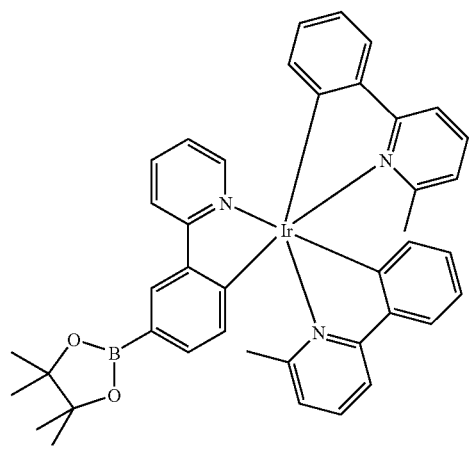

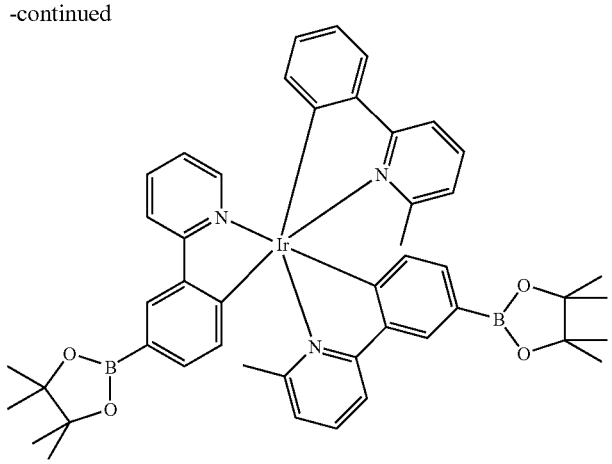

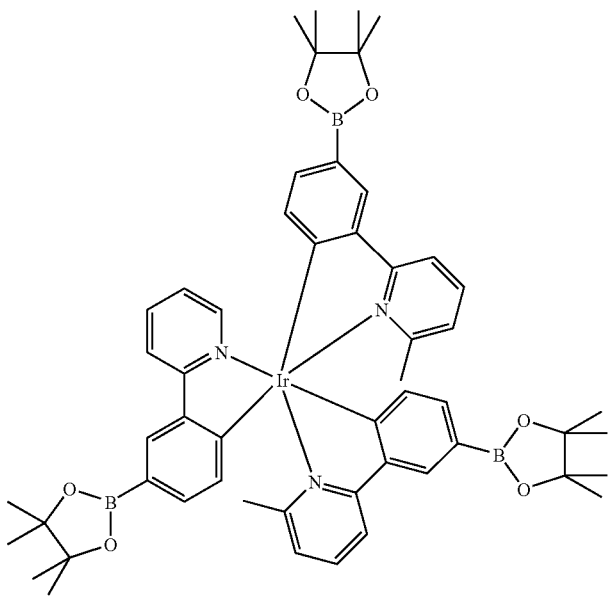

Boronic esters

Synthesis of Compound V: 0.52 g (0.64 mmol) of the above mono boronic ester, 0.3 g (1.93 mmol) phenylboronic acid, 0.006 g (0.0064 mmol) tris(dibenzylideneacetone)dipalladium(0) [Pd$_2$(dba)$_3$], 0.10 g (0.025 mmol) 2-dicyclohexylphosphino-2',6'-dimethoxybiphenyl (SPhos), and 0.4 g (1.92 mmol) potassium phosphate tribasic (K$_3$PO$_4$) were weighed into a flask. 30 mL toluene and 10 mL water were used as solvent and the solution was purged with nitrogen. The solution was heated to reflux for twelve hours. Upon cooling, the organic layer was separated, and dried with MgSO$_4$. The product was separated by column chromatography using hexanes/dichloromethane as eluent. The solvent was removed by rotary evaporation, and the product dried under vacuum. The product was further purified by high vacuum sublimation at 250° C. resulting in 0.3 g (0.39 mmol).

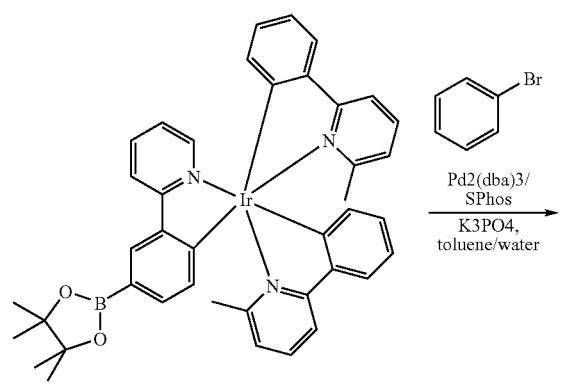

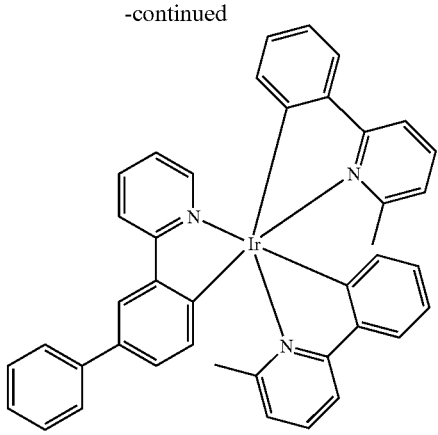

Compound V

Synthesis of Compound VI:

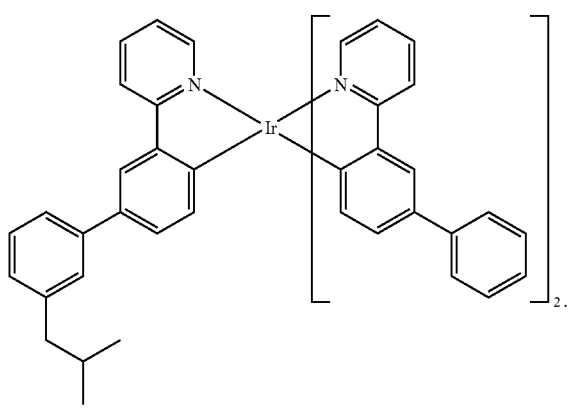

A mixture was prepared of 2-bromopyridine (40 g, 253 mmol), 3-bromophenylboronic acid (61.0 g, 303.8 mmol), triphenylphosphine (6.64 g, 25.3 mmol), potassium carbonate (87.4 g, 632.5 mmol) in of 300 mL dimethoxyethane, and 200 mL of water. Nitrogen was bubbled directly into the mixture for 20 minutes, then palladium acetate was added (2.84 g, 12.65 mmol). The reaction mixture was heated to reflux under nitrogen. At the end of the day, a trace of 2-bromopyridinme was detected by TLC. Thus an additional 10 grams of 2-bromophenylboronic acid was added and reaction continued to reflux overnight. The reaction mixture was cooled and water was added along with ethyl acetate. The layers were separated and the aqueous layer was extracted with ethyl acetate. The organic layers were dried over magnesium sulfate, filtered, and evaporated to a brown oil. The oil was purified by column chromatography eluting with 0 to 40% ethyl acetate/hexanes followed by distillation under vacuum. Obtained 45.1 g of desired product (52% yield), as confirmed by GC-MS.

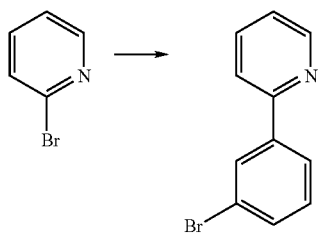

A mixture was prepared of 2-(3-bromophenyl)pyridine (12.2 g, 52.10 mmol), 3-(4,4,5,5-tetramethyl-1,3,2-dioxaborolan-2-yl)phenol (13.76 g, 62.53 mmol), 2-dicyclohexylphosphino-2',6'-dimethoxybiphenyl (856 mg, 2.08 mmol), potassium phosphate tribasic monohydrate (36 g, 156.3 mmol) in 180 mL of dioxane, and 18 mL of water. Nitrogen was bubbled directly into the mixture for 20 minutes, then tris(dibenzylideneacetone)dipalladium(0) was added (477 mg, 0.52 mmol). The reaction mixture was heated at 100° C. for 3 hours under nitrogen, then allowed to cool to room temperature overnight. Water was added to the reaction mixture and the mixture was extracted three times with ethyl acetate. The organic extracts were dried over magnesium sulfate, filtered and evaporated to a residue. The residue was purified by column chromatography eluting with 20 and 40% ethyl acetate/hexanes. Obtained 12.5 g of a yellow oil (97% yield), as confirmed by GC-MS.

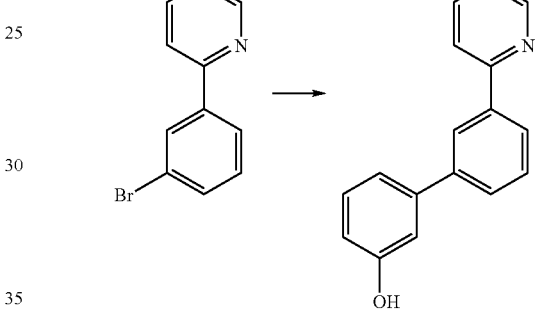

12.5 gram (50.6 mmol) 3'-(pyridin-2-yl)biphenyl-3-ol, 12 ml pyridine, and 200 ml methylene chloride were mixed in a 500 ml round bottle flask at 0° C. To the mixture, 14.3 gram (101.2 mmol) trifluoroacetic anhydride was added and stirred for 30 min at 0° C., then stirred at room temperature for 1 hour. The reaction mixture was washed with water several times. 19 gram (100% yield) triflate was obtained after evaporation of solvent, as confirmed by GC-MS.

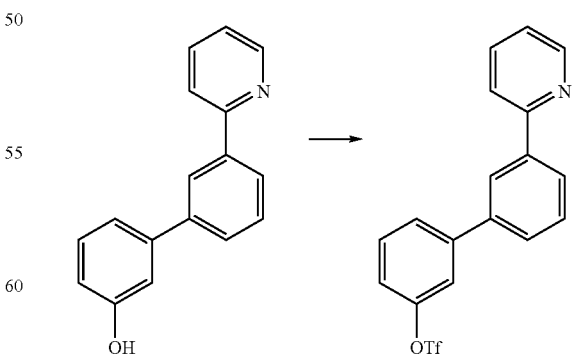

8.8 g (23.2 mmol) 3'-(pyridin-2-yl)biphenyl-3-yl trifluoromethanesulfonate, 4.7 g (46 mmol) isobutaneboronic acid, 211 mg Pd₂(dba)₃ (0.23 mmol), 396 mg (0.965 mmol) S-Phos, 16.7 gram (72.6 mmol) K₃PO₄H₂O, and 300 ml toluene were charged in a 500 ml round bottle flask. The reaction mixture was heated up to reflux under nitrogen overnight with stirring. The reaction mixture was purified by silica gel chromatography with 10% (v/v) ethyl acetate in hexane as elute. 5.8 gram solid (yield 87%) product was obtained, as confirmed by GC-MS.

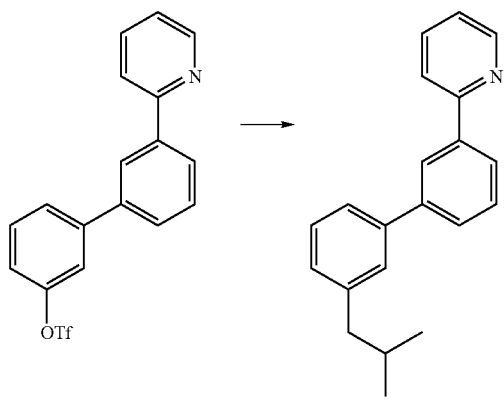

3.4 gram (11.8 mmol) 2-(3'-isobutylbiphenyl-3-yl)pyridine, 2.0 gram (5.3 mmol) IrCl₃.3H₂O, and 150 ml solvent mixture (2 ethoxyethanol/water: 3:1) were charged in a 250 ml round bottle flask. The reaction mixture was heated up to reflux under nitrogen overnight. The reaction mixture was cooled down and added ~100 ml methanol, then filtered. The solid was washed with methanol and dried. About 3.85 gram of chloro-bridged iridium dimer was obtained and used for next step without further purification.

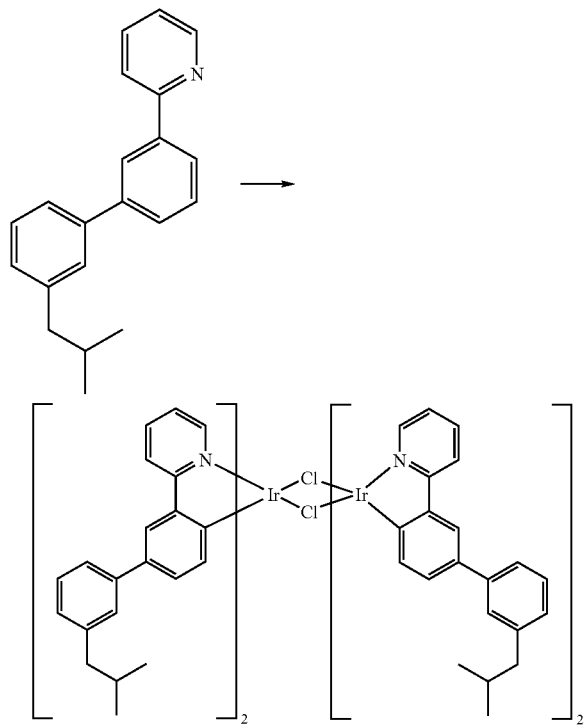

A mixture was prepared of 2-bromopyridine (8.66 g, 54.8 mmol), 3-methoxy phenylboronic acid (10 g, 65.8 mmol), triphenylphosphine (1.44 g, 5.48 mmol), potassium carbonate (18.9 g, 137 mmol) in 100 mL dimethoxyethane and 66 mL of water. Nitrogen was bubbled directly into the mixture for 20 minutes, then palladium acetate was added (0.61 g, 2.74 mmol). The reaction mixture was heated to reflux overnight under nitrogen. The reaction mixture was cooled and water was added along with ethyl acetate. The layers were separated and the aqueous layer was extracted with ethyl acetate. The organic layers were dried over magnesium sulfate, filtered, and evaporated to residue. The residue was purified by column chromatography eluting with 0 to 20% ethyl acetate/hexanes. Obtained 9.7 g of a clear oil (96% yield), as confirmed by GC-MS.

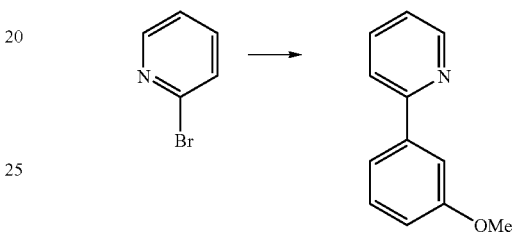

A mixture of 2-(3-methoxyphenyl)pyridine (9.7 g, 52.37 mmol) and pyridine hydrochloride (72.6 g, 628.44 mmol) was prepared. The mixture was heated to 220° C. The reaction was done in 2 hours. Water was added to the cooled mixture and then extracted with dichloromethane twice. The organic extracts were dried over magnesium sulfate, filtered, and evaporated to a residue. The residue was purified by column chromatography eluting with 0, 1, and 2% methanol/dichloromethane, followed by Kugelrohr distillation and recrystallization from 2:1 hexane/ethyl acetate. Obtained 5 g of a white solid (56% yield), as confirmed by GC-MS.

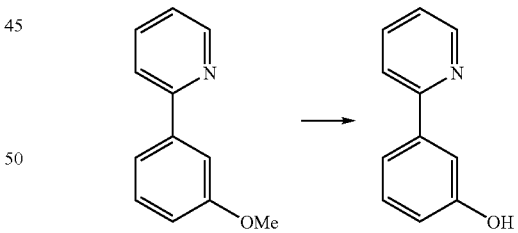

A solution was prepared of 3-(pyridin-2-yl)phenol (5 g, 29.21 mmol) in 100 mL of dichloromethane. To this solution was added pyridine (4.7 mL, 58.42 mmol) and the solution was cooled in an ice-salt bath. To this solution was added a solution of trifluoromethanesulfonic anhydride (9.8 mL, 58.42 mmol) in 20 mL of dichloromethane dropwise. The reaction was allowed to warm slowly and was complete after 2 hours. Water and dichloromethane was added and the layers were separated. The aqueous layer was extracted with dichloromethane. The organic layers were dried over magnesium sulfate, filtered and evaporated to a residue. The residue was purified by column chromatography eluting with 5, 10, and 15% ethyl acetate/hexanes. Obtained 8 g of a clear liquid (90% yield), as confirmed by GC-MS.

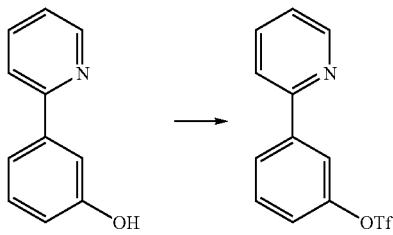

3.85 gram (2.41 mmol) the above chloro-bridged iridium dimer, 1.42 gram (5.3 mmol) silver triflate AgOSOCF₃, 2.93 gram (9.64 mmol) 3-(pyridin-2-yl)phenyl trifluoromethane sulfonate and ~300 ml 2-ethoxyethanol were mixed in a 500 ML round bottle flask. The mixture was heated up to reflux under nitrogen for 24 hours. The reaction mixture was purified on silica gel with 50% methylene chloride in hexane. About 900 mg product was separated from the reaction mixture which containing four ligand-scrambled iridium complexes. The product was confirmed by LC-MS. The desired fraction can be obtained through column chromatography.

700 mg (0.647 mmol) of the triflate iridium complex, 394 mg (3.23 mmol) phenylboronic acid, 60 mg Pd$_2$(dba)$_3$ (0.065 mmol), 110 mg (0.268 mmol) S-Phos, 840 mg (3.65 mmol) K$_3$PO$_4$.H$_2$O and 50 ml dry toluene were charged in a 100 ml three-necked flask. The reaction mixture was bubbled nitrogen for 30 mins then heated up to reflux for 20 hours under nitrogen. The reaction mixture was separated on silica gel column. 610 mg solid (99% yield) was obtained, as confirmed by NMR and LC-MS.

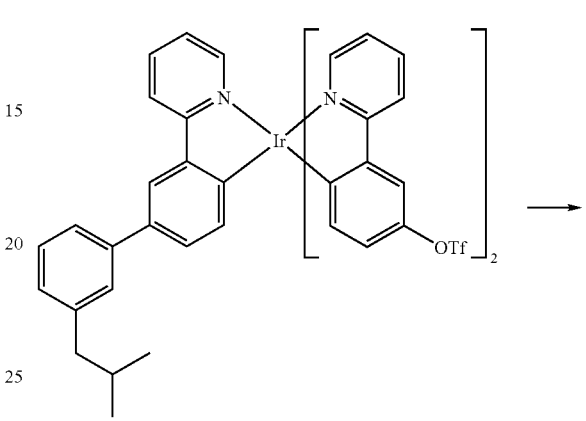

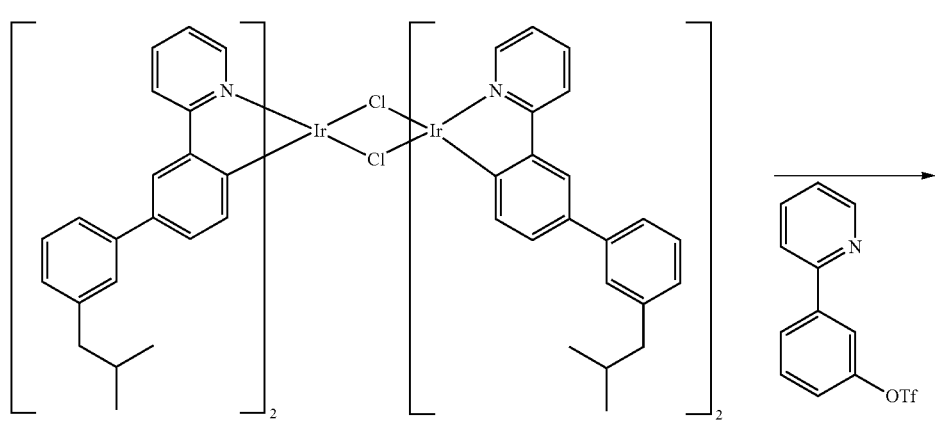

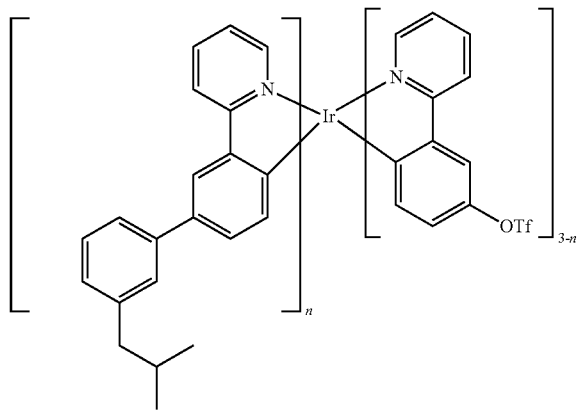

n = 0, 1, 2, 3

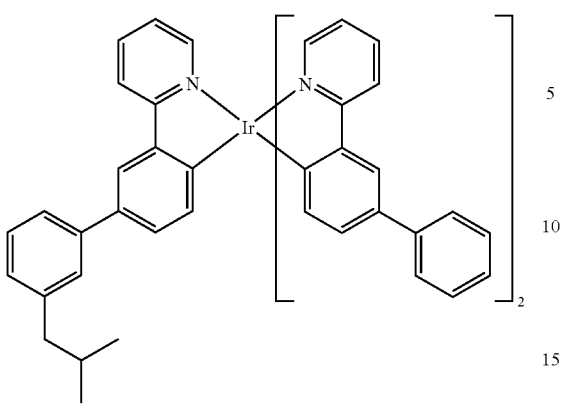

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

MATERIAL DEFINITIONS

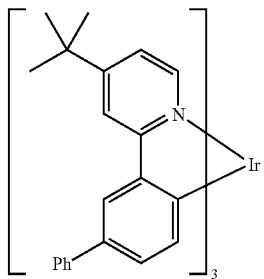

Green-1
tris(2-(biphenyl-3-yl)-4-tert-butylpyridine)iridium(III)

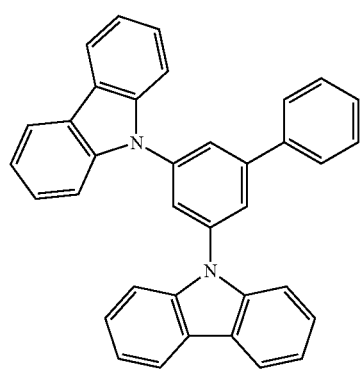

Host-1
3,5-di(9H-carbazol-9-yl)biphenyl

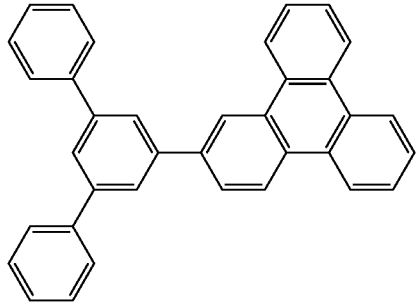

Host-2

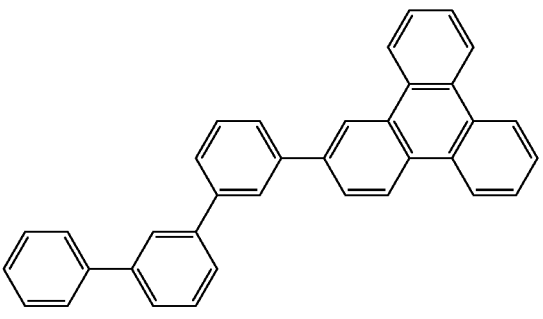

Host-3

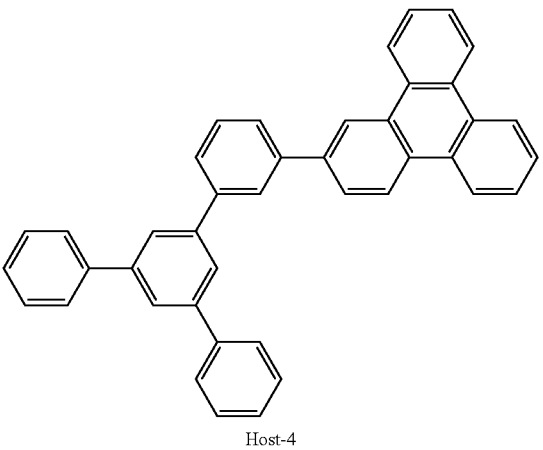

Host-4

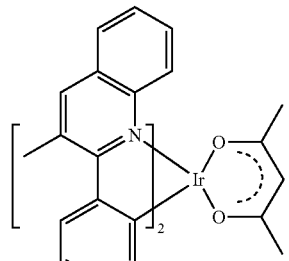

Red-1

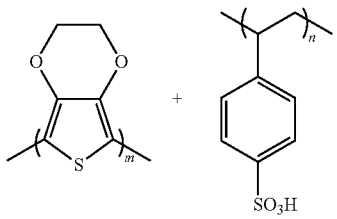

PEDOT/PSS

-continued

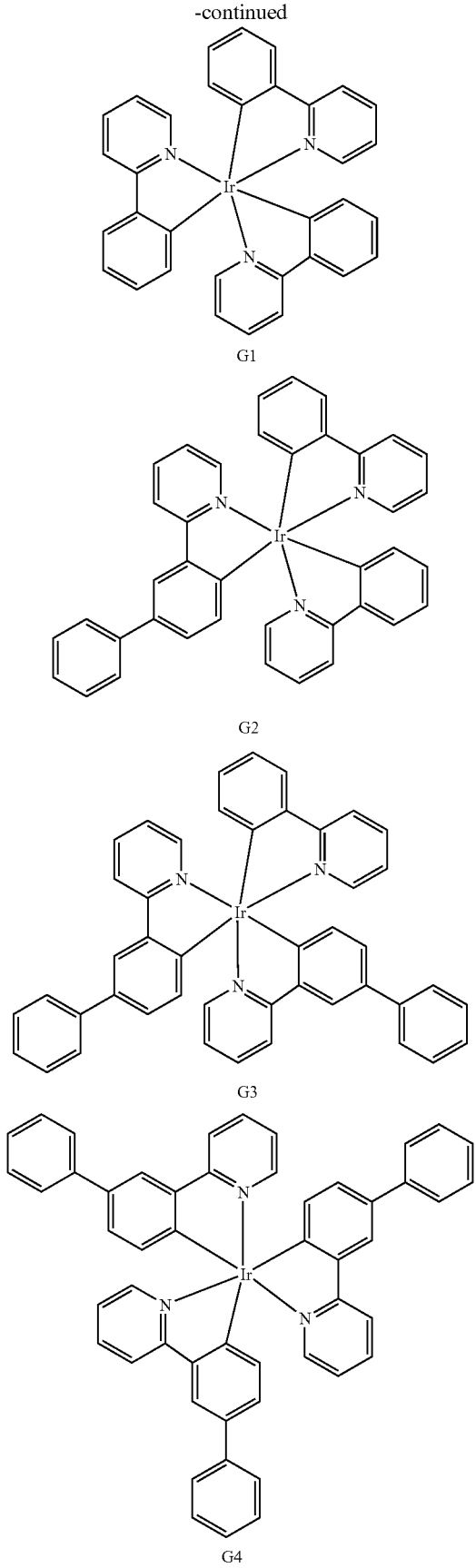

Green-2: A mixture of compounds G1, G2, G3, and G4 in a ratio of 2:37:53:7.

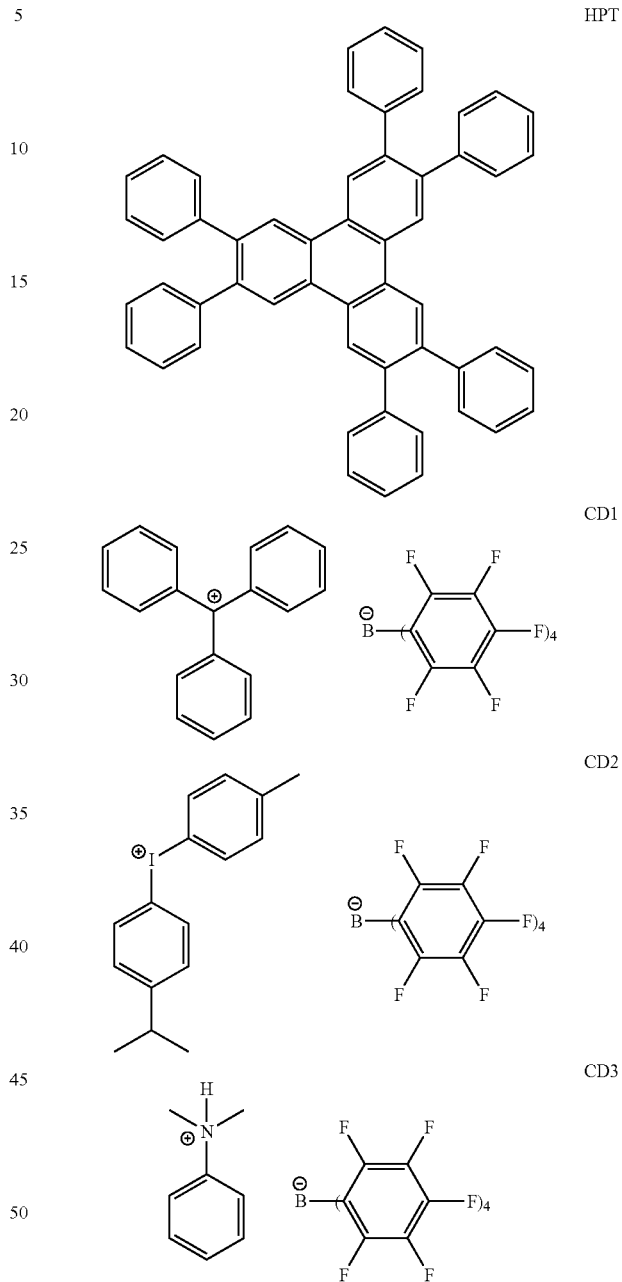

As used herein, abbreviations refer to materials as follows:

| | |
|---|---|
| CBP: | 4,4'-N,N-dicarbazole-biphenyl |
| m-MTDATA | 4,4',4''-tris(3-methylphenylphenylamino)triphenylamine |
| $Alq_3$: | aluminum(III)tris(8-hydroxyquinoline) |
| Bphen: | 4,7-diphenyl-1,10-phenanthroline |
| n-BPhen: | n-doped BPhen (doped with lithium) |
| $F_4$-TCNQ: | tetrafluoro-tetracyano-quinodimethane |
| p-MTDATA: | p-doped m-MTDATA (doped with $F_4$-TCNQ) |
| $Ir(ppy)_3$: | tris(2-phenylpyridine)-iridium |
| $Ir(ppz)_3$: | tris(1-phenylpyrazoloto,N,C(2')iridium(III) |
| BCP: | 2,9-dimethyl-4,7-diphenyl-1,10-phenanthroline |

-continued

| | |
|---|---|
| TAZ: | 3-phenyl-4-(1'-naphthyl)-5-phenyl-1,2,4-triazole |
| CuPc: | copper phthalocyanine |
| ITO: | indium tin oxide |
| NPD: | N,N'-diphenyl-N-N'-di(1-naphthyl)-benzidine |
| TPD: | N,N'-diphenyl-N-N'-di(3-toly)-benzidine |
| BAlq: | aluminum(III)bis(2-methyl-8-hydroxyquinolinato)4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT:PSS: | an aqueous dispersion of poly(3,4-ethylenedioxythiophene) with polystyrenesulfonate (PSS) |

The invention claimed is:

1. An organic light-emitting device, comprising:
a first electrode;
a second electrode;
a first organic layer disposed between the first electrode and the second electrode, wherein the first organic layer is non-electroluminescent, and wherein the first organic layer comprises a cross-linked metal complex; and
a second organic layer disposed between the first electrode and the second electrode, wherein the second organic layer is emissive, and wherein the second organic layer comprises an electroluminescent organic material;
wherein the cross-linked metal complex is formed by cross-linking a cross-linkable iridium complex having the formula:

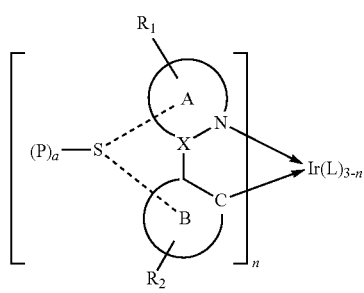

wherein L is a ligand coordinated to the iridium;
wherein A and B are each a 5 or 6-membered aromatic ring, and wherein A-B represents a bonded pair of aromatic rings coordinated to the iridium via a nitrogen atom on ring A and an sp² hybridized carbon atom on ring B;
wherein variable "n" has an integer value of 1-3;
wherein X is a carbon or nitrogen atom;
wherein P is a polymerizable group with variable "a" having an integer value of 1-5;
wherein S is a spacer group that includes one or more linkage units that are each independently selected from the group consisting of: alkylene, heteroalkylene, arylene, heteroarylene, borane, ether, ester, amine, imine, amide, imide, thioether, and phosphine; and
wherein each of rings A and B are optionally substituted with groups $R_1$ and $R_2$, respectively, wherein each of $R_1$ and $R_2$ represents one or more independently selected substitutions located on any position of their respective rings, wherein each of the substitutions are fused or linked to their respective rings, and wherein each of the substitutions are independently selected from the group consisting of: alkyl, heteroalkyl, aryl, and heteroaryl;
wherein: (a) the first electrode is an anode and the first organic layer is in direct contact with the first electrode;
or (b) the device further comprises a third organic layer disposed between the first organic layer and the second organic layer; or (c) wherein the structure A-B is

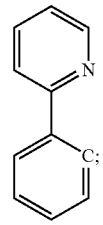

or any combination of (a), (b), and (c).

2. The device of claim 1, wherein the first electrode is an anode and the first organic layer is in direct contact with the first electrode.

3. The device of claim 1, further comprising a third organic layer disposed between the first organic layer and the second organic layer.

4. The device of claim 1, wherein the structure $R_1$-A-B—$R_2$ is selected from the group consisting of:

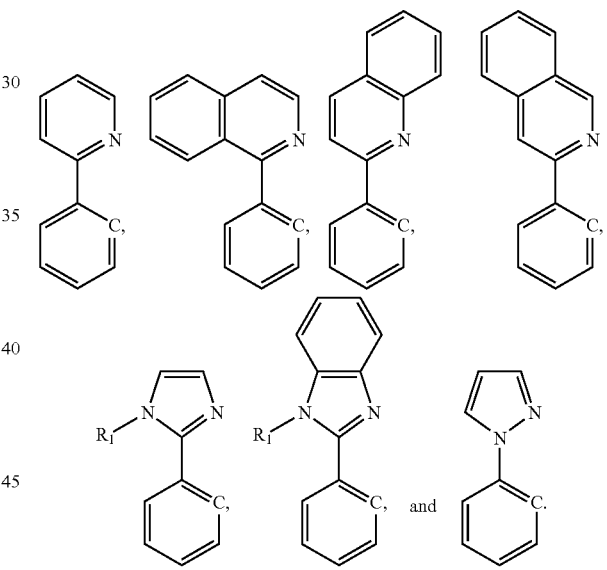

5. The device of claim 1, wherein the structure A-B is

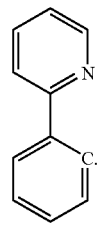

6. The device of claim 5, wherein the first organic layer is a hole injection layer.

7. The device of claim 6, wherein the first organic layer is in direct contact with the first electrode.

8. The device of claim 1, wherein the spacer group separates the polymerizable group from one of the pair of aromatic rings by a distance of at least 3 bonds.

9. The device of claim 8, wherein the spacer group separates the polymerizable group from one of the pair of aromatic rings by a distance of at least 5 bonds.

10. The device of claim 9, wherein the spacer group separates the polymerizable group from one of the pair of aromatic rings by a distance of at least 7 bonds.

11. The device of claim 1, wherein the spacer group includes an amine group.

12. The device of claim 1, wherein the polymerizable group is selected from the group consisting of: vinyl, acrylate, epoxide, oxetane, trifluoroethylene, benzocyclobutene, siloxane, maleimide, cyanate ester, ethynyl, nadimide, phenylethynyl, biphenylene, phthalonitrile, and boronic acid.

13. The device of claim 1, wherein the polymerizable group is selected from the group consisting of: vinyl, siloxane, and boronic acid.

14. The device of claim 1, wherein the variable "a" has a value of 2 or greater.

15. The device of claim 1, wherein the structure $(P)_a$—S is selected from the group consisting of:

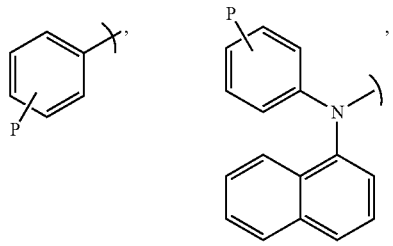

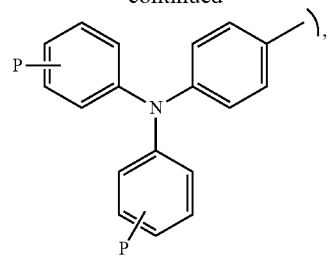

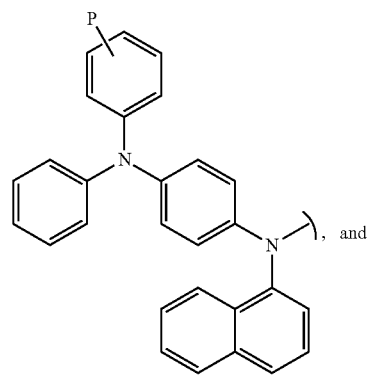

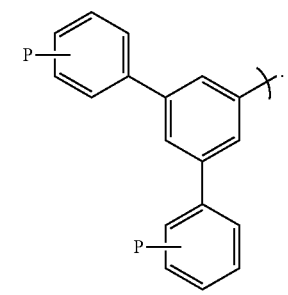

16. The device of claim 1, wherein the cross-linkable iridium complex is selected from the group consisting of:

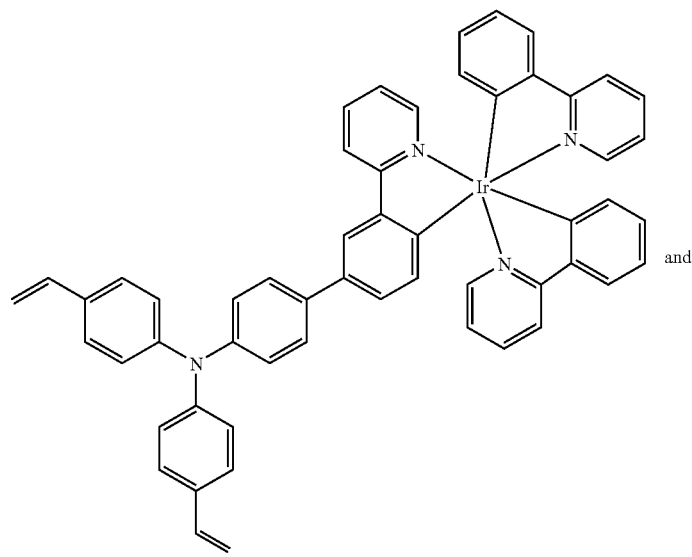

-continued
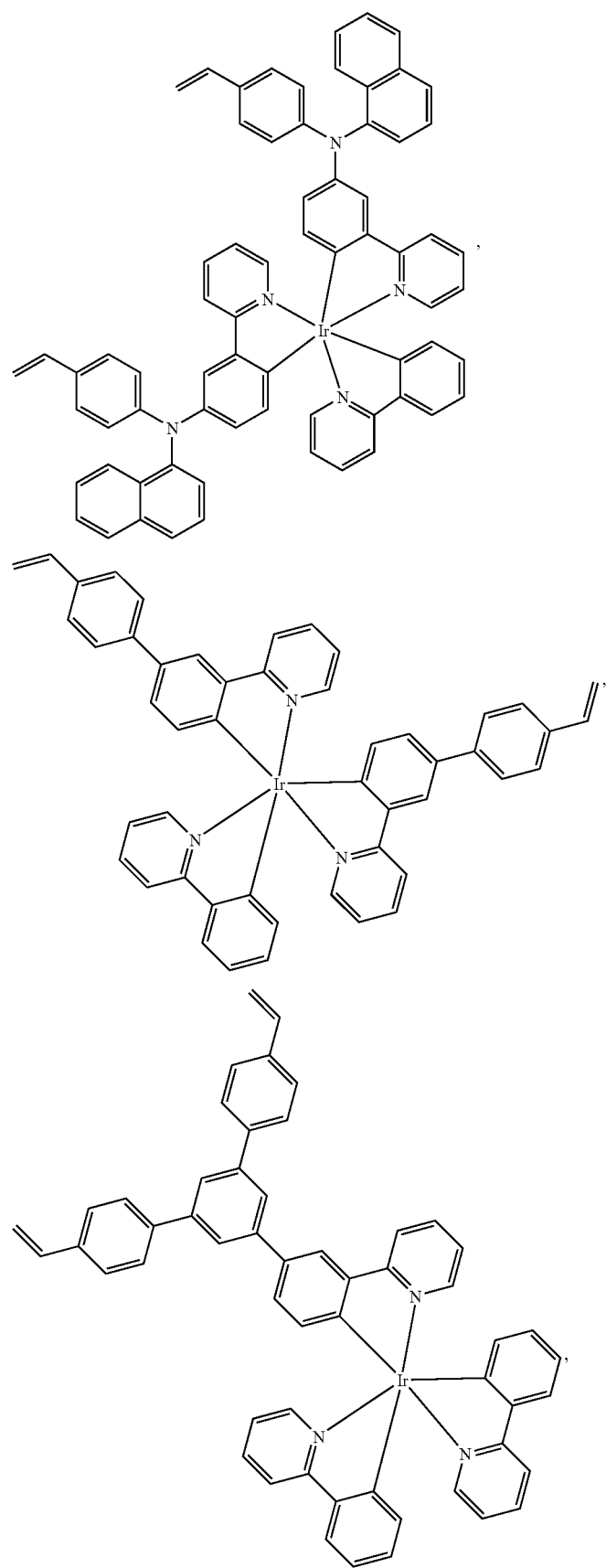

113 114
-continued
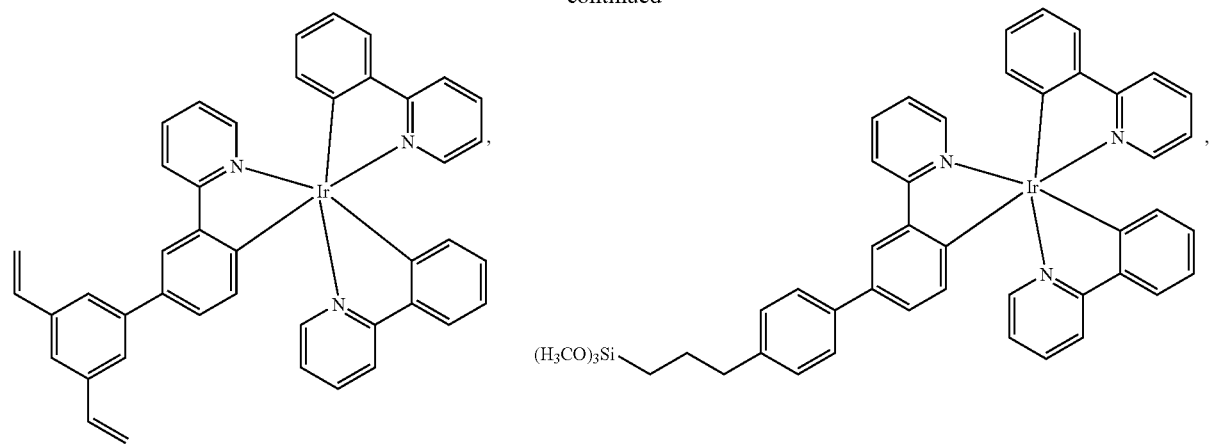
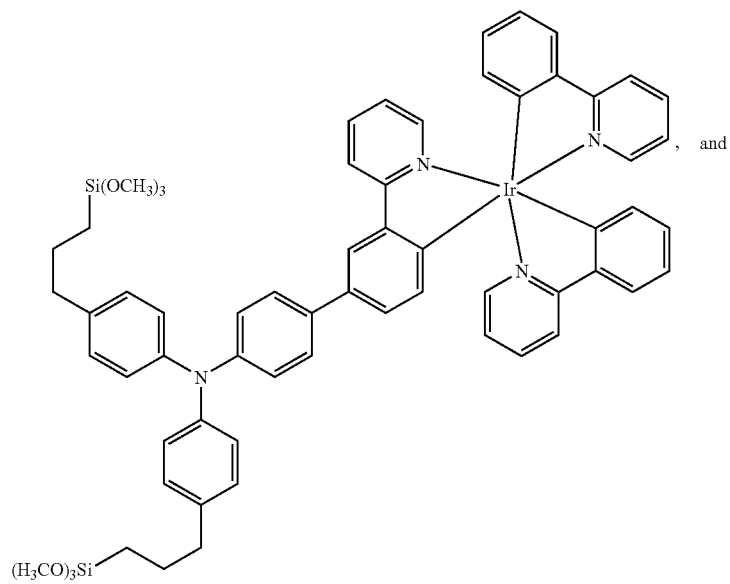
, and
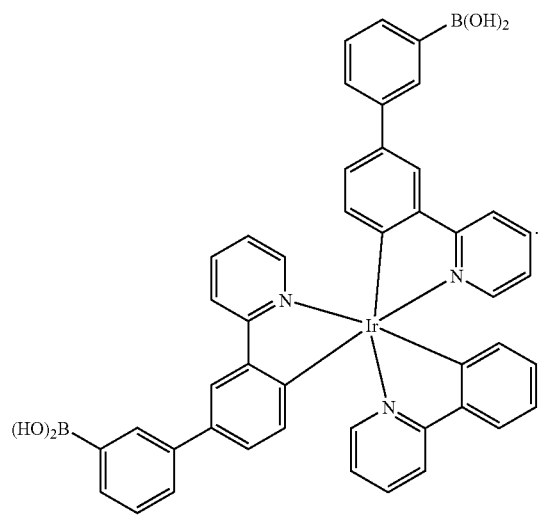

17. The device of claim 1, wherein the structure $(P)_a$—S is selected from the group consisting of:
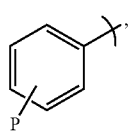 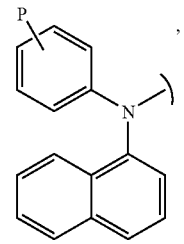
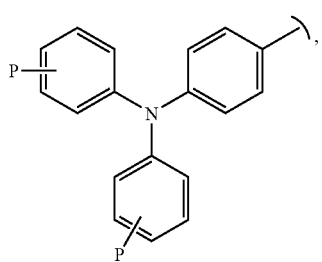
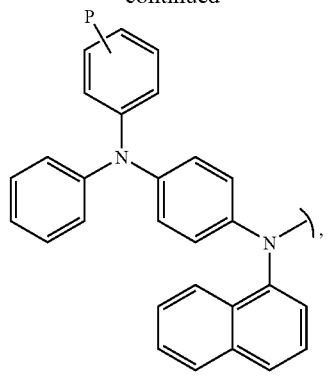
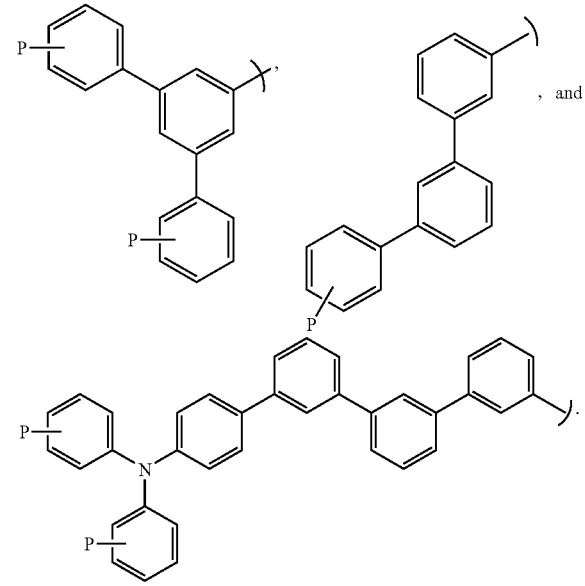
, and
18. The device of claim 1, wherein the cross-linkable iridium complex is selected from the group consisting of:
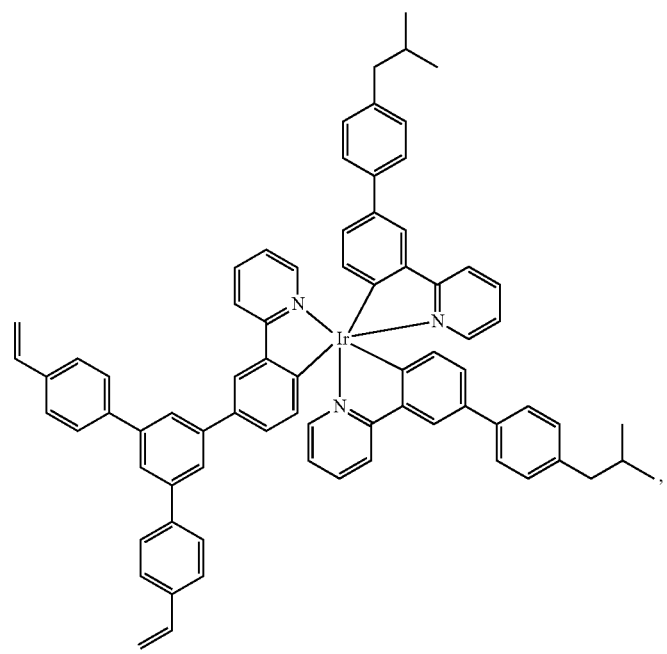

-continued
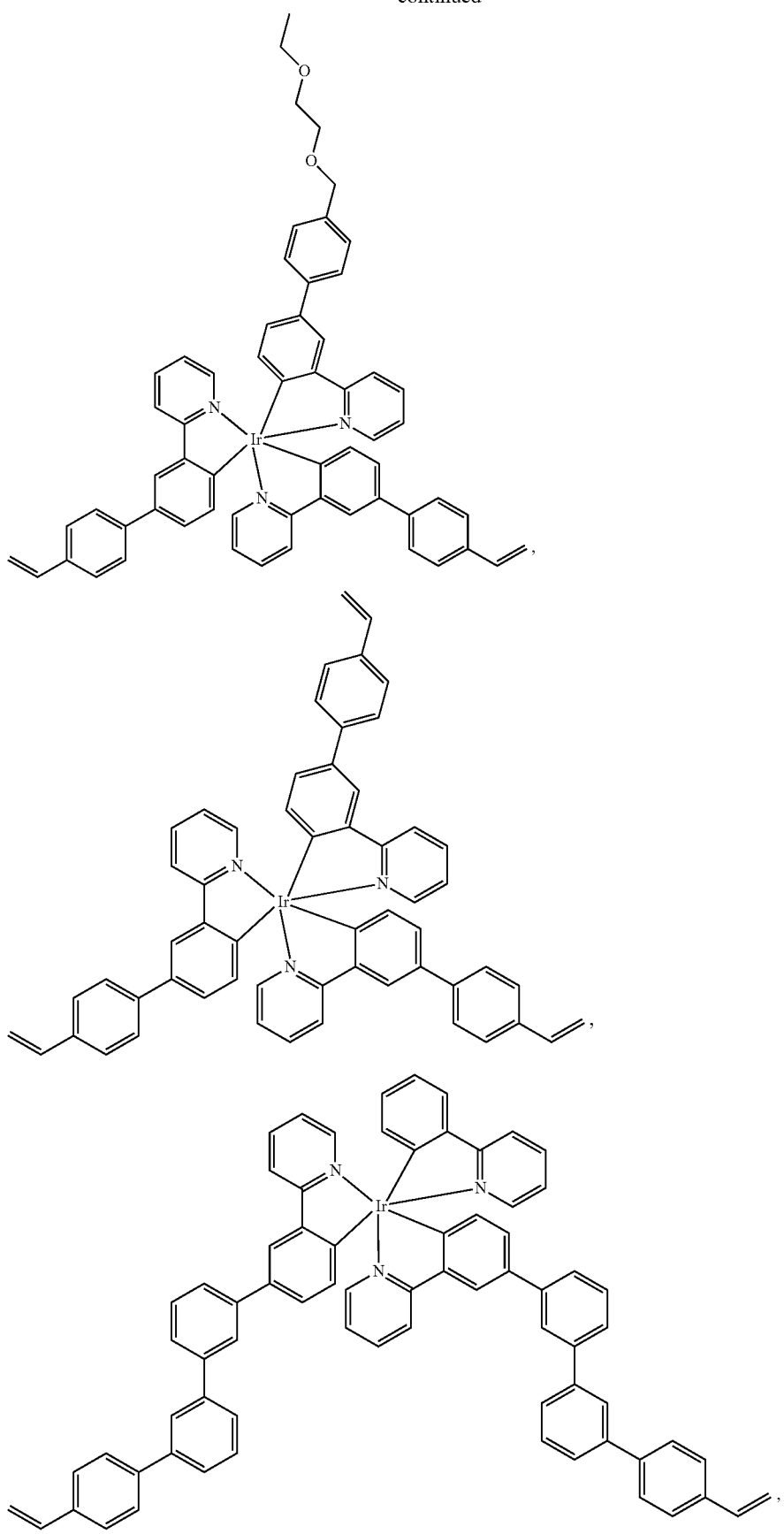

-continued
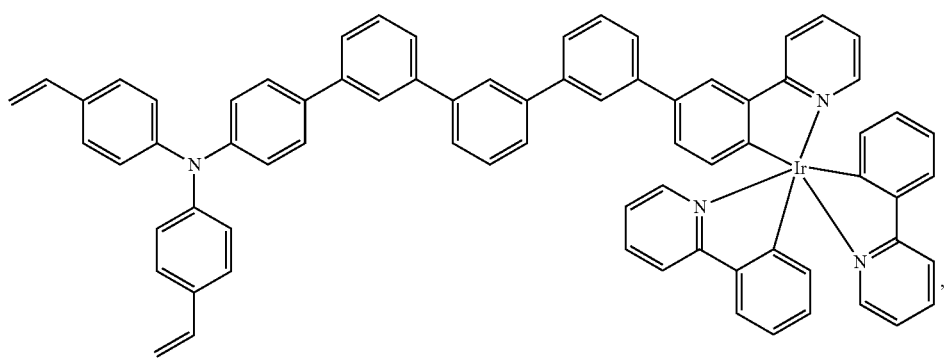
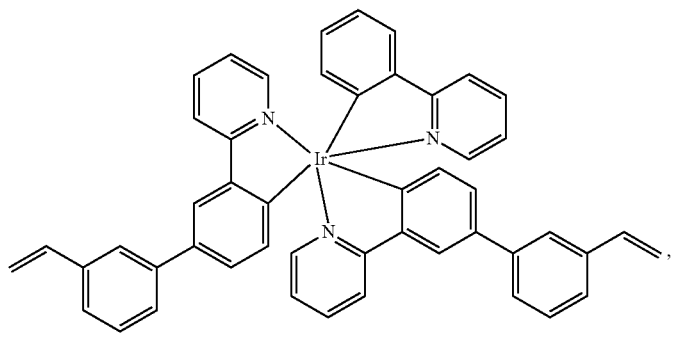
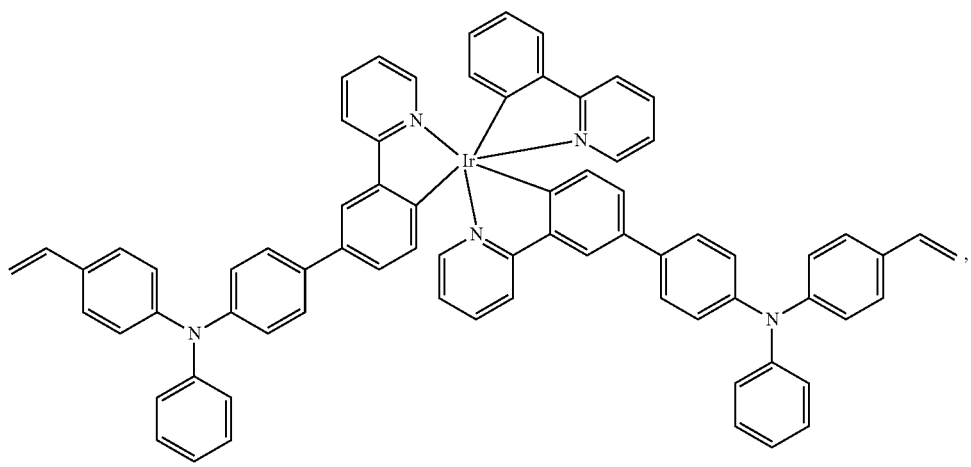
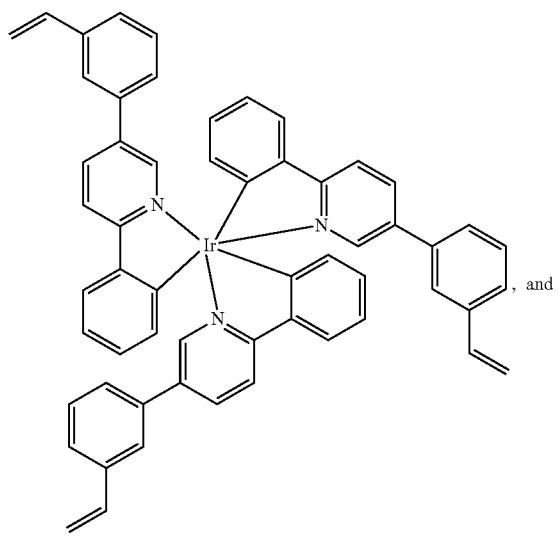
, and

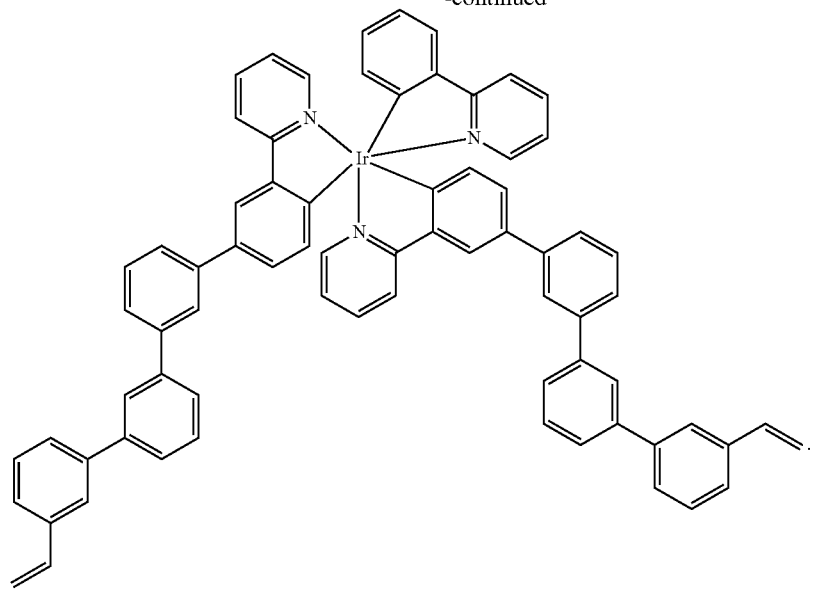

19. The device of claim 1, wherein the cross-linkable iridium complex is a polymeric molecule or a part thereof.

20. The device of claim 19, wherein the cross-linkable iridium complex has the formula:

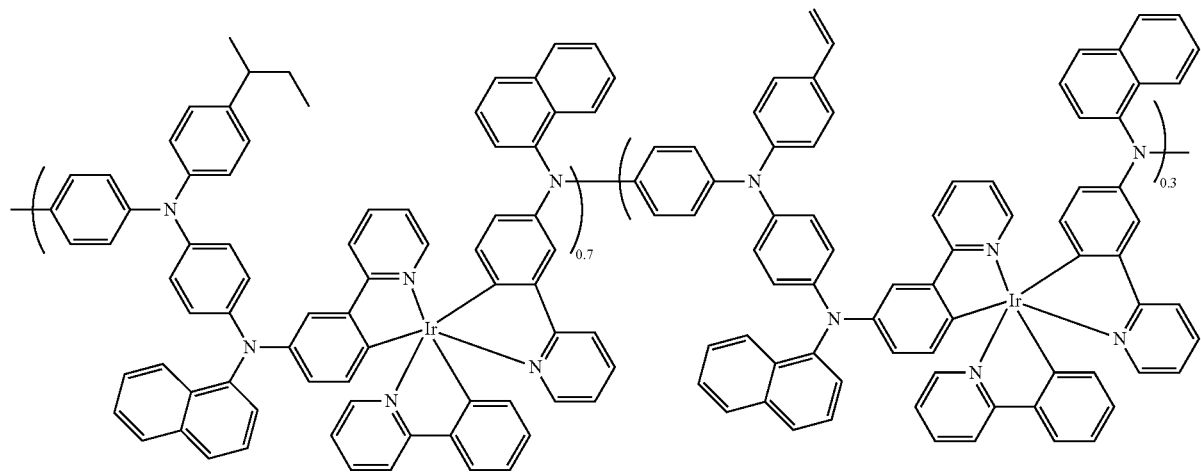

21. The device of claim 1, wherein the cross-linkable iridium complex has the formula:

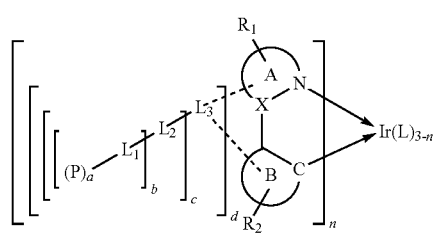

wherein $L_1$, $L_2$, and $L_3$ are each a bond or a linkage unit independently selected from the group consisting of: alkylene, heteroalkylene, arylene, heteroarylene, borane, ether, ester, amine, imine, amide, imide, thioether, and phosphine; and wherein the variables "a," "b," "c," and "d" each has an integer value of 1-5.

22. The device of claim 21, wherein the cross-linkable iridium complex has the formula:

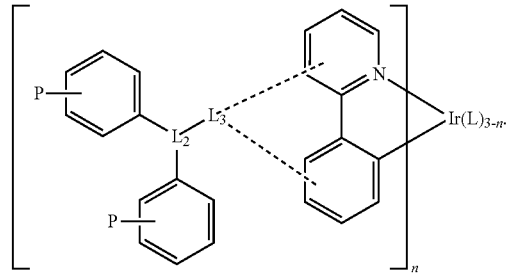

23. The device of claim 22, wherein the cross-linkable iridium complex has the formula:

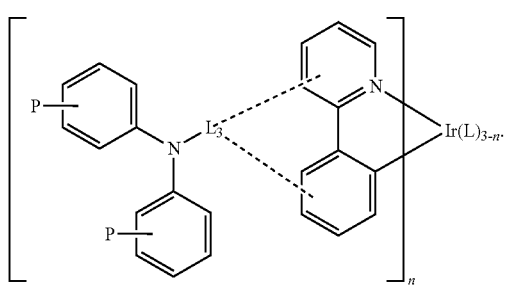

24. The device of claim 23, wherein the cross-linkable iridium complex has the formula:

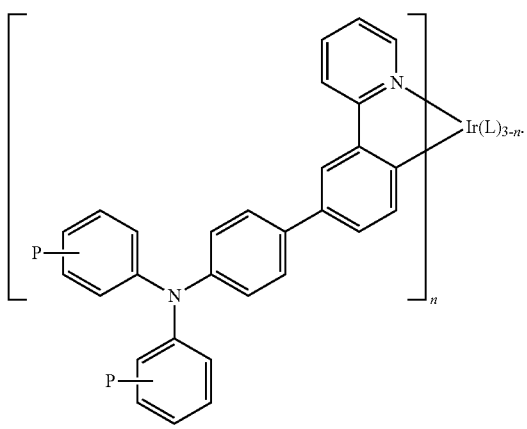

25. The device of claim 1, wherein the first organic layer further comprises a dopant.

26. The device of claim 25, wherein the dopant is an electron acceptor.

27. The device of claim 25, wherein the dopant is selected from the group consisting of:

CD1

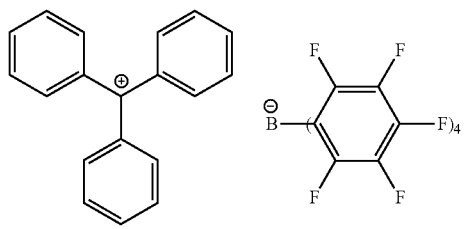

CD2

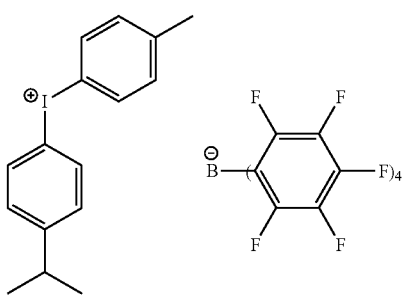

CD3

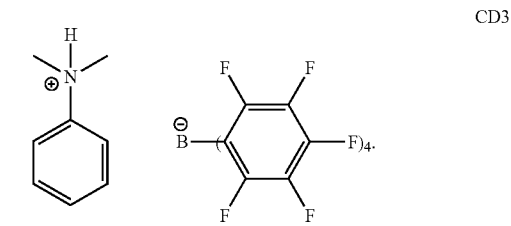

28. The device of claim 1, wherein the first electrode is an anode and the second electrode is a cathode; and wherein the first organic layer is in direct contact with the first electrode.

29. The device of claim 28, wherein the first organic layer is a hole injection layer.

30. The device of claim 1, wherein the spacer group S is represented by the formula:

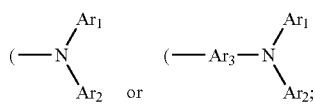

and wherein $Ar_1$, $Ar_2$, and $Ar_3$ are each an aryl group.

31. The device of claim 1, wherein the first organic layer is a hole injection layer.

* * * * *